US010442856B2

(12) United States Patent
Gusarova et al.

(10) Patent No.: US 10,442,856 B2
(45) Date of Patent: Oct. 15, 2019

(54) METHODS OF TREATING OBESITY WITH ANTI-ANGPTL8 ANTIBODIES

(71) Applicant: Regeneron Pharmaceuticals, Inc., Tarrytown, NY (US)

(72) Inventors: Viktoria Gusarova, Pleasantville, NY (US); Jesper Gromada, Scarsdale, NY (US); Andrew J. Murphy, Croton-on-Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 15/815,881

(22) Filed: Nov. 17, 2017

(65) Prior Publication Data

US 2018/0134781 A1 May 17, 2018

Related U.S. Application Data

(60) Provisional application No. 62/423,639, filed on Nov. 17, 2016.

(51) Int. Cl.
| | | |
|---|---|---|
| *C07K 16/22* | (2006.01) | |
| *A61K 39/395* | (2006.01) | |
| *A61K 45/06* | (2006.01) | |
| *A61K 39/00* | (2006.01) | |

(52) U.S. Cl.
CPC .......... *C07K 16/22* (2013.01); *A61K 39/3955* (2013.01); *A61K 45/06* (2013.01); *A61K 2039/505* (2013.01); *C07K 2317/21* (2013.01); *C07K 2317/33* (2013.01); *C07K 2317/34* (2013.01); *C07K 2317/56* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,569,992 B1 | 5/2003 | LaFleur | |
| 7,157,247 B2 | 1/2007 | Botstein | |
| 7,244,816 B2 | 7/2007 | Botstein | |
| 7,368,531 B2 | 5/2008 | Rosen | |
| 7,393,663 B2 | 7/2008 | Edwards | |
| 2003/0211096 A1 | 11/2003 | Ashkenazi | |
| 2017/0037124 A1 | 2/2017 | Gusarova | |
| 2017/0291937 A1 | 10/2017 | Gromada | |

FOREIGN PATENT DOCUMENTS

| | | |
|---|---|---|
| WO | 2016/054494 | 4/2016 |
| WO | 2017027316 A1 | 2/2017 |
| WO | 2017177181 A1 | 12/2017 |

OTHER PUBLICATIONS

Fu, Zhiyao, et al., "A lipasin/Angptl8 monoclonal antibody lowers mouse serum triglycerides involving increased postprandial activity of the cardiac lipoprotein lipase," Scientific Reports, vol. 5, No. 1, Dec. 21, 2015 XP55360939.
Zhang, Ren, "The ANGPTL3-4-8 model, a molecular mechanism for triglyceride trafficking," Open Biology, vol. 6, No. 1, Apr. 1, 2016, p. 150272, XP55387866.
Gusarova, Viktoria, et al., "ANGPTL8 Blockage with a Monoclonal Antibody Promotes Triglyceride Clearance, Energy Expenditure, and Weight Loss in Mice," Endocrinology, vol. 158, No. 5, May 1, 2017, pp. 1252-1259, XP055443231.
Haller, Jorge F., et al., "ANGPTL8 requires ANGPTL3 to inhibit lipoprotein lipase and plasma triglyceride clearance," Journal of Lipid Research, vol. 58, No. 6, Jun. 1, 2017 pp. 1166-1173, XP55387875.
Hanson, Robert L. et al., "The Arg59Trp variant in ANGPTL8 (betatrophin) is associated with total and HDL-cholesterol in American Indians and Mexican Americans and differentially affects cleavage of ANGPTL3," Molecular Genetics and Metabolism, Academic Press, Amsterdam, NL, vol. 118, No. 2, Apr. 19, 2016, pp. 128-137, XP029548394.
Ren (2012) Am J Physiol Endocrinol Metab 303:E334-E351 "Identification of RIFL, a novel adipocyte-enriched insulin target gene with a role in lipid metabolism".
Zhang (2012) Biochem Biophys Res Commun http://dx.doi.org/10.1016/j.bbrc.2012.07.038 "Lipasin, a novel nutritionally-regulated liver-enriched factor that regulates serum triglyceride levels".
International Search Report for International Application No. PCT/US2017/062103, from the European Patent Office dated Feb. 9, 2018.
Zhang et al., "Emerging Roles of Lipasin as a Critical Lipid Regulator", (2013) Biochemical and Biophysical Research Communications 432:401-405.
Arigobo Biolaboratories, "Product Data Sheet—Purified anti-Betatrophin (ANGPTL8)", (Jul. 25, 2014), BioLegend, URL:http://www.biolegend.com/pop_pdf?id=10113, (Nov. 8, 2016), XP002763965, 3 pages.
Product Data Sheet, "Purified anti-Betatrophin (ANGPTL8)", BioLegend, XP-002763965, Revision Date Jul. 25, 2014, 1 page.
Calandra et al., "Familial combined hypolipidemia due to mutations in the ANGPTL3 gene", Clinical Lipidology, 2013, 8: 1, 81-95.
Fenzl et al., "Circulating betatrophin correlates with atherogenic lipid profiles but not with glucose and insulin levels in insulin-resistant individuals", Diabetologia (2014), 57(6), 1204-1208.
Zhang et al., "A Monoclonal Neutralizing Antibody Against Lipasin (Angptl8), a Novel Lipid Regulator, Reduces Serum Triglycerides in Mice by Enhancing Lipoprotein Lipase-Mediated Triglyceride Clearance", Endocrine Society's 97th Annual Meeting and Expo,Mar. 5-8, 2015, San Diego, CA. Abstract# OR13-6, 1 page.
Nohara et al., "Impact of Betatrophin (ANGPTL8) R59W Mutation for Future Diabetes, and Minimal Modification of Circulating Betatrophin With Strong Statins", Circulation, (Nov. 10, 2015), vol. 132, Supp. Suppl. 3. Abstract No. 18157, 1 page.

*Primary Examiner* — Marianne P Allen

(57) ABSTRACT

The present invention provides antibodies that bind to ANGPTL8 and methods of using the same. According to certain embodiments, the invention includes methods of using anti-ANGPTL8 antibodies that bind human ANGPTL8 with high affinity to treat obesity, reduce body fat, reduce body weight, increase energy expenditure, and increase HDL-C, in a subject.

10 Claims, 22 Drawing Sheets

Specification includes a Sequence Listing.

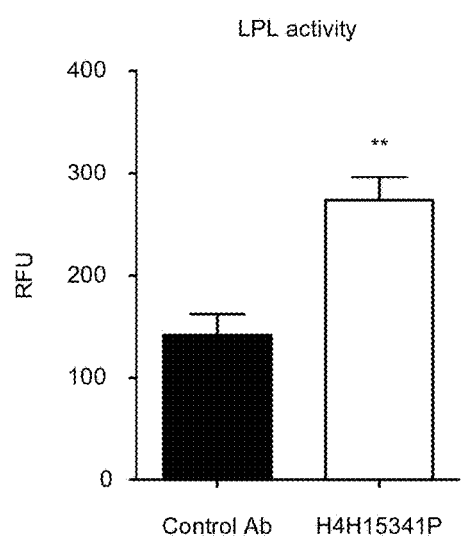 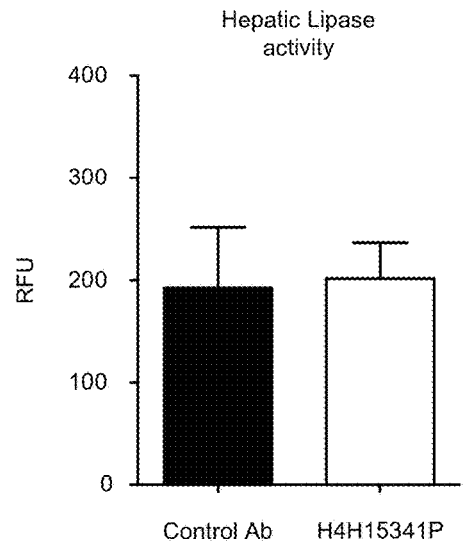
FIG. 3A  FIG. 3B
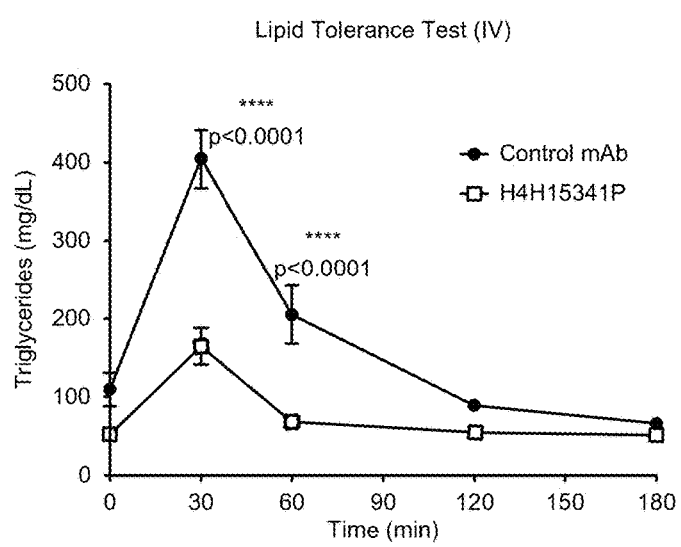
FIG. 4

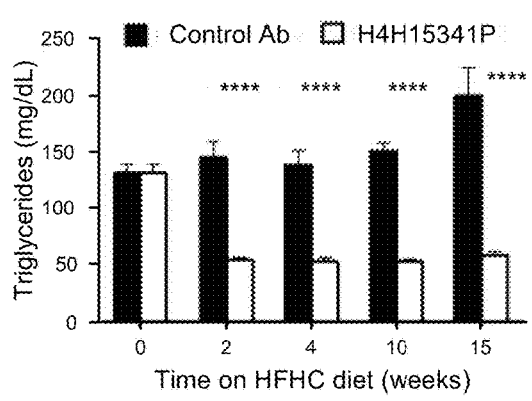
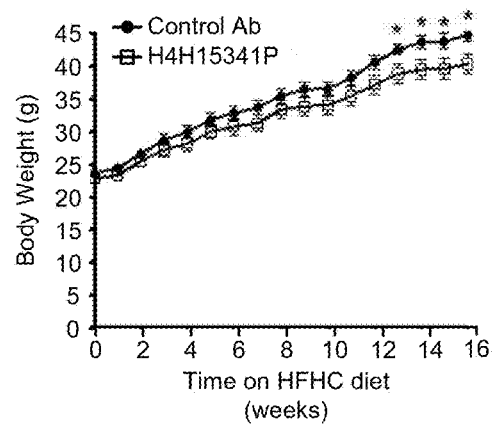
FIG. 7A
FIG. 7B
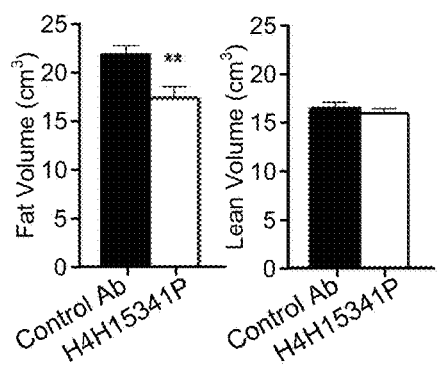
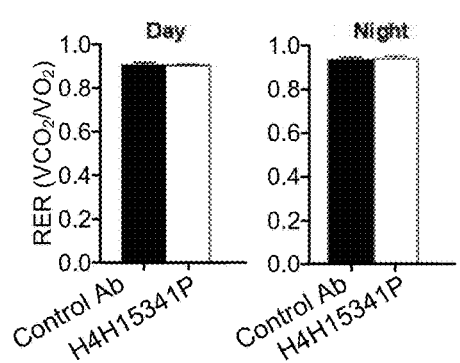
FIG. 7C
FIG. 7D

```
                           SEQUENCE LISTING

<160> NUMBER OF SEQ ID NOS: 368

<210> SEQ ID NO 1
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
caggtgcagc tggtgcagtc tggggctgag gtgaagaagc ctggggcctc agtgaaggtc      60
tcctgcaagg cttctggata caccttcacc agttatgata tcaattgggt gcgacaggcc     120
actggacaag ggcttgagtg gatggggtgg atgaaccta acggtgataa cacaggctat     180
gcacagaagt tccagggcag agtcaccatg accgggggaca cctccataag cacagcctac     240
atggagctga gcagcctgag atctgaggac acggccgtgt attactgtgc gagagaggga     300
atttgggggt tcgaccctg gggccaggga accctggtca ccgtctcctc a              351

<210> SEQ ID NO 2
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Gly Asp Asn Thr Gly Tyr Ala Gln Lys Phe
    50                  55                  60

Gln Gly Arg Val Thr Met Thr Gly Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Ile Trp Gly Phe Asp Pro Trp Gly Gln Gly Thr Leu
            100                 105                 110

Val Thr Val Ser Ser
        115

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggatacacct tcaccagtta tgat                                           24

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Tyr Thr Phe Thr Ser Tyr Asp
1               5

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
atgaacccta acggtgataa caca                                           24

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Met Asn Pro Asn Gly Asp Asn Thr
1               5

<210> SEQ ID NO 7
<211> LENGTH: 30
<212> TYPE: DNA
```

<213> ORGANISM: Artificial Sequence
<220> FEATURE:
<223> OTHER INFORMATION: Description of Artificial Sequence: Synthetic oligonucleotide

<400> SEQUENCE: 7
gcgagagagg gaatttgggg gttcgacccc                                      30

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 8

Ala Arg Glu Gly Ile Trp Gly Phe Asp Pro
1               5                   10

<210> SEQ ID NO 9
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9
gacatccaga tgacccagtc tccatcctcc ctgtctgcat ctgtaggaga cagagtcacc        60
atcacttgcc gggcaagtca ggacattaga aatgatttag ctggtatca gcagaaacca       120 gggaaagccc ctaagcgcct gatctatgct gcatccagtt tgcaaagtgg ggtcccatca      180
aggttcagcg gcagtggatc tgggacagaa ttcactctca caatcagcag cctgcagcct     240
gaagattttg caacttttta ctgtctacag cataatactt tccctcggac gttcggccaa     300
gggaccaagg tggaaatcaa a                                               321

<210> SEQ ID NO 10
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Phe Tyr Cys Leu Gln His Asn Thr Phe Pro Arg
                85                  90                  95

Thr Phe Gly Gln Gly Thr Lys Val Glu Ile Lys
            100                 105

```
<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
caggacatta gaaatgat                                                 18

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Asp Ile Arg Asn Asp
1               5

<210> SEQ ID NO 13
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13 gctgcatcc                                                            9

<210> SEQ ID NO 14
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Ala Ser
1

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ctacagcata atactttccc tcggacg                                       27

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Gln His Asn Thr Phe Pro Arg Thr
1               5
```

<210> SEQ ID NO 17
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
gaagtgcagc tggtggagtc tgggggaggc ttggtacagc ctggcaggtc cctgagactc    60
tcctgtgcag cctctggatt catctttgat gattatgaca tgcactgggt ccggcaagct   120
ccagggaagg gcctggagtg gtctcaggt attagttgga atagtggtag taaaggctat    180
gcggactctg tgaagggccg attcaccatc tccagagaca cgccaagaa ctccctgtat    240 ctgcaaatga acagtctgag agctgaggac acggccttgt attactgtac aaaagggccc   300
tgggactact ttgactactg gggccaggga accctggtca ccgtctcctc a            351
```

<210> SEQ ID NO 18
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ile Phe Asp Asp Tyr
            20                  25                  30

Asp Met His Trp Val Arg Gln Ala Pro Gly Lys Gly Leu Glu Trp Val
        35                  40                  45

Ser Gly Ile Ser Trp Asn Ser Gly Ser Lys Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Thr Lys Gly Pro Trp Asp Tyr Phe Asp Tyr Trp Gly Gln Gly Thr Leu
            100                 105                 110

Val Thr Val Ser Ser
        115
```

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19

```
ggattcatct ttgatgatta tgac                                            24
```

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 20

Gly Phe Ile Phe Asp Asp Tyr Asp
1               5

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
attagttgga atagtggtag taaa                                          24

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ile Ser Trp Asn Ser Gly Ser Lys
1               5

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
acaaaagggc cctgggacta ctttgactac                                    30

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Thr Lys Gly Pro Trp Asp Tyr Phe Asp Tyr
1               5                   10

<210> SEQ ID NO 25
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
gacatccaga tgacccagtc tccttccacc ctgtctgcat ctgtaggaga cagagtcacc    60
atcacttgcc gggccagtca gagtattagt agctggttgg cctggtatca gcagaaacca   120
gggaaagccc ctaagctcct gatctataag gcgtctagtt tagaaaatgg ggtcccatca   180
aggttcagcg gcagtggatc tgggacagaa ttcactctca ccatcagcag cctgcagcct   240

```
gatgattttg caacttatta ctgccaacag tataatagtt attcgtacac ttttggccag        300
gggaccaagc tggagatcaa a                                                  321
```

<210> SEQ ID NO 26
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Asn Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Tyr
                85                  90                  95

Thr Phe Gly Gln Gly Thr Lys Leu Glu Ile Lys
            100                 105
```

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27

```
cagagtatta gtagctgg                                                      18
```

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
Gln Ser Ile Ser Ser Trp
1               5
```

<210> SEQ ID NO 29
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29

```
aaggcgtct                                                                9
```

<210> SEQ ID NO 30

<210> SEQ ID NO 30
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Lys Ala Ser
1

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
caacagtata atagttattc gtacact                                        27

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Gln Tyr Asn Ser Tyr Ser Tyr Thr
1               5

<210> SEQ ID NO 33
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
caggtgcagc tggtggagtc tgggggaggc gtggtccagc ctggggaggtc cctgagactc     60 tcctgtacag cctccggatt caccttcgga aactttggca tacactgggt ccgccaggct    120
ccaggcaagg ggctggagtg ggtggcggtc atatcatatg atggaactga taaattctat    180
gcagaccccg tgaagggccg attcattatc tccagagaca attctatgaa cattctgtat    240
ctgcaaatga acagcctgag agctgaagac acggctgtat actattgtgc gaaagatggg    300
gaaatggaac tacggggata ctattactac tacggaatgg acgtctgggg ccaagggacc    360
acggtcaccg tctcctca                                                 378

<210> SEQ ID NO 34
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Gly Asn Phe

```
                    20                  25                  30
Gly Ile His Trp Val Arg Gln Ala Pro Gly Lys Gly Leu Glu Trp Val
            35                  40                  45

Ala Val Ile Ser Tyr Asp Gly Thr Asp Lys Phe Tyr Ala Asp Pro Val
        50                  55                  60

Lys Gly Arg Phe Ile Ile Ser Arg Asp Asn Ser Met Asn Ile Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Glu Met Glu Leu Arg Gly Tyr Tyr Tyr Tyr Tyr Gly
            100                 105                 110

Met Asp Val Trp Gly Gln Gly Thr Thr Val Thr Val Ser Ser
        115                 120                 125
```

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ggattcacct tcggaaactt tggc                                           24

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Phe Thr Phe Gly Asn Phe Gly
1               5

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
atatcatatg atggaactga taaa                                           24

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ile Ser Tyr Asp Gly Thr Asp Lys
1               5

<210> SEQ ID NO 39
<211> LENGTH: 57
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 39
gcgaaagatg gggaaatgga actacgggga tactattact actacggaat ggacgtc        57

<210> SEQ ID NO 40
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Lys Asp Gly Glu Met Glu Leu Arg Gly Tyr Tyr Tyr Tyr Gly
1               5                   10                  15

Met Asp Val

<210> SEQ ID NO 41
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
gacatccaga tgacccagtc tccatcttcc gtgtctgcat ctgttggaga cagagtcacc        60
attacttgtc gggcgagtca gggtattaac acctggttag cctggtatca gcagaaacca       120
gggacagccc caaagctcct gatctttgct gcatccagtt tggagagcgg agtcccatca       180
aggttcagcg gcagtggatt tggtacagat ttcactctca ccatcagcag cctacagtct       240
gaggatcttg caacttactt ttgtcaacag gttcacagtc ccccgtacac ttttggccag       300
gggaccaagc tggagatcaa a                                                 321

<210> SEQ ID NO 42
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asn Thr Trp
            20                  25                  30

Leu Ala Trp Tyr Gln Gln Lys Pro Gly Thr Ala Pro Lys Leu Leu Ile
        35                  40                  45

Phe Ala Ala Ser Ser Leu Glu Ser Gly Val Pro Ser Arg Phe Ser Gly
    50                  55                  60

Ser Gly Phe Gly Thr Asp Phe Thr Leu Thr Ile Ser Ser Leu Gln Ser
65                  70                  75                  80

Glu Asp Leu Ala Thr Tyr Phe Cys Gln Gln Val His Ser Pro Pro Tyr
                85                  90                  95

Thr Phe Gly Gln Gly Thr Lys Leu Glu Ile Lys
            100                 105
```

```
<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
cagggtatta acacctgg                                                      18

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Gly Ile Asn Thr Trp
1               5

<210> SEQ ID NO 45
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45 gctgcatcc                                                                 9

<210> SEQ ID NO 46
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ala Ala Ser
1

<210> SEQ ID NO 47
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
caacaggttc acagtccccc gtacact                                            27

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Gln Val His Ser Pro Pro Tyr Thr
```

<210> SEQ ID NO 49
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 49

```
gaggtgcagc tggtggagtc tggaggaggt gtggtacggc cggggggggtc actgagactc      60
tcctgtgctg cctctggatt caccgttgat gattatgaca tgagttgggt ccgccaaact     120
ccaggaaagg ggctggagtg gatctctggc attaattgga atggaggtaa cacaggttat     180
gcagactctg tgaagggccg attcatcatc tccagagaca cgccaagaa ctccctgttt      240
ctgcaaatga acagtctgag agccgaggac acggccttgt atcactgttg gggagcgatt     300
ggtgcttttg atatttgggg ccaagggaca atggtcaccg tctcttca                  348
```

<210> SEQ ID NO 50
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 50

```
Glu Val Gln Leu Val Glu Ser Gly Gly Gly Val Val Arg Pro Gly Gly
1               5                   10                  15
Ser Leu Arg Leu Ser Cys Ala Ala Ser Gly Phe Thr Val Asp Asp Tyr
            20                  25                  30
Asp Met Ser Trp Val Arg Gln Thr Pro Gly Lys Gly Leu Glu Trp Ile
        35                  40                  45
Ser Gly Ile Asn Trp Asn Gly Gly Asn Thr Gly Tyr Ala Asp Ser Val
    50                  55                  60
Lys Gly Arg Phe Ile Ile Ser Arg Asp Ser Ala Lys Asn Ser Leu Phe
65                  70                  75                  80
Leu Gln Met Asn Ser Leu Arg Ala Glu Asp Thr Ala Leu Tyr His Cys
                85                  90                  95
Trp Gly Ala Ile Gly Ala Phe Asp Ile Trp Gly Gln Gly Thr Met Val
            100                 105                 110
Thr Val Ser Ser
        115
```

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 51

```
ggattcaccg ttgatgatta tgac                                              24
```

<210> SEQ ID NO 52
<211> LENGTH: 8
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 52

Gly Phe Thr Val Asp Asp Tyr Asp
1               5

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
attaattgga atggaggtaa caca                                              24

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ile Asn Trp Asn Gly Gly Asn Thr
1               5

<210> SEQ ID NO 55
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
tggggagcga ttggtgcttt tgatatt                                           27

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Trp Gly Ala Ile Gly Ala Phe Asp Ile
1               5

<210> SEQ ID NO 57
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
gatattgtga tgacccagtc tccactctcc tcacctgtca cccttggaca gccggcctcc       60
atctcctgca ggtctagtca aagcctcgta cacagtgatg gcggcaccta cttgagttgg      120
cttcagcaga ggccaggcca gcctccaaga ctcctaattt ataagatttt taaccggttc      180
```

```
tctggggtcc cagacagatt cagtggcagt ggggcaggga cagatttcac actgagaatc    240
agtagggtgg aagctgagga tgtcggggtt tattactgca tgcaaacaac acaatttccg    300
ctcactttcg gcggagggac caaggtggag atcaaa                              336
```

<210> SEQ ID NO 58  
<211> LENGTH: 112  
<212> TYPE: PRT  
<213> ORGANISM: Artificial Sequence  
<220> FEATURE:  
<223> OTHER INFORMATION: Description of Artificial Sequence: Synthetic
      polypeptide

<400> SEQUENCE: 58

```
Asp Ile Val Met Thr Gln Ser Pro Leu Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Gly Thr Tyr Leu Ser Trp Leu Gln Gln Arg Pro Gly Gln Pro
        35                  40                  45

Pro Arg Leu Leu Ile Tyr Lys Ile Phe Asn Arg Phe Ser Gly Val Pro
    50                  55                  60

Asp Arg Phe Ser Gly Ser Gly Ala Gly Thr Asp Phe Thr Leu Arg Ile
65                  70                  75                  80

Ser Arg Val Glu Ala Glu Asp Val Gly Val Tyr Tyr Cys Met Gln Thr
                85                  90                  95

Thr Gln Phe Pro Leu Thr Phe Gly Gly Gly Thr Lys Val Glu Ile Lys
            100                 105                 110
```

<210> SEQ ID NO 59  
<211> LENGTH: 33  
<212> TYPE: DNA  
<213> ORGANISM: Artificial Sequence  
<220> FEATURE:  
<223> OTHER INFORMATION: Description of Artificial Sequence: Synthetic
      oligonucleotide

<400> SEQUENCE: 59

```
caaagcctcg tacacagtga tggcggcacc tac                                 33
```

<210> SEQ ID NO 60  
<211> LENGTH: 11  
<212> TYPE: PRT  
<213> ORGANISM: Artificial Sequence  
<220> FEATURE:  
<223> OTHER INFORMATION: Description of Artificial Sequence: Synthetic
      peptide

<400> SEQUENCE: 60

```
Gln Ser Leu Val His Ser Asp Gly Gly Thr Tyr
1               5                   10
```

<210> SEQ ID NO 61  
<211> LENGTH: 9  
<212> TYPE: DNA  
<213> ORGANISM: Artificial Sequence  
<220> FEATURE:  
<223> OTHER INFORMATION: Description of Artificial Sequence: Synthetic
      oligonucleotide

<400> SEQUENCE: 61

```
aagattttt                                                            9
```

<210> SEQ ID NO 62
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 62

Lys Ile Phe
1

<210> SEQ ID NO 63
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 63
atgcaaacaa cacaatttcc gctcact                                          27

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 64

Met Gln Thr Thr Gln Phe Pro Leu Thr
1               5

<210> SEQ ID NO 65
<211> LENGTH: 345
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 65
gaggtgcagc tggtggagtc tgggggaggc ttggtacagc ctggggggtc cctgagactc       60
tcctgtgcag cctctggatt cacctttagc agctatgcca tgagctgggt ccgccaggct      120
ccagggaagg ggctggagtg ggtctcagct attactggta gtggtggtag aacatactac      180
gcagactccg tgaagggccg gttcaccatc tccagagaca atgccaagaa cacgctgtat      240
ctgcaaatga acagcctgag agccgaggac acggccgtat attactgtgc gaaaaacttt      300 cccttttgact actggggcca gggaaccctg gtcaccgtct cctca                     345

<210> SEQ ID NO 66
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
         35                  40                  45

Ser Ala Ile Thr Gly Ser Gly Gly Arg Thr Tyr Tyr Ala Asp Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asn Phe Pro Phe Asp Tyr Trp Gly Gln Gly Thr Leu Val Thr
            100                 105                 110

Val Ser Ser
        115

<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
ggattcacct ttagcagcta tgcc                                              24

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gly Phe Thr Phe Ser Ser Tyr Ala
 1               5

<210> SEQ ID NO 69
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
attactggta gtggtggtag aaca                                              24

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ile Thr Gly Ser Gly Gly Arg Thr
 1               5

<210> SEQ ID NO 71
<211> LENGTH: 24
<212> TYPE: DNA
<213> ORGANISM: Artificial Sequence
<220> FEATURE:

<223> OTHER INFORMATION: Description of Artificial Sequence: Synthetic
oligonucleotide

<400> SEQUENCE: 71
gcgaaaaact ttccctttga ctac                                                24

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 72

Ala Lys Asn Phe Pro Phe Asp Tyr
1               5

<210> SEQ ID NO 73
<211> LENGTH: 339
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 73
gacatcgtga tgacccagtc tccagactcc ctggctgtgt ctctgggcga gagggccacc         60
atcaactgcg agtccagcca gagtgtttta tacagctcca acaataagaa ctacttagct        120
tggtaccagc agaaaccagg acagcctcct aagctgctca tttactgggc atctacccgg        180
gaatccgggg tccctgaccg attcagtggc agcgggtctg ggacagattt cactctcacc        240
atcagcaccc tgcaggctga ggatgtggca gtttattact gtcagcaata ttatagtact        300
ccgtacactt ttggccaggg gaccaagctg gagatcaaa                               339

<210> SEQ ID NO 74
<211> LENGTH: 113
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 74

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Thr Leu Gln Ala Glu Asp Val Ala Val Tyr Tyr Cys Gln Gln
                85                  90                  95

Tyr Tyr Ser Thr Pro Tyr Thr Phe Gly Gln Gly Thr Lys Leu Glu Ile
            100                 105                 110

Lys

```
<210> SEQ ID NO 75
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
cagagtgttt tatacagctc caacaataag aactac                              36

<210> SEQ ID NO 76
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gln Ser Val Leu Tyr Ser Ser Asn Asn Lys Asn Tyr
1               5                   10

<210> SEQ ID NO 77
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77 tgggcatct                                                             9

<210> SEQ ID NO 78
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Trp Ala Ser
1

<210> SEQ ID NO 79
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
cagcaatatt atagtactcc gtacact                                        27

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gln Gln Tyr Tyr Ser Thr Pro Tyr Thr
1               5
```

<210> SEQ ID NO 81
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81
gaggtgcagc tggtggagtc tgggggaggc ttggtacagc ctgggggtc cctgagactc      60 tcctgtgcag cctctggatt cacctttcc agctatgcca tgacctgggt ccgccaggct     120
ccagggaagg ggctggagtg ggtctcagct attagtggta gtggtggtag cacatactac     180
acagactccg tgaagggccg gttcaccctc tccagagaca attccaagaa cacgctgtat     240
ctgcaaatga acagcctgag agccgaggac acggccgtat attactgtgc gaaatctgac     300
tacagtaaca ccatctactg gtactacggt atggacgtct ggggccaagg gaccacggtc     360
accgtctcct ca                                                        372

<210> SEQ ID NO 82
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Glu Trp Val
        35                  40                  45

Ser Ala Ile Ser Gly Ser Gly Gly Ser Thr Tyr Tyr Thr Asp Ser Val
    50                  55                  60

Lys Gly Arg Phe Thr Leu Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Asp Tyr Ser Asn Thr Ile Tyr Trp Tyr Tyr Gly Met Asp
            100                 105                 110

Val Trp Gly Gln Gly Thr Thr Val Thr Val Ser Ser
        115                 120

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
ggattcacct tttccagcta tgcc                                            24

<210> SEQ ID NO 84
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 84

Gly Phe Thr Phe Ser Ser Tyr Ala
1               5

<210> SEQ ID NO 85
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
attagtggta gtggtggtag caca                                              24

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ile Ser Gly Ser Gly Gly Ser Thr
1               5

<210> SEQ ID NO 87
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
gcgaaatctg actacagtaa caccatctac tggtactacg gtatggacgt c                51

<210> SEQ ID NO 88
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ala Lys Ser Asp Tyr Ser Asn Thr Ile Tyr Trp Tyr Tyr Gly Met Asp
1               5                   10                  15

Val

<210> SEQ ID NO 89
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89
gacatccaga tgacccagtc tccatcctcc ctgtctgcat ctgtaggaga cagagtcacc        60
atcacttgcc gggcaagtca gagcattagc agctatttaa attggtatca gcagaaacca      120
```

```
gggaaagccc ctaagctcct gatctatgct gcatccagtt tgcaaagtgg ggtcccatca    180
aggttcagtg gcagtgggtc tgggacagat ttcactctca ccatcagcag tctgcaacct    240
gaagattttg caacttacta ctgtcaacag agttacagta ccccctcggac gttcggccaa    300 gggaccaagg tggaaatcaa a                                              321
```

<210> SEQ ID NO 90
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95

Thr Phe Gly Gln Gly Thr Lys Val Glu Ile Lys
            100                 105
```

<210> SEQ ID NO 91
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91

```
cagagcatta gcagctat                                                  18
```

<210> SEQ ID NO 92
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

```
Gln Ser Ile Ser Ser Tyr
1               5
```

<210> SEQ ID NO 93
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93

```
gctgcatcc                                                                    9
```

<210> SEQ ID NO 94
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ala Ala Ser
1

<210> SEQ ID NO 95
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95

```
caacagagtt acagtacccc tcggacg                                               27
```

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gln Gln Ser Tyr Ser Thr Pro Arg Thr
1               5

<210> SEQ ID NO 97
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97

```
caggtgcagc tggtggagtc tgggggaggc ttggtcaagc ctggagggtc cctgagactc          60
tcctgtgcag cctctggatt caccttcagt gactactata tgagctggat ccgccaggct         120
ccagggaagg gactggagtg gatttcacac attagtggta gtggtagaac cacacactac         180
gcagactcta tgaagggccg attcaccatt tccagggaca acgccaagaa ctcactgtat         240
ttgcaaatga acagcctgag agccgaggac acggccgtgt attactgtgt gagagaggga         300
ggttttaact ggaactacga gggtactttt gatatctggg gccagggac aatggtcacc          360 gtctcttca                                                                369
```

<210> SEQ ID NO 98
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Ile
        35                  40                  45

Ser His Ile Ser Gly Ser Gly Arg Thr Thr His Tyr Ala Asp Ser Met
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Glu Gly Gly Phe Asn Trp Asn Tyr Glu Gly Thr Phe Asp Ile
            100                 105                 110

Trp Gly Gln Gly Thr Met Val Thr Val Ser Ser
        115                 120
```

<210> SEQ ID NO 99
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
ggattcacct tcagtgacta ctat                                              24

<210> SEQ ID NO 100
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

```
Gly Phe Thr Phe Ser Asp Tyr Tyr
1               5
```

<210> SEQ ID NO 101
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
attagtggta gtggtagaac caca                                              24

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

```
Ile Ser Gly Ser Gly Arg Thr Thr
1               5
```

<210> SEQ ID NO 103
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 103
gtgagagagg gaggttttaa ctggaactac gagggtactt ttgatatc                    48

<210> SEQ ID NO 104
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 104

Val Arg Glu Gly Gly Phe Asn Trp Asn Tyr Glu Gly Thr Phe Asp Ile
1               5                   10                  15

<210> SEQ ID NO 105
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 105
gatattgtga tgacccagac tccactctct tcacctgtca cccttggaca gccggcctcc       60
atctcctgca ggtctagtca agcctcttta cacagtgatc aaaacaccta cttgagttgg     120
cttcaccaga ggccaggcca gcctccaaga ctcctaattt ataagatttc taaccggttc     180
tctggggtcc cagacagatt cagtggcagt ggggcaggga cagtttcac actgaaaatc      240 agcagggtgg aagctgagga tgtcgggatt tattactgca tgcaaggtac acaatttccg     300
ctcactttcg gcggagggac caaggtggag atcaaa                                336

<210> SEQ ID NO 106
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 106

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Leu His Ser
            20                  25                  30

Asp Gln Asn Thr Tyr Leu Ser Trp Leu His Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Ile Tyr Tyr Cys Met Gln Gly
                85                  90                  95

Thr Gln Phe Pro Leu Thr Phe Gly Gly Gly Thr Lys Val Glu Ile Lys

<210> SEQ ID NO 107
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
caaagcctct tacacagtga tcaaaacacc tac                           33

<210> SEQ ID NO 108
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gln Ser Leu Leu His Ser Asp Gln Asn Thr Tyr
1               5                   10

<210> SEQ ID NO 109
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109 aagatttct                                                      9

<210> SEQ ID NO 110
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Lys Ile Ser
1

<210> SEQ ID NO 111
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
atgcaaggta cacaatttcc gctcact                                  27

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Met Gln Gly Thr Gln Phe Pro Leu Thr
1               5

<210> SEQ ID NO 113
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113
gaggtgcagc tggtggagtc tgggggaggc ttggtacagg ggggggggtc cctgagactc    60
tcctgtgaag cctctggatt cacatttagc agctttgcca tgaactgggt ccgccaggct   120
ccagggaagg ggctggagtg gtctcaggt cttagtggta gtggtagaag tacatactac   180
gcagactccg tgaagggccg gttcaccatc tccagagaca actccaagaa tagactctat   240
ttgcaaatgg acagcctgag agccgaggac tcggccgtat attattgtgc ggcctacgtg   300
ttacgaattt tggatcggtg gttcgacccc tggggccagg gaaccctggt caccgtctcc   360
tca                                                                363

<210> SEQ ID NO 114
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Glu Val Gln Leu Val Glu Ser Gly Gly Arg Leu Gly Thr Gly Gly
1               5                   10                  15

Ser Leu Arg Leu Ser Cys Glu Ala Ser Gly Phe Thr Phe Ser Ser Phe
            20                  25                  30

Ala Met Asn Trp Val Arg Gln Ala Pro Gly Lys Gly Leu Glu Trp Val
        35                  40                  45

Ser Gly Leu Ser Gly Ser Gly Arg Ser Thr Tyr Tyr Ala Asp Ser Val
    50                  55                  60

Lys Gly Arg Phe Thr Ile Ser Arg Asp Asn Ser Lys Asn Arg Leu Tyr
65                  70                  75                  80

Leu Gln Met Asp Ser Leu Arg Ala Glu Asp Ser Ala Val Tyr Tyr Cys
                85                  90                  95

Ala Ala Tyr Val Leu Arg Ile Leu Asp Arg Trp Phe Asp Pro Trp Gly
            100                 105                 110

Gln Gly Thr Leu Val Thr Val Ser Ser
        115                 120

<210> SEQ ID NO 115
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
ggattcacat ttagcagctt tgcc                                          24

<210> SEQ ID NO 116

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gly Phe Thr Phe Ser Ser Phe Ala
1               5

<210> SEQ ID NO 117
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
cttagtggta gtggtagaag taca                                            24

<210> SEQ ID NO 118
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Leu Ser Gly Ser Gly Arg Ser Thr
1               5

<210> SEQ ID NO 119
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
gcggcctacg tgttacgaat tttggatcgg tggttcgacc cc                         42

<210> SEQ ID NO 120
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Ala Ala Tyr Val Leu Arg Ile Leu Asp Arg Trp Phe Asp Pro
1               5                   10

<210> SEQ ID NO 121
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 121
gatattgtga tgactcagtc tccactctcc ctgcccgtca cccctggaga gccggcctcc      60
```

```
atctcctgca ggtctagtca gagcctcctt cataggactg gatacaacta tttggactgg    120
tacctgcaga agccagggca gtctccacag atcctgatct atttgggttc ttatcgggcc    180 tccgggtcc ctgacaggtt cagtggcagt ggatcaggca cagattttac actgaagatc     240
agcagagtgg aggctgaaga tgttgggggtt tattactgca tgcaagctct acaaactccg    300
tggacgttcg gccaagggac caaggtggaa atcaaa                               336
```

```
<210> SEQ ID NO 122
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122
```

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Arg
            20                  25                  30

Thr Gly Tyr Asn Tyr Leu Asp Trp Tyr Leu Gln Lys Pro Gly Gln Ser
        35                  40                  45

Pro Gln Ile Leu Ile Tyr Leu Gly Ser Tyr Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110
```

```
<210> SEQ ID NO 123
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
cagagcctcc ttcataggac tggatacaac tat                                  33
```

```
<210> SEQ ID NO 124
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124
```

```
Gln Ser Leu Leu His Arg Thr Gly Tyr Asn Tyr
1               5                   10
```

```
<210> SEQ ID NO 125
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
``` ttgggttct                                                              9

<210> SEQ ID NO 126
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Leu Gly Ser
1

<210> SEQ ID NO 127
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
atgcaagctc tacaaactcc gtggacg                                         27

<210> SEQ ID NO 128
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Met Gln Ala Leu Gln Thr Pro Trp Thr
1               5

<210> SEQ ID NO 129
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 129
caggtgcagc tgcaggagtc gggcccagga ctggtgaagc cttcacagac cctgtccctc     60
acctgcactg tctctggtgg ctccatcaac agtggtggtt actactggaa ctggatccgc    120
cagcacccag ggaagggcct ggagtggatt gggtacatct attacagtgg gagcacctac    180
ttcaacccgt ccctcaagag tcgagttacc atatcaatag acacgtctaa gaaccagttc    240
tccctgaagc tgagctctgt gactgccgcg gacacggccg tgtattactg tgcgagagag    300
gggatttatg cttttgacta ctggggccag ggaaccctgg tcaccgtctc ctca          354

<210> SEQ ID NO 130
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Gln Val Gln Leu Gln Glu Ser Gly Pro Gly Leu Val Lys Pro Ser Gln

```
1               5                  10                 15
Thr Leu Ser Leu Thr Cys Thr Val Ser Gly Gly Ser Ile Asn Ser Gly
            20                  25                 30

Gly Tyr Tyr Trp Asn Trp Ile Arg Gln His Pro Gly Lys Gly Leu Glu
        35                  40                 45

Trp Ile Gly Tyr Ile Tyr Tyr Ser Gly Ser Thr Tyr Phe Asn Pro Ser
    50                  55                 60

Leu Lys Ser Arg Val Thr Ile Ser Ile Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Ile Tyr Ala Phe Asp Tyr Trp Gly Gln Gly Thr
            100                 105                110

Leu Val Thr Val Ser Ser
        115
```

<210> SEQ ID NO 131
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
ggtggctcca tcaacagtgg tggttactac                                    30

<210> SEQ ID NO 132
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

```
Gly Gly Ser Ile Asn Ser Gly Gly Tyr Tyr
1               5                  10
```

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
atctattaca gtgggagcac c                                             21

<210> SEQ ID NO 134
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

```
Ile Tyr Tyr Ser Gly Ser Thr
1               5
```

<210> SEQ ID NO 135

```
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
gcgagagagg ggatttatgc ttttgactac                                        30

<210> SEQ ID NO 136
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Ala Arg Glu Gly Ile Tyr Ala Phe Asp Tyr
1               5                   10

<210> SEQ ID NO 137
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 137
gacatccaga tgacccagtc tccatcctcc ctgtctgcat ctgtaggaga cagagtcacc        60
atcacttgcc gggcaagtca gggcattaga aatgatttag ctggtatca gcagaaacca       120 gggaaagccc ctaagcgcct gatctattct gcatccagtt tgcaaagtgg ggtcccatca      180
aggttcggcg gcagtggatc tgggacagaa ttcactctca caatcagcag cctgcagcct      240
gaagattttg caacttatta ctgtctacaa cataatagtt acccgtggac gttcggccaa      300
gggaccaagg tggaaatcaa a                                                 321

<210> SEQ ID NO 138
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ser Ala Ser Ser Leu Gln Ser Gly Val Pro Ser Arg Phe Gly Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105
```

<210> SEQ ID NO 139
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
cagggcatta gaaatgat                                                     18

<210> SEQ ID NO 140
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Gln Gly Ile Arg Asn Asp
1               5

<210> SEQ ID NO 141
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141 tctgcatcc                                                                9

<210> SEQ ID NO 142
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Ser Ala Ser
1

<210> SEQ ID NO 143
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
ctacaacata atagttaccc gtggacg                                           27

<210> SEQ ID NO 144
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

```
Leu Gln His Asn Ser Tyr Pro Trp Thr
1               5
```

<210> SEQ ID NO 145
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 145

```
caggtgcagc tggtggagtc tgggggaggc gtggtccagc ctgggaggtc cctgagactc    60
tcctgtgcag cctctggatt caccttcaat aactatggca tacactgggt ccgccaggct   120
ccaggcaagg ggctggagtg ggtggcagtt atatcatatg atgaaagtaa taaatactat   180
gcagactccg tgaagggccg attcaccatc tccagagaca attccaagaa cacgctgtat   240
ctgcaaatga acagcctgag agctgaggac acggctgttt attactgtgc gaaagacata   300
cggatagcag ctcgtcggca ctactactac tacggtatgg acgtctgggg ccaagggacc   360
acggtcaccg tctcctca                                                 378
```

<210> SEQ ID NO 146
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asn Asn Tyr
            20                  25                  30

Gly Ile His Trp Val Arg Gln Ala Pro Gly Lys Gly Leu Glu Trp Val
        35                  40                  45

Ala Val Ile Ser Tyr Asp Glu Ser Asn Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Arg Ile Ala Ala Arg Arg His Tyr Tyr Tyr Gly
            100                 105                 110

Met Asp Val Trp Gly Gln Gly Thr Thr Val Thr Val Ser Ser
        115                 120                 125
```

<210> SEQ ID NO 147
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147

```
ggattcacct tcaataacta tggc                                           24
```

<210> SEQ ID NO 148
<211> LENGTH: 8

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gly Phe Thr Phe Asn Asn Tyr Gly
1               5

<210> SEQ ID NO 149
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
atatcatatg atgaaagtaa taaa                                              24

<210> SEQ ID NO 150
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Ile Ser Tyr Asp Glu Ser Asn Lys
1               5

<210> SEQ ID NO 151
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
gcgaaagaca tacggatagc agctcgtcgg cactactact actacggtat ggacgtc         57

<210> SEQ ID NO 152
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Ala Lys Asp Ile Arg Ile Ala Ala Arg Arg His Tyr Tyr Tyr Tyr Gly
1               5                   10                  15

Met Asp Val

<210> SEQ ID NO 153
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 153
gacatccaga tgacccagtc tccatcttcc gtgtctgcat ctgtaggaga cagagtcacc      60
```

```
atcacttgtc gggcgagtca gggtattagc aggtggttag cctggtatca gcagaaacca    120
gggaaagccc caaagctcct gatctatgct gcatccagtt tggaaagtgg ggtcccagca    180
aggttcagcg gcagtggatc tgggacagat ttcactctca ccatcagcag cctgcagcct    240
gaagattttg caacttacta ttgtcaacag gctaacagtt tcccaatcac tttcggccct    300
gggaccaaag tggatatcaa a                                              321
```

<210> SEQ ID NO 154
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Arg Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Glu Ser Gly Val Pro Ala Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Pro Gly Thr Lys Val Asp Ile Lys
            100                 105
```

<210> SEQ ID NO 155
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155

```
cagggtatta gcaggtgg                                                   18
```

<210> SEQ ID NO 156
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

```
Gln Gly Ile Ser Arg Trp
1               5
```

<210> SEQ ID NO 157
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 157 gctgcatcc                                                            9

<210> SEQ ID NO 158
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Ala Ala Ser
1

<210> SEQ ID NO 159
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
caacaggcta acagtttccc aatcact                                       27

<210> SEQ ID NO 160
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Gln Gln Ala Asn Ser Phe Pro Ile Thr
1               5

<210> SEQ ID NO 161
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 161
gaggtgcagc tggtggagtc tgggggaggc ttggtacagc ctggagggtc cctgagactc    60
tcctgtgcag cctctggatt caccttcaat aatcatgaaa tgaattgggt ccgccaggct   120
ccagggaagg gtctggagtg ggtttcatac attagtagta gtggtaatac cgtaacctac   180
gcagactttc tgaagggccg attcaccatc tccagagaca acgccaagaa ctcgctgttt   240
ctgcaaatga acagcctgcg agacgaggac acggctgttt attactgtgc gcgagatcat   300
ttaagtggaa cctccccact ttcttattgg ggccagggaa ccctggtcac cgtctcctca   360

<210> SEQ ID NO 162
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn His
            20                  25                  30

Glu Met Asn Trp Val Arg Gln Ala Pro Gly Lys Gly Leu Glu Trp Val
        35                  40                  45

Ser Tyr Ile Ser Ser Ser Gly Asn Thr Val Thr Tyr Ala Asp Phe Leu
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Asp Glu Asp Thr Ala Val Tyr Tyr Cys
                85                  90                  95

Ala Arg Asp His Leu Ser Gly Thr Ser Pro Leu Ser Tyr Trp Gly Gln
            100                 105                 110

Gly Thr Leu Val Thr Val Ser Ser
        115                 120

<210> SEQ ID NO 163
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
ggattcacct tcaataatca tgaa                                              24

<210> SEQ ID NO 164
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Gly Phe Thr Phe Asn Asn His Glu
1               5

<210> SEQ ID NO 165
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
attagtagta gtggtaatac cgta                                              24

<210> SEQ ID NO 166
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Ile Ser Ser Ser Gly Asn Thr Val
1               5

<210> SEQ ID NO 167
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
gcgcgagatc atttaagtgg aacctcccca ctttcttat                              39

<210> SEQ ID NO 168
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Ala Arg Asp His Leu Ser Gly Thr Ser Pro Leu Ser Tyr
1               5                   10

<210> SEQ ID NO 169
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 169
gacatccaga tgacccagtc tccatcctcc ctgtctgcat ctgtgggaga cagagtcacc        60
atcacttgcc aggcgagtca ggacattaac aactacttaa attggtttca gcagaaacca       120
gggaaagccc ctaaactcct gatcttcgat gcatccaatt tagaaacagg ggtcccatca       180
aggttcagtg aagtggatc tgggacagat tttactttca ccatcagcag cctgcagcct       240
gaagatattg caacatattt ctgtcaacag tatgaaaatc tcccttacac ttttggccag       300
gggaccaagc tggagatcaa a                                                 321

<210> SEQ ID NO 170
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Asn Tyr
            20                  25                  30

Leu Asn Trp Phe Gln Gln Lys Pro Gly Lys Ala Pro Lys Leu Leu Ile
        35                  40                  45

Phe Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Tyr Glu Asn Leu Pro Tyr
                85                  90                  95

Thr Phe Gly Gln Gly Thr Lys Leu Glu Ile Lys
            100                 105

<210> SEQ ID NO 171
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
caggacatta acaactac                                                 18

<210> SEQ ID NO 172
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Gln Asp Ile Asn Asn Tyr
1               5

<210> SEQ ID NO 173
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173 gatgcatcc                                                            9

<210> SEQ ID NO 174
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Asp Ala Ser
1

<210> SEQ ID NO 175
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
caacagtatg aaaatctccc ttacact                                       27

<210> SEQ ID NO 176
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

```
Gln Gln Tyr Glu Asn Leu Pro Tyr Thr
1               5
```

<210> SEQ ID NO 177
<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 177

```
caggtgcagc tggtggagtc tgggggaggc gtggtccagc ctggggaggtc cctgagactc     60 tcctgtgcag cctctggatt caccttcagt agctatggca tgcactgggt ccgccaggct    120
ccaggcaagg ggctggagtg gtggcagtt atatcatatg ctggaagtaa taaatactat    180
gcagactccg tgaagggccg attcaccatc tccagagaca attccaagaa cacgctgtat    240
ctgcaaatga acggcctgag agctgaggac acggctgtgt attactgtgc gaaagatccc    300
tacggtgact acgaggggt tcttgactac tggggccagg aaccctggt caccgtctcc    360 tca                                                                 363
```

<210> SEQ ID NO 178
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 178

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Ala Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Gly Leu Arg Ala Glu Asp Thr Ala Val Tyr Tyr Cys
                85                  90                  95

Ala Lys Asp Pro Tyr Gly Asp Tyr Glu Gly Val Leu Asp Tyr Trp Gly
            100                 105                 110

Gln Gly Thr Leu Val Thr Val Ser Ser
        115                 120
```

<210> SEQ ID NO 179
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 179

```
ggattcacct tcagtagcta tggc                                           24
```

<210> SEQ ID NO 180

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Gly Phe Thr Phe Ser Ser Tyr Gly
1               5

<210> SEQ ID NO 181
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
atatcatatg ctggaagtaa taaa                                            24

<210> SEQ ID NO 182
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Ile Ser Tyr Ala Gly Ser Asn Lys
1               5

<210> SEQ ID NO 183
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
gcgaaagatc cctacggtga ctacgagggg gttcttgact ac                        42

<210> SEQ ID NO 184
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Ala Lys Asp Pro Tyr Gly Asp Tyr Glu Gly Val Leu Asp Tyr
1               5                   10

<210> SEQ ID NO 185
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 185
gacatccaga tgacccagtc tccatcctcc ctgtctgcat ctgtaggaga cagagtcacc     60
```

```
atcacttgcc aggcgagtca ggacattagc aactatttaa attggtatca gcagaaacca    120
gggaaagccc ctaagctcct gatctacgat gcttccaatt tggaaacagg ggtcccatca    180
aggttcagtg gaagtggatc tgggacagat tttactttca ccatcagcag cctgcagcct    240
gaagatattg caacatatta ctgtcagcag tatgatcatc tcccgatcac cttcggccaa    300
gggacacgac tggagattaa a                                              321
```

<210> SEQ ID NO 186
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp His Leu Pro Ile
                85                  90                  95

Thr Phe Gly Gln Gly Thr Arg Leu Glu Ile Lys
            100                 105
```

<210> SEQ ID NO 187
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187

```
caggacatta gcaactat                                                   18
```

<210> SEQ ID NO 188
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

```
Gln Asp Ile Ser Asn Tyr
1               5
```

<210> SEQ ID NO 189
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189

<210> SEQ ID NO 190
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 190

Asp Ala Ser
1

<210> SEQ ID NO 191
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 191
cagcagtatg atcatctccc gatcacc                                          27

<210> SEQ ID NO 192
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 192

Gln Gln Tyr Asp His Leu Pro Ile Thr
1               5

<210> SEQ ID NO 193
<211> LENGTH: 345
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 193
gaggtgcagc tggtggagtc tggggggaggc ttggttcagc ctggggggtc cctgagactc      60
tcctgtgcag cctctggatt cacctttagc acctatgcca tgagctgggt ccgccaggct     120
ccagggaagg ggctggagtg ggtctcagtt attagtggta gttttattag cacatactac     180
gcagactccg tgaagggccg gttcaccatc tccagagaca attccaagaa cacgctgtat     240
ctgcaaatga ccagcctgag agccgaggac acggccgtat attactgtgc gaaaaactcc     300
cccttTgact actggggcca gggaaccctg gtcaccgtct cctca                     345

<210> SEQ ID NO 194
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 194

Glu Val Gln Leu Val Glu Ser Gly Gly Gly Leu Val Gln Pro Gly Gly

```
                1               5                  10                  15
Ser Leu Arg Leu Ser Cys Ala Ala Ser Gly Phe Thr Phe Ser Thr Tyr
                20                  25                  30

Ala Met Ser Trp Val Arg Gln Ala Pro Gly Lys Gly Leu Glu Trp Val
                35                  40                  45

Ser Val Ile Ser Gly Ser Phe Ile Ser Thr Tyr Tyr Ala Asp Ser Val
                50                  55                  60

Lys Gly Arg Phe Thr Ile Ser Arg Asp Asn Ser Lys Asn Thr Leu Tyr
 65                  70                  75                  80

Leu Gln Met Thr Ser Leu Arg Ala Glu Asp Thr Ala Val Tyr Tyr Cys
                85                  90                  95

Ala Lys Asn Ser Pro Phe Asp Tyr Trp Gly Gln Gly Thr Leu Val Thr
                100                 105                 110

Val Ser Ser
        115

<210> SEQ ID NO 195
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
ggattcacct ttagcaccta tgcc                                              24

<210> SEQ ID NO 196
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Gly Phe Thr Phe Ser Thr Tyr Ala
1               5

<210> SEQ ID NO 197
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
attagtggta gttttattag caca                                              24

<210> SEQ ID NO 198
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Ile Ser Gly Ser Phe Ile Ser Thr
1               5

<210> SEQ ID NO 199
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
gcgaaaaact cccctttga ctac                                            24

<210> SEQ ID NO 200
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Ala Lys Asn Ser Pro Phe Asp Tyr
1               5

<210> SEQ ID NO 201
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 201
gacatcgtga tgacccagtc tccagactcc ctgactgtat ctctgggcga gagggccacc    60
atcaactgca gtccagcca gagtgtttta tacagctcca acaataagaa ctacttagct   120
tggtaccagc agaaaccagg acagcctcct aacctgctca tttactgggc atctacccgg   180
gaatccgggg tccctgaccg attcagtggc agcgggtctg ggacagattt cactctcacc   240
atcagcagcc tgcaggctga agatgtggca gtttattact gtcagcaata ttatactact   300
ccgtggacgt tcggccgagg gaccaaggtg gagatcaaa                          339

<210> SEQ ID NO 202
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Asp Ile Val Met Thr Gln Ser Pro Asp Ser Leu Thr Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Asn Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Thr Pro Trp Thr Phe Gly Arg Gly Thr Lys Val Glu Ile
            100                 105                 110
```

Lys

<210> SEQ ID NO 203
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
cagagtgttt tatacagctc caacaataag aactac                                 36

<210> SEQ ID NO 204
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Gln Ser Val Leu Tyr Ser Ser Asn Asn Lys Asn Tyr
1               5                   10

<210> SEQ ID NO 205
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205 tgggcatct                                                                9

<210> SEQ ID NO 206
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Trp Ala Ser
1

<210> SEQ ID NO 207
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
cagcaatatt atactactcc gtggacg                                           27

<210> SEQ ID NO 208
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Gln Gln Tyr Tyr Thr Thr Pro Trp Thr
1               5

<210> SEQ ID NO 209
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 209

```
gaggtgcagc tggtggagtc tgggggaggc ttggtacagc cggggggtc cctgagactc      60 tcctgtgcag cctctggatt cacctttagc aactatgcca tgagctgggt ccgccaggct    120
ccagggaagg gactggagtg ggtctcaact attagtgata ctggtggtag cacatactac    180
gcagactccg tgaagggccg gttcgccctc tccagagaca attccaggaa cacgctgtat    240
ctacaaatga acagcctgag agccgaggac acggccgtat attactgtgc gaaagagggg    300
cccccggact actggggaca gggcaccctg gtcaccgtct cctca                    345
```

<210> SEQ ID NO 210
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Thr Ile Ser Asp Thr Gly Gly Ser Thr Tyr Tyr Ala Asp Ser Val
    50                  55                  60

Lys Gly Arg Phe Ala Leu Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Gly Pro Pro Asp Tyr Trp Gly Gln Gly Thr Leu Val Thr
            100                 105                 110

Val Ser Ser
        115

<210> SEQ ID NO 211
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
ggattcacct ttagcaacta tgcc                                            24

<210> SEQ ID NO 212
<211> LENGTH: 8

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Gly Phe Thr Phe Ser Asn Tyr Ala
1               5

<210> SEQ ID NO 213
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
attagtgata ctggtggtag caca                                            24

<210> SEQ ID NO 214
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Ile Ser Asp Thr Gly Gly Ser Thr
1               5

<210> SEQ ID NO 215
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
gcgaaagagg ggcccccgga ctac                                            24

<210> SEQ ID NO 216
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Ala Lys Glu Gly Pro Pro Asp Tyr
1               5

<210> SEQ ID NO 217
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 217
gaaattgtgt tgacacagtc tccagccacc ctgtctttgt ctccagggga aagagccacc    60
ctctcctgca ggaccagtca gagtgtcagc atctacttag cctggtacca acagaaacct   120
```

```
ggccaggctc ccaggctcct catctatgat gcatccaaga gggccactgg catcccagcc    180
aggttcagtg gcagagggtc tgggacagac ttcactctca ccatcagcag cctagagcct    240
gaagattttg cagtttatta ctgtcagcag cgtagcaact ggcctctcac cttcggccaa    300
gggacacgac tggagattaa a                                              321
```

<210> SEQ ID NO 218
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

```
Glu Ile Val Leu Thr Gln Ser Pro Ala Thr Leu Ser Leu Ser Pro Gly
1               5                   10                  15

Glu Arg Ala Thr Leu Ser Cys Arg Thr Ser Gln Ser Val Ser Ile Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Arg Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Arg Leu Glu Ile Lys
            100                 105
```

<210> SEQ ID NO 219
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219

```
cagagtgtca gcatctac                                                   18
```

<210> SEQ ID NO 220
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

```
Gln Ser Val Ser Ile Tyr
1               5
```

<210> SEQ ID NO 221
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221

```
<210> SEQ ID NO 222
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Asp Ala Ser
1

<210> SEQ ID NO 223
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
cagcagcgta gcaactggcc tctcacc                                           27

<210> SEQ ID NO 224
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Gln Gln Arg Ser Asn Trp Pro Leu Thr
1               5

<210> SEQ ID NO 225
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 225
gaggtgcagc tggtggagtc tgggggaggc ttggtgcagc cggggggtc  cctgagactc        60 tcctgtgcag cctctggatt caccttcaga aactatgcca tgaactgggc cgccaggct        120 ccagggaagg gactggagtg ggtctcaggt attactggta gtggtggtgc cacatactac       180
gcagactccg tgaagggccg gttcaccatc tccagagaaa attccaagaa cacgctgttt       240
ctgcaaatgg acaccctgag agccgaggac acggccgttt attattgtgc gaaagatcgg       300
aggtatttcc ctacttcggg gggtcctcag tggggccagg gaaccctggt caccgtctcc       360
tca                                                                    363

<210> SEQ ID NO 226
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226
```

(gatgcatcc    9 — continued from previous page)

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asn Tyr
            20                  25                  30

Ala Met Asn Trp Ala Arg Gln Ala Pro Gly Lys Gly Leu Glu Trp Val
        35                  40                  45

Ser Gly Ile Thr Gly Ser Gly Gly Ala Thr Tyr Tyr Ala Asp Ser Val
    50                  55                  60

Lys Gly Arg Phe Thr Ile Ser Arg Glu Asn Ser Lys Asn Thr Leu Phe
65                  70                  75                  80

Leu Gln Met Asp Thr Leu Arg Ala Glu Asp Thr Ala Val Tyr Tyr Cys
                85                  90                  95

Ala Lys Asp Arg Arg Tyr Phe Pro Thr Ser Gly Gly Pro Gln Trp Gly
            100                 105                 110

Gln Gly Thr Leu Val Thr Val Ser Ser
        115                 120

<210> SEQ ID NO 227
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
ggattcacct tcagaaacta tgcc                                          24

<210> SEQ ID NO 228
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Gly Phe Thr Phe Arg Asn Tyr Ala
1               5

<210> SEQ ID NO 229
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
attactggta gtggtggtgc caca                                          24

<210> SEQ ID NO 230
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Ile Thr Gly Ser Gly Gly Ala Thr
1               5

-continued

<210> SEQ ID NO 231
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
gcgaaagatc ggaggtattt ccctacttcg gggggtcctc ag                        42

<210> SEQ ID NO 232
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Ala Lys Asp Arg Arg Tyr Phe Pro Thr Ser Gly Gly Pro Gln
1               5                   10

<210> SEQ ID NO 233
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 233
gatattgtga tgactcagtc tccactctcc ctgcccgtca cccctggaga gccggcctcc     60
atctcctgca ggtcttctcg gagcctcctg catagttctg gatacaacta tttggattgg    120
tacctgcaga agccagggca gtctccacag ctcctgctct atttgggttc aatcgggcc     180 tccggggtcc ctgacaggtt cagtggcagt ggatcaggca catattttac actgaaaatc    240
agcagagtgg acgctgaaga tgttggggtt tattactgca tgcaagctct acaaactccg    300
tggacgttcg gccaagggac caaggtggaa atcaaa                              336

<210> SEQ ID NO 234
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Asp Ile Val Met Thr Gln Ser Pro Leu Ser Leu Pro Val Thr Pro Gly
1               5                   10                  15

Glu Pro Ala Ser Ile Ser Cys Arg Ser Ser Arg Ser Leu Leu His Ser
            20                  25                  30

Ser Gly Tyr Asn Tyr Leu Asp Trp Tyr Leu Gln Lys Pro Gly Gln Ser
        35                  40                  45

Pro Gln Leu Leu Leu Tyr Leu Gly Ser Asn Arg Ala Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Asp Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys

<210> SEQ ID NO 235
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
cggagcctcc tgcatagttc tggatacaac tat                                33

<210> SEQ ID NO 236
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Arg Ser Leu Leu His Ser Ser Gly Tyr Asn Tyr
1               5                   10

<210> SEQ ID NO 237
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237 ttgggttct                                                            9

<210> SEQ ID NO 238
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Leu Gly Ser
1

<210> SEQ ID NO 239
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
atgcaagctc tacaaactcc gtggacg                                       27

<210> SEQ ID NO 240
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Met Gln Ala Leu Gln Thr Pro Trp Thr
1               5

<210> SEQ ID NO 241
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 241
gaggtgcagc tggtggagtc tgggggaggc ttggtccagc cggggggtc cctgagactc     60 tcctgtgcag cctctggatt cacctttagt agctttagga tgacctgggt ccgccaggct   120
ccagggaagg gctggagtg gtggccaac ataaagcaag atggaagtga aaatactat      180 gtggactctg tgaagggccg attcaccatc tccagagaca acgccaagaa ctcactgtat   240
ctgcaaatga acagcctgag agccgaggac acggctgtgt attactgtgc gagaggggg   300 ggtatagcag cttactgggg ccagggaacc ctggtcaccg tctcctca               348

<210> SEQ ID NO 242
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Arg Met Thr Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gly Ile Ala Ala Tyr Trp Gly Gln Gly Thr Leu Val
            100                 105                 110

Thr Val Ser Ser
        115

<210> SEQ ID NO 243
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
ggattcacct ttagtagctt tagg                                            24

<210> SEQ ID NO 244
<211> LENGTH: 8
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 244

Gly Phe Thr Phe Ser Ser Phe Arg
1               5

<210> SEQ ID NO 245
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
ataaagcaag atggaagtga gaaa                                          24

<210> SEQ ID NO 246
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Ile Lys Gln Asp Gly Ser Glu Lys
1               5

<210> SEQ ID NO 247
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
gcgagagggg ggggtatagc agcttac                                       27

<210> SEQ ID NO 248
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Ala Arg Gly Gly Gly Ile Ala Ala Tyr
1               5

<210> SEQ ID NO 249
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 249
gacatccaga tgacccagtc tccatcctcc ctgtctgcat ctgtaggaga cagagtcacc    60
atcacttgcc gggcaagtca gagcattagc agctatttaa attggtatca gcagaaacca   120
```

```
gggaaagccc ctaagctcct gatctatgct gcatccagtt tgcaaagtgg ggtcccgtca    180
aggttcagtg gcagtggatc tgggacagat ttcactctca ccatcagcag tctgcaacct    240
gaagattttg caacttacta ctgtcaacag agttacagta ccccctccgat caccttcggc   300 caagggacac gactggagat taaa                                           324
```

<210> SEQ ID NO 250
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105
```

<210> SEQ ID NO 251
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251

```
cagagcatta gcagctat                                                  18
```

<210> SEQ ID NO 252
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

```
Gln Ser Ile Ser Ser Tyr
1               5
```

<210> SEQ ID NO 253
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253

```
gctgcatcc                                                            9
```

<210> SEQ ID NO 254
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Ala Ala Ser
1

<210> SEQ ID NO 255
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
caacagagtt acagtacccc tccgatcacc                                         30

<210> SEQ ID NO 256
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Gln Gln Ser Tyr Ser Thr Pro Pro Ile Thr
1               5                   10

<210> SEQ ID NO 257
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 257
gaggtgcagc tggtggagtc tgggggaggc ttggtacagc ctggggggtc cctgagactc         60
tcctgtgcag cctctggatt cacctttagc agctatgcca tgagctgggt ccgccaggct        120
ccagggaagg ggctggagtg ggtctcagct attagtggta gtggtggtag cacatactac        180
gcagactccg tgaagggccg gttcaccatc tccagagaca attccaagaa cacgctgtat        240
ctgcaaatga acagcctgag agccgaggac acggccgtat attactgtgc gaaagatcgg        300
ggggaaaacc ggtattacta ctactactac ggtatggacg tctggggcca agggaccacg        360
gtcaccgtct cctca                                                        375

<210> SEQ ID NO 258
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

Glu Val Gln Leu Val Glu Ser Gly Gly Gly Leu Val Gln Pro Gly Gly

```
 1               5                   10                  15
Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Gly Glu Asn Arg Tyr Tyr Tyr Tyr Tyr Tyr Gly Met
                100                 105                 110

Asp Val Trp Gly Gln Gly Thr Thr Val Thr Val Ser Ser
            115                 120                 125

<210> SEQ ID NO 259
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
ggattcacct ttagcagcta tgcc                                          24

<210> SEQ ID NO 260
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Gly Phe Thr Phe Ser Ser Tyr Ala
1               5

<210> SEQ ID NO 261
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
attagtggta gtggtggtag caca                                          24

<210> SEQ ID NO 262
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Ile Ser Gly Ser Gly Gly Ser Thr
1               5

<210> SEQ ID NO 263
```

<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 263
gcgaaagatc gggggaaaa ccggtattac tactactact acggtatgga cgtc    54

<210> SEQ ID NO 264
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 264

Ala Lys Asp Arg Gly Glu Asn Arg Tyr Tyr Tyr Tyr Tyr Gly Met
1               5                   10                  15

Asp Val

<210> SEQ ID NO 265
<211> LENGTH: 396
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 265
caggtgcagc tggtggagtc tgggggaggc gtggtccagc ctggggaggtc cctgagactc    60 tcctgtacag cctctggatt caccttcaat aactatggca tccactgggt ccgccaggct   120
ccaggcaagg ggctggaatg ggtggcagtt atatcatatg atggaagtaa taaattctat   180
gcagagtccg tgaggggccg attcaccatc tccagagaca attccaggaa cacactgttt   240
ctgcagatga tcagcctgcg aggtgaggac tcggctgttt attactgtgc gaaagatcga   300
ccctattacg atattttgac tgctcattat ccctctgact actacttcta cgctatggac   360
gtctggggcc atgggaccac ggtcaccgtc tcctca                              396

<210> SEQ ID NO 266
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 266

Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Asn Asn Tyr
            20                  25                  30

Gly Ile His Trp Val Arg Gln Ala Pro Gly Lys Gly Leu Glu Trp Val
        35                  40                  45

Ala Val Ile Ser Tyr Asp Gly Ser Asn Lys Phe Tyr Ala Glu Ser Val
    50                  55                  60

Arg Gly Arg Phe Thr Ile Ser Arg Asp Asn Ser Arg Asn Thr Leu Phe
65                  70                  75                  80

Leu Gln Met Ile Ser Leu Arg Gly Glu Asp Ser Ala Val Tyr Tyr Cys

```
                     85                  90                  95

Ala Lys Asp Arg Pro Tyr Tyr Asp Ile Leu Thr Ala His Tyr Pro Ser
            100                 105                 110

Asp Tyr Tyr Phe Tyr Ala Met Asp Val Trp Gly His Gly Thr Thr Val
        115                 120                 125

Thr Val Ser Ser
    130

<210> SEQ ID NO 267
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
ggattcacct tcaataacta tggc                                              24

<210> SEQ ID NO 268
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Gly Phe Thr Phe Asn Asn Tyr Gly
1               5

<210> SEQ ID NO 269
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
atatcatatg atggaagtaa taaa                                              24

<210> SEQ ID NO 270
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Ile Ser Tyr Asp Gly Ser Asn Lys
1               5

<210> SEQ ID NO 271
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
gcgaaagatc gaccctatta cgatattttg actgctcatt atccctctga ctactacttc      60
tacgctatgg acgtc                                                        75
```

<210> SEQ ID NO 272
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Ala Lys Asp Arg Pro Tyr Tyr Asp Ile Leu Thr Ala His Tyr Pro Ser
1               5                   10                  15

Asp Tyr Tyr Phe Tyr Ala Met Asp Val
            20                  25

<210> SEQ ID NO 273
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 273
caggtgcagc tggtggagtc tgggggaggc gtggtccagc ctggggaggtc cctgagactc     60 tcctgtgcag cctctggctt caccttcact aactatgcca tgcactgggt ccgccaggct    120
ccaggcaagg gactggagtg ggtggcagtt atatcatatg atggaagtca cacatacttt    180
gcagactccg tgaagggccg attcaccatg tccagagaca attccaagaa cacgatatct    240
ctacaaatga acagtctgag acctgaggac acggctgttt atttttgtgc gggaggagga    300
gctactacgt ggttctactt ttacggtttg gacgtctggg gccaagggac cacggtcacc    360
gtctcctca                                                            369

<210> SEQ ID NO 274
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 274

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Thr Asn Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser His Thr Tyr Phe Ala Asp Ser Val
    50                  55                  60

Lys Gly Arg Phe Thr Met Ser Arg Asp Asn Ser Lys Asn Thr Ile Ser
65                  70                  75                  80

Leu Gln Met Asn Ser Leu Arg Pro Glu Asp Thr Ala Val Tyr Phe Cys
                85                  90                  95

Ala Gly Gly Gly Ala Thr Thr Trp Phe Tyr Phe Tyr Gly Leu Asp Val
            100                 105                 110

Trp Gly Gln Gly Thr Thr Val Thr Val Ser Ser
        115                 120

```
<210> SEQ ID NO 275
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
ggcttcacct tcactaacta tgcc                                              24

<210> SEQ ID NO 276
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Gly Phe Thr Phe Thr Asn Tyr Ala
1               5

<210> SEQ ID NO 277
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
atatcatatg atggaagtca caca                                              24

<210> SEQ ID NO 278
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Ile Ser Tyr Asp Gly Ser His Thr
1               5

<210> SEQ ID NO 279
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
gcgggaggag gagctactac gtggttctac ttttacggtt tggacgtc                    48

<210> SEQ ID NO 280
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Ala Gly Gly Gly Ala Thr Thr Trp Phe Tyr Phe Tyr Gly Leu Asp Val
1               5                   10                  15
```

<210> SEQ ID NO 281
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 281
gaggtgcagc tggtggagtc tgggggaggc ttggtaaaac cggggggtc ccttagactc      60 tcctgtacag cctctggatt cactttcggt aatgcctgga tgagctgggt ccggcaggct     120
ccagggaagg gcctggagtg ggttggcctt attaaaggta aaactgatgg tgggacaaca     180
aactacgctg cacccgtgaa aggcagattc accatctcaa gagatgattc aaaaaacacg     240
ctgtatctgc atttgaacag cctgagaacc gaggacacag ccttgtatta ctgtaccaca     300
gatcaggtgg aactacgaca atactactac tacggtttgg acgtctgggg ccaggggacc     360
acggtcaccg tctcctca                                                   378

<210> SEQ ID NO 282
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 282

Glu Val Gln Leu Val Glu Ser Gly Gly Gly Leu Val Lys Pro Gly Gly
1               5                   10                  15

Ser Leu Arg Leu Ser Cys Thr Ala Ser Gly Phe Thr Phe Gly Asn Ala
            20                  25                  30

Trp Met Ser Trp Val Arg Gln Ala Pro Gly Lys Gly Leu Glu Trp Val
        35                  40                  45

Gly Leu Ile Lys Gly Lys Thr Asp Gly Gly Thr Thr Asn Tyr Ala Ala
    50                  55                  60

Pro Val Lys Gly Arg Phe Thr Ile Ser Arg Asp Asp Ser Lys Asn Thr
65                  70                  75                  80

Leu Tyr Leu His Leu Asn Ser Leu Arg Thr Glu Asp Thr Ala Leu Tyr
                85                  90                  95

Tyr Cys Thr Thr Asp Gln Val Glu Leu Arg Gln Tyr Tyr Tyr Tyr Gly
            100                 105                 110

Leu Asp Val Trp Gly Gln Gly Thr Thr Val Thr Val Ser Ser
        115                 120                 125

<210> SEQ ID NO 283
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
ggattcactt tcggtaatgc ctgg                                             24

<210> SEQ ID NO 284
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Gly Phe Thr Phe Gly Asn Ala Trp
1               5

<210> SEQ ID NO 285
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
attaaaggta aaactgatgg tgggacaaca                                      30

<210> SEQ ID NO 286
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Ile Lys Gly Lys Thr Asp Gly Gly Thr Thr
1               5                   10

<210> SEQ ID NO 287
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
accacagatc aggtggaact acgacaatac tactactacg gtttggacgt c              51

<210> SEQ ID NO 288
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Thr Thr Asp Gln Val Glu Leu Arg Gln Tyr Tyr Tyr Tyr Gly Leu Asp
1               5                   10                  15

Val

<210> SEQ ID NO 289
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 289
gaggtgcagc tggtggagtc tgggggaggc ttggtacagc cagggcggtc cctgagactc     60
tcctgtacag cttctggatt cagctttggt gataatgcta tgggctgggt ccgccaggct    120

```
ccagggaagg ggctggagtg ggtaagtttc attagaagga aagcttctgg tgggacaaca    180
gaatacgccg cgtctgtgaa aggcagattc accatctcaa gagatgattc caaaagcatc    240
gcctatctgc aaatgaacag tctgaaaacc gaggacacag gcgtttatta ttgtactaga    300
ggaggagcag tgtacggcta ctggggccag ggaaccctgg tcaccgtctc ctca          354
```

<210> SEQ ID NO 290
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide <400> SEQUENCE: 290

```
Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Ser Phe Gly Asp Asn
            20                  25                  30

Ala Met Gly Trp Val Arg Gln Ala Pro Gly Lys Gly Leu Glu Trp Val
        35                  40                  45

Ser Phe Ile Arg Arg Lys Ala Ser Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Gly Val Tyr
                85                  90                  95

Tyr Cys Thr Arg Gly Gly Ala Val Tyr Gly Tyr Trp Gly Gln Gly Thr
            100                 105                 110

Leu Val Thr Val Ser Ser
        115
```

<210> SEQ ID NO 291
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide <400> SEQUENCE: 291

```
ggattcagct ttggtgataa tgct                                            24
```

<210> SEQ ID NO 292
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide <400> SEQUENCE: 292

```
Gly Phe Ser Phe Gly Asp Asn Ala
1               5
```

<210> SEQ ID NO 293
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 293
attagaagga aagcttctgg tgggacaaca                                          30

<210> SEQ ID NO 294
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Ile Arg Arg Lys Ala Ser Gly Gly Thr Thr
1               5                   10

<210> SEQ ID NO 295
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
actagaggag gagcagtgta cggctac                                             27

<210> SEQ ID NO 296
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Thr Arg Gly Gly Ala Val Tyr Gly Tyr
1               5

<210> SEQ ID NO 297
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 297
caggtgcagc tggtggagtc tgggggaggc gtggtccagc ctggggaggtc cctgagactc        60 tcctgtgcag cgtctggatt caccttcagt agctatggca tgcactgggt ccgccaggct       120
ccaggcaagg ggctggagtg ggtggcagtt atatggtatg atggaagtaa taaatactat       180
gcagactccg tgaagggccg attcaccatc tccagagaca attccaagaa cacgctgtat       240
ctgcaaatga acagcctgag agccgaggac acggctgttt attactgtgc gagagattgg       300
gtacgatttt tggagtggtt tccccacttt gactactggg gccagggaac cctggtcacc       360
gtctcctca                                                              369

<210> SEQ ID NO 298
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 298

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Trp Val Arg Phe Leu Glu Trp Phe Pro His Phe Asp Tyr
            100                 105                 110

Trp Gly Gln Gly Thr Leu Val Thr Val Ser Ser
        115                 120

<210> SEQ ID NO 299
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
ggattcacct tcagtagcta tggc                                              24

<210> SEQ ID NO 300
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Gly Phe Thr Phe Ser Ser Tyr Gly
1               5

<210> SEQ ID NO 301
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
atatggtatg atggaagtaa taaa                                              24

<210> SEQ ID NO 302
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Ile Trp Tyr Asp Gly Ser Asn Lys

<210> SEQ ID NO 303
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 303
gcgagagatt gggtacgatt tttggagtgg tttccccact ttgactac        48

<210> SEQ ID NO 304
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 304

Ala Arg Asp Trp Val Arg Phe Leu Glu Trp Phe Pro His Phe Asp Tyr
1               5                   10                  15

<210> SEQ ID NO 305
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 305
gaggtgcagc tggtggagtc tgggggaggc ttggtacagc ctggggggtc cctgagactc        60
tcctgtgcag cctctggatt caccttttagc aactatgcca tgagctgggt ccgccaggtt       120
ccagggaagg gctggagtg gtctcaact attagtggta gtggtggtag cacatactac         180
gcagactccg tgaagggccg gttcaccatc tccagagaca attccaagaa ctcgctgtat       240
ctgcaaatga acagcctgag agccgaggac acggccgtat attattgtgc gaaattggtt       300
cggggagtta ttggctggtt cgaccccctgg ggccagggaa ccctggtcac cgtctcctca      360

<210> SEQ ID NO 306
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 306

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
                20                  25                  30

Ala Met Ser Trp Val Arg Gln Val Pro Gly Lys Gly Leu Glu Trp Val
            35                  40                  45

Ser Thr Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys

```
                85                  90                  95
Ala Lys Leu Val Arg Gly Val Ile Gly Trp Phe Asp Pro Trp Gly Gln
            100                 105                 110

Gly Thr Leu Val Thr Val Ser Ser
        115                 120

<210> SEQ ID NO 307
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
ggattcacct ttagcaacta tgcc                                             24

<210> SEQ ID NO 308
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Gly Phe Thr Phe Ser Asn Tyr Ala
1               5

<210> SEQ ID NO 309
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
attagtggta gtggtggtag caca                                             24

<210> SEQ ID NO 310
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Ile Ser Gly Ser Gly Gly Ser Thr
1               5

<210> SEQ ID NO 311
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
gcgaaattgg ttcggggagt tattggctgg ttcgacccc                             39

<210> SEQ ID NO 312
<211> LENGTH: 13
<212> TYPE: PRT
```

<213> ORGANISM: Artificial Sequence
<220> FEATURE:
<223> OTHER INFORMATION: Description of Artificial Sequence: Synthetic peptide

<400> SEQUENCE: 312

Ala Lys Leu Val Arg Gly Val Ile Gly Trp Phe Asp Pro
1               5                   10

<210> SEQ ID NO 313
<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 313
caggtgcagc tggtggagtc tgggggaggc gtggtccagc ctggagggtc cgtgagactc      60
tcctgtggag cgtctggatt cactttcaaa tactatggca tgcactgggt ccgccaggct     120
ccaggcaagg ggctggaatg ggtggcagtc atttggtatg atggaagaaa taaattttat     180
gcagactctg tgaagggccg cttcactatc tccagagaca attccaagaa cacggtgaat     240
ctggaaatga acaacctgag agccgaggac acggctatat attactgtgc gagagatgga     300
ggaacagcgg atggcgacta ttttgactac tggggccagg gaaccctggt caccgtctcc     360
tca                                                                   363

<210> SEQ ID NO 314
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 314

Gln Val Gln Leu Val Glu Ser Gly Gly Gly Val Val Gln Pro Gly Arg
1               5                   10                  15

Ser Val Arg Leu Ser Cys Gly Ala Ser Gly Phe Thr Phe Lys Tyr Tyr
                20                  25                  30

Gly Met His Trp Val Arg Gln Ala Pro Gly Lys Gly Leu Glu Trp Val
            35                  40                  45

Ala Val Ile Trp Tyr Asp Gly Arg Asn Lys Phe Tyr Ala Asp Ser Val
        50                  55                  60

Lys Gly Arg Phe Thr Ile Ser Arg Asp Asn Ser Lys Asn Thr Val Asn
65                  70                  75                  80

Leu Glu Met Asn Asn Leu Arg Ala Glu Asp Thr Ala Ile Tyr Tyr Cys
                85                  90                  95

Ala Arg Asp Gly Gly Thr Ala Asp Gly Asp Tyr Phe Asp Tyr Trp Gly
            100                 105                 110

Gln Gly Thr Leu Val Thr Val Ser Ser
        115                 120

<210> SEQ ID NO 315
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

```
<400> SEQUENCE: 315
ggattcactt tcaaatacta tggc                                          24

<210> SEQ ID NO 316
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Gly Phe Thr Phe Lys Tyr Tyr Gly
1               5

<210> SEQ ID NO 317
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
atttggtatg atggaagaaa taaa                                          24

<210> SEQ ID NO 318
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Ile Trp Tyr Asp Gly Arg Asn Lys
1               5

<210> SEQ ID NO 319
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
gcgagagatg gaggaacagc ggatggcgac tattttgact ac                      42

<210> SEQ ID NO 320
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Ala Arg Asp Gly Gly Thr Ala Asp Gly Asp Tyr Phe Asp Tyr
1               5                   10

<210> SEQ ID NO 321
<211> LENGTH: 324
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 321

```
gaaatagttt tgacacagag tcccggcaca ctgtcactct ctcccgggga aagagccacc      60
ttgtcatgta gagcaagtca gtcagtctct agctcttatc tcgcctggta ccagcagaaa     120
ccgggacagg cccctagact gctgatctac ggggcaagtt ccagggccac cggaatcccc     180
gaccggttca gtggaagcgg aagcggaacc gatttacttt tgacgatttc tagactggag     240
ccagaggatt tcgccgttta ctattgtcaa cagtacggaa gcagcccgtg gacgtttggc     300
cagggcacga aggtagaaat caag                                            324
```

<210> SEQ ID NO 322
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 322

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 323
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323

```
agagcaagtc agtcagtctc tagctcttat ctcgcc                               36
```

<210> SEQ ID NO 324
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Arg Ala Ser Gln Ser Val Ser Ser Ser Tyr Leu Ala
1               5                   10

<210> SEQ ID NO 325
<211> LENGTH: 21
<212> TYPE: DNA

<213> ORGANISM: Artificial Sequence
<220> FEATURE:
<223> OTHER INFORMATION: Description of Artificial Sequence: Synthetic
    oligonucleotide

<400> SEQUENCE: 325
ggggcaagtt ccagggccac c    21

<210> SEQ ID NO 326
<211> LENGTH: 7
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 326

Gly Ala Ser Ser Arg Ala Thr
1               5

<210> SEQ ID NO 327
<211> LENGTH: 27
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 327
caacagtacg gaagcagccc gtggacg    27

<210> SEQ ID NO 328
<211> LENGTH: 9
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 328

Gln Gln Tyr Gly Ser Ser Pro Trp Thr
1               5

<210> SEQ ID NO 329
<211> LENGTH: 366
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 329
gaggtgcagc tggtggagtc tgggggaggt tggtacagc ctgggggtc cctgagactc    60 tcctgtgtag gcactggatt caccttagc aactatgcca tgagctgggt ccgccaggct    120
ccagggaagg ggctggagtg gtctcaggt attagtggta gaagtagtgg cacattctac    180
gcagactccg tgaagggccg gttcaccatc tccagagaca attcccagaa tacgctgtat    240
ctgcaaatga acagcctggg agccgaggac acggccgtat attactgtgc gaaagtttcc    300
cgttataact gggactacgt cccctttgac ttctggggcc agggaaccct ggtcaccgtc    360
tcctca    366

<210> SEQ ID NO 330
<211> LENGTH: 122
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 330

```
Glu Val Gln Leu Val Glu Ser Gly Gly Gly Leu Val Gln Pro Gly Gly
1               5                   10                  15
Ser Leu Arg Leu Ser Cys Val Gly Thr Gly Phe Thr Phe Ser Asn Tyr
            20                  25                  30
Ala Met Ser Trp Val Arg Gln Ala Pro Gly Lys Gly Leu Glu Trp Val
        35                  40                  45
Ser Gly Ile Ser Gly Arg Ser Ser Gly Thr Phe Tyr Ala Asp Ser Val
    50                  55                  60
Lys Gly Arg Phe Thr Ile Ser Arg Asp Asn Ser Gln Asn Thr Leu Tyr
65                  70                  75                  80
Leu Gln Met Asn Ser Leu Gly Ala Glu Asp Thr Ala Val Tyr Tyr Cys
                85                  90                  95
Ala Lys Val Ser Arg Tyr Asn Trp Asp Tyr Val Pro Phe Asp Phe Trp
            100                 105                 110
Gly Gln Gly Thr Leu Val Thr Val Ser Ser
        115                 120
```

<210> SEQ ID NO 331
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 331
ggattcacct ttagcaacta tgcc                                    24

<210> SEQ ID NO 332
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 332

```
Gly Phe Thr Phe Ser Asn Tyr Ala
1               5
```

<210> SEQ ID NO 333
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 333
attagtggta gaagtagtgg caca                                    24

<210> SEQ ID NO 334
<211> LENGTH: 8
<212> TYPE: PRT
<213> ORGANISM: Artificial Sequence
<220> FEATURE:
<223> OTHER INFORMATION: Description of Artificial Sequence: Synthetic peptide

```
<400> SEQUENCE: 334

Ile Ser Gly Arg Ser Ser Gly Thr
1               5

<210> SEQ ID NO 335
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 335
gcgaaagttt cccgttataa ctgggactac gtcccctttg acttc                45

<210> SEQ ID NO 336
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Ala Lys Val Ser Arg Tyr Asn Trp Asp Tyr Val Pro Phe Asp Phe
1               5                   10                  15

<210> SEQ ID NO 337
<211> LENGTH: 39
<212> TYPE: PRT
<213> ORGANISM: Homo sapiens
<220> FEATURE:
<223> OTHER INFORMATION: Human AngPTL8 Naked Peptide: amino acids 22-60
<300> PUBLICATION INFORMATION:
<308> DATABASE ACCESSION NUMBER: GenBank Database: NP_061157.3

<400> SEQUENCE: 337

Ala Pro Met Gly Gly Pro Glu Leu Ala Gln His Glu Glu Leu Thr Leu
1               5                   10                  15

Leu Phe His Gly Thr Leu Gln Leu Gly Gln Ala Leu Asn Gly Val Tyr
            20                  25                  30

Arg Thr Thr Glu Gly Arg Leu
        35

<210> SEQ ID NO 338
<211> LENGTH: 26
<212> TYPE: PRT
<213> ORGANISM: Homo sapiens
<220> FEATURE:
<223> OTHER INFORMATION: Human ANGPTL3 Shift Naked Peptide: amino acids
      32-57
<300> PUBLICATION INFORMATION:
<308> DATABASE ACCESSION NUMBER: GenBank Database: NP_055310.1

<400> SEQUENCE: 338

Glu Pro Lys Ser Arg Phe Ala Met Leu Asp Asp Val Lys Ile Leu Ala
1               5                   10                  15

Asn Gly Leu Leu Gln Leu Gly His Gly Leu
            20                  25

<210> SEQ ID NO 339
<211> LENGTH: 34
<212> TYPE: PRT
<213> ORGANISM: Homo sapiens
<220> FEATURE:
```

<223> OTHER INFORMATION: Human ANGPTL4 Naked Peptide: amino acids 34-67
<300> PUBLICATION INFORMATION:
<308> DATABASE ACCESSION NUMBER: GenBank Database: NP_001034756.1

<400> SEQUENCE: 339

```
Arg Phe Ala Ser Trp Asp Glu Met Asn Val Leu Ala His Gly Leu Leu
1               5                   10                  15
Gln Leu Gly Gln Gly Leu Arg Glu His Ala Glu Arg Thr Arg Ser Gln
            20                  25                  30
Leu Cys
```

<210> SEQ ID NO 340
<211> LENGTH: 413
<212> TYPE: PRT
<213> ORGANISM: Artificial Sequence
<220> FEATURE:
<223> OTHER INFORMATION: Description of Artificial Sequence: Synthetic
      hANGPTL8-mFc aa 1-177: amino acids 22-198 of NP_061157.3 aa 178-
      413: GPG linker and mouse IgG2a Fc tag polypeptide
<300> PUBLICATION INFORMATION:
<308> DATABASE ACCESSION NUMBER: GenBank Database: NP_061157.3 (part of
      full length sequence)

<400> SEQUENCE: 340

```
Ala Pro Met Gly Gly Pro Glu Leu Ala Gln His Glu Glu Leu Thr Leu
1               5                   10                  15
Leu Phe His Gly Thr Leu Gln Leu Gly Gln Ala Leu Asn Gly Val Tyr
            20                  25                  30
Arg Thr Thr Glu Gly Arg Leu Thr Lys Ala Arg Asn Ser Leu Gly Leu
        35                  40                  45
Tyr Gly Arg Thr Ile Glu Leu Leu Gly Gln Glu Val Ser Arg Gly Arg
    50                  55                  60
Asp Ala Ala Gln Glu Leu Arg Ala Ser Leu Leu Glu Thr Gln Met Glu
65                  70                  75                  80
Glu Asp Ile Leu Gln Leu Gln Ala Glu Ala Thr Ala Glu Val Leu Gly
                85                  90                  95
Glu Val Ala Gln Ala Gln Lys Val Leu Arg Asp Ser Val Gln Arg Leu
            100                 105                 110
Glu Val Gln Leu Arg Ser Ala Trp Leu Gly Pro Ala Tyr Arg Glu Phe
        115                 120                 125
Glu Val Leu Lys Ala His Ala Asp Lys Gln Ser His Ile Leu Trp Ala
    130                 135                 140
Leu Thr Gly His Val Gln Arg Gln Arg Arg Glu Met Val Ala Gln Gln
145                 150                 155                 160
His Arg Leu Arg Gln Ile Gln Glu Arg Leu His Thr Ala Ala Leu Pro
                165                 170                 175
Ala Gly Pro Gly Glu Pro Arg Gly Pro Thr Ile Lys Pro Cys Pro Pro
            180                 185                 190
Cys Lys Cys Pro Ala Pro Asn Leu Leu Gly Gly Pro Ser Val Phe Ile
        195                 200                 205
Phe Pro Pro Lys Ile Lys Asp Val Leu Met Ile Ser Leu Ser Pro Ile
    210                 215                 220
Val Thr Cys Val Val Val Asp Val Ser Glu Asp Asp Pro Asp Val Gln
225                 230                 235                 240
Ile Ser Trp Phe Val Asn Asn Val Glu Val His Thr Ala Gln Thr Gln
                245                 250                 255
Thr His Arg Glu Asp Tyr Asn Ser Thr Leu Arg Val Val Ser Ala Leu
            260                 265                 270
```

```
Pro Ile Gln His Gln Asp Trp Met Ser Gly Lys Glu Phe Lys Cys Lys
            275                 280                 285

Val Asn Asn Lys Asp Leu Pro Ala Pro Ile Glu Arg Thr Ile Ser Lys
    290                 295                 300

Pro Lys Gly Ser Val Arg Ala Pro Gln Val Tyr Val Leu Pro Pro Pro
305                 310                 315                 320

Glu Glu Glu Met Thr Lys Lys Gln Val Thr Leu Thr Cys Met Val Thr
                325                 330                 335

Asp Phe Met Pro Glu Asp Ile Tyr Val Glu Trp Thr Asn Asn Gly Lys
            340                 345                 350

Thr Glu Leu Asn Tyr Lys Asn Thr Glu Pro Val Leu Asp Ser Asp Gly
        355                 360                 365

Ser Tyr Phe Met Tyr Ser Lys Leu Arg Val Glu Lys Lys Asn Trp Val
370                 375                 380

Glu Arg Asn Ser Tyr Ser Cys Ser Val Val His Glu Gly Leu His Asn
385                 390                 395                 400

His His Thr Thr Lys Ser Phe Ser Arg Thr Pro Gly Lys
                405                 410

<210> SEQ ID NO 341
<211> LENGTH: 410
<212> TYPE: PRT
<213> ORGANISM: Artificial Sequence
<220> FEATURE:
<223> OTHER INFORMATION: Description of Artificial Sequence: Synthetic
      MfAngPTL8-mFc aa 1-177: amino acids 78-254 of XP_005588064.1aa
      178-410: mouse IgG2a Fc tag polypeptide
<300> PUBLICATION INFORMATION:
<308> DATABASE ACCESSION NUMBER: GenBank Database: XP_005588064.1 (part
      of full length sequence)

<400> SEQUENCE: 341

Ala Pro Val Gly Ser Pro Glu Leu Ala Glu His Glu Leu Thr Leu
1               5                   10                  15

Leu Phe His Gly Thr Leu Gln Leu Gly Gln Ala Leu Asn Gly Val Tyr
            20                  25                  30

Lys Thr Thr Glu Gly Arg Leu Thr Lys Ala Arg Asn Ser Leu Gly Leu
        35                  40                  45

Tyr Gly Arg Thr Val Glu Leu Leu Gly Gln Glu Val Ser Arg Gly Arg
50                  55                  60

Asp Ala Ala Gln Glu Leu Arg Ala Ser Leu Leu Glu Thr Gln Met Glu
65                  70                  75                  80

Glu Asp Ile Leu Gln Leu Lys Ala Glu Ala Ile Ala Glu Val Leu Glu
            85                  90                  95

Glu Val Ala Gln Ala Gln Lys Val Leu Gln Asp Ser Val Arg Arg Leu
        100                 105                 110

Glu Val Gln Leu Arg Ser Ala Trp Leu Gly Pro Ala Tyr Gln Glu Phe
    115                 120                 125

Glu Val Leu Lys Ala His Ala Asp Lys Gln Ser His Ile Leu Trp Ala
    130                 135                 140

Leu Thr Gly His Val Gln Arg Gln Arg Glu Met Val Ala Gln Gln
145                 150                 155                 160

His Arg Leu Arg Gln Ile Gln Glu Arg Ile His Lys Ala Ala Leu Pro
                165                 170                 175

Ala Glu Pro Arg Gly Pro Thr Ile Lys Pro Cys Pro Pro Cys Lys Cys
            180                 185                 190
```

```
Pro Ala Pro Asn Leu Leu Gly Gly Pro Ser Val Phe Ile Phe Pro Pro
            195                 200                 205

Lys Ile Lys Asp Val Leu Met Ile Ser Leu Ser Pro Ile Val Thr Cys
210                 215                 220

Val Val Val Asp Val Ser Glu Asp Pro Asp Val Gln Ile Ser Trp
225                 230                 235                 240

Phe Val Asn Asn Val Glu Val His Thr Ala Gln Thr Gln Thr His Arg
                245                 250                 255

Glu Asp Tyr Asn Ser Thr Leu Arg Val Val Ser Ala Leu Pro Ile Gln
            260                 265                 270

His Gln Asp Trp Met Ser Gly Lys Glu Phe Lys Cys Lys Val Asn Asn
        275                 280                 285

Lys Asp Leu Pro Ala Pro Ile Glu Arg Thr Ile Ser Lys Pro Lys Gly
290                 295                 300

Ser Val Arg Ala Pro Gln Val Tyr Val Leu Pro Pro Glu Glu Glu
305                 310                 315                 320

Met Thr Lys Lys Gln Val Thr Leu Thr Cys Met Val Thr Asp Phe Met
                325                 330                 335

Pro Glu Asp Ile Tyr Val Glu Trp Thr Asn Asn Gly Lys Thr Glu Leu
            340                 345                 350

Asn Tyr Lys Asn Thr Glu Pro Val Leu Asp Ser Asp Gly Ser Tyr Phe
        355                 360                 365

Met Tyr Ser Lys Leu Arg Val Glu Lys Lys Asn Trp Val Glu Arg Asn
370                 375                 380

Ser Tyr Ser Cys Ser Val Val His Glu Gly Leu His Asn His His Thr
385                 390                 395                 400

Thr Lys Ser Phe Ser Arg Thr Pro Gly Lys
                405                 410

<210> SEQ ID NO 342
<211> LENGTH: 460
<212> TYPE: PRT
<213> ORGANISM: Artificial Sequence
<220> FEATURE:
<223> OTHER INFORMATION: Description of Artificial Sequence: Synthetic
      hANGPTL3 polypeptide

<400> SEQUENCE: 342

Met Phe Thr Ile Lys Leu Leu Leu Phe Ile Val Pro Leu Val Ile Ser
1               5                   10                  15

Ser Arg Ile Asp Gln Asp Asn Ser Ser Phe Asp Ser Leu Ser Pro Glu
            20                  25                  30

Pro Lys Ser Arg Phe Ala Met Leu Asp Asp Val Lys Ile Leu Ala Asn
        35                  40                  45

Gly Leu Leu Gln Leu Gly His Gly Leu Lys Asp Phe Val His Lys Thr
    50                  55                  60

Lys Gly Gln Ile Asn Asp Ile Phe Gln Lys Leu Asn Ile Phe Asp Gln
65                  70                  75                  80

Ser Phe Tyr Asp Leu Ser Leu Gln Thr Ser Glu Ile Lys Glu Glu Glu
                85                  90                  95

Lys Glu Leu Arg Arg Thr Thr Tyr Lys Leu Gln Val Lys Asn Glu Glu
            100                 105                 110

Val Lys Asn Met Ser Leu Glu Leu Asn Ser Lys Leu Glu Ser Leu Leu
        115                 120                 125

Glu Glu Lys Ile Leu Leu Gln Gln Lys Val Lys Tyr Leu Glu Glu Gln
    130                 135                 140
```

```
Leu Thr Asn Leu Ile Gln Asn Gln Pro Glu Thr Pro Glu His Pro Glu
145                 150                 155                 160

Val Thr Ser Leu Lys Thr Phe Val Glu Lys Gln Asp Asn Ser Ile Lys
            165                 170                 175

Asp Leu Leu Gln Thr Val Glu Asp Gln Tyr Lys Gln Leu Asn Gln Gln
        180                 185                 190

His Ser Gln Ile Lys Glu Ile Glu Asn Gln Leu Arg Arg Thr Ser Ile
    195                 200                 205

Gln Glu Pro Thr Glu Ile Ser Leu Ser Ser Lys Pro Arg Ala Pro Arg
210                 215                 220

Thr Thr Pro Phe Leu Gln Leu Asn Glu Ile Arg Asn Val Lys His Asp
225                 230                 235                 240

Gly Ile Pro Ala Glu Cys Thr Thr Ile Tyr Asn Arg Gly Glu His Thr
                245                 250                 255

Ser Gly Met Tyr Ala Ile Arg Pro Ser Asn Ser Gln Val Phe His Val
            260                 265                 270

Tyr Cys Asp Val Ile Ser Gly Ser Pro Trp Thr Leu Ile Gln His Arg
        275                 280                 285

Ile Asp Gly Ser Gln Asn Phe Asn Glu Thr Trp Glu Asn Tyr Lys Tyr
290                 295                 300

Gly Phe Gly Arg Leu Asp Gly Glu Phe Trp Leu Gly Leu Glu Lys Ile
305                 310                 315                 320

Tyr Ser Ile Val Lys Gln Ser Asn Tyr Val Leu Arg Ile Glu Leu Glu
                325                 330                 335

Asp Trp Lys Asp Asn Lys His Tyr Ile Glu Tyr Ser Phe Tyr Leu Gly
            340                 345                 350

Asn His Glu Thr Asn Tyr Thr Leu His Leu Val Ala Ile Thr Gly Asn
        355                 360                 365

Val Pro Asn Ala Ile Pro Glu Asn Lys Asp Leu Val Phe Ser Thr Trp
370                 375                 380

Asp His Lys Ala Lys Gly His Phe Asn Cys Pro Glu Gly Tyr Ser Gly
385                 390                 395                 400

Gly Trp Trp Trp His Asp Glu Cys Gly Glu Asn Asn Leu Asn Gly Lys
                405                 410                 415

Tyr Asn Lys Pro Arg Ala Lys Ser Lys Pro Glu Arg Arg Arg Gly Leu
            420                 425                 430

Ser Trp Lys Ser Gln Asn Gly Arg Leu Tyr Ser Ile Lys Ser Thr Lys
        435                 440                 445

Met Leu Ile His Pro Thr Asp Ser Glu Ser Phe Glu
    450                 455                 460
```

<210> SEQ ID NO 343
<211> LENGTH: 1383
<212> TYPE: DNA
<213> ORGANISM: Artificial Sequence
<220> FEATURE:
<223> OTHER INFORMATION: Description of Artificial Sequence: Synthetic
      hANGPTL3 polynucleotide

<400> SEQUENCE: 343
atgttcacaa ttaagctcct tcttttttatt gttcctctag ttatttcctc cagaattgat      60
caagacaatt catcatttga ttctctatct ccagagccaa atcaagatt tgctatgtta     120 gacgatgtaa aaattttagc caatggcctc cttcagttgg acatggtct taaagacttt     180 gtccataaga cgaagggcca aattaatgac atatttcaaa aactcaacat atttgatcag     240

-continued

```
tcttttatg atctatcgct gcaaaccagt gaaatcaaag aagaagaaaa ggaactgaga    300
agaactacat ataaactaca agtcaaaaat gaagaggtaa agaatatgtc acttgaactc    360
aactcaaaac ttgaaagcct cctagaagaa aaaattctac ttcaacaaaa agtgaaatat    420
ttagaagagc aactaactaa cttaattcaa aatcaacctg aaactccaga acacccagaa    480
gtaacttcac ttaaaacttt tgtagaaaaa caagataata gcatcaaaga ccttctccag    540
accgtggaag accaatataa acaattaaac caacagcata gtcaaataaa agaaatagaa    600
aatcagctca gaaggactag tattcaagaa cccacagaaa tttctctatc ttccaagcca    660
agagcaccaa gaactactcc ctttcttcag ttgaatgaaa taagaaatgt aaaacatgat    720
ggcattcctg ctgaatgtac caccatttat aacagaggtg aacatacaag tggcatgtat    780
gccatcagac ccagcaactc tcaagttttt catgtctact gtgatgttat atcaggtagt    840
ccatggacat taattcaaca tcgaatagat ggatcacaaa acttcaatga aacgtgggag    900
aactacaaat atggttttgg gaggcttgat ggagaatttt ggttgggcct agagaagata    960
tactccatag tgaagcaatc taattatgtt ttacgaattg agttggaaga ctggaaagac   1020
aacaaacatt atattgaata ttctttttac ttgggaaatc acgaaaccaa ctatacgcta   1080
catctagttg cgattactgg caatgtcccc aatgcaatcc cggaaaacaa agatttggtg   1140
ttttctactt gggatcacaa agcaaaagga cacttcaact gtccagaggg ttattcagga   1200
ggctggtggt ggcatgatga gtgtggagaa aacaacctaa atggtaaata taacaaacca   1260
agagcaaaat ctaagccaga gaggagaaga ggattatctt ggaagtctca aaatggaagg   1320
ttatactcta taaaatcaac caaaatgttg atccatccaa cagattcaga aagctttgaa   1380
tga                                                                  1383
```

<210> SEQ ID NO 344
<211> LENGTH: 406
<212> TYPE: PRT
<213> ORGANISM: Artificial Sequence
<220> FEATURE:
<223> OTHER INFORMATION: Description of Artificial Sequence: Synthetic
      hANGPTL4 polypeptide

<400> SEQUENCE: 344

```
Met Ser Gly Ala Pro Thr Ala Gly Ala Ala Leu Met Leu Cys Ala Ala
1               5                   10                  15

Thr Ala Val Leu Leu Ser Ala Gln Gly Gly Pro Val Gln Ser Lys Ser
            20                  25                  30

Pro Arg Phe Ala Ser Trp Asp Glu Met Asn Val Leu Ala His Gly Leu
        35                  40                  45

Leu Gln Leu Gly Gln Gly Leu Arg Glu His Ala Glu Arg Thr Arg Ser
    50                  55                  60

Gln Leu Ser Ala Leu Glu Arg Arg Leu Ser Ala Cys Gly Ser Ala Cys
65                  70                  75                  80

Gln Gly Thr Glu Gly Ser Thr Asp Leu Pro Leu Ala Pro Glu Ser Arg
                85                  90                  95

Val Asp Pro Glu Val Leu His Ser Leu Gln Thr Gln Leu Lys Ala Gln
            100                 105                 110

Asn Ser Arg Ile Gln Gln Leu Phe His Lys Val Ala Gln Gln Gln Arg
        115                 120                 125

His Leu Glu Lys Gln His Leu Arg Ile Gln His Leu Gln Ser Gln Phe
    130                 135                 140
```

Gly Leu Leu Asp His Lys His Leu Asp His Glu Val Ala Lys Pro Ala
145                 150                 155                 160

Arg Arg Lys Arg Leu Pro Glu Met Ala Gln Pro Val Asp Pro Ala His
            165                 170                 175

Asn Val Ser Arg Leu His Arg Leu Pro Arg Asp Cys Gln Glu Leu Phe
        180                 185                 190

Gln Val Gly Glu Arg Gln Ser Gly Leu Phe Glu Ile Gln Pro Gln Gly
    195                 200                 205

Ser Pro Pro Phe Leu Val Asn Cys Lys Met Thr Ser Asp Gly Gly Trp
210                 215                 220

Thr Val Ile Gln Arg Arg His Asp Gly Ser Val Asp Phe Asn Arg Pro
225                 230                 235                 240

Trp Glu Ala Tyr Lys Ala Gly Phe Gly Asp Pro His Gly Glu Phe Trp
            245                 250                 255

Leu Gly Leu Glu Lys Val His Ser Ile Thr Gly Asp Arg Asn Ser Arg
        260                 265                 270

Leu Ala Val Gln Leu Arg Asp Trp Asp Gly Asn Ala Glu Leu Leu Gln
    275                 280                 285

Phe Ser Val His Leu Gly Gly Glu Asp Thr Ala Tyr Ser Leu Gln Leu
290                 295                 300

Thr Ala Pro Val Ala Gly Gln Leu Gly Ala Thr Thr Val Pro Pro Ser
305                 310                 315                 320

Gly Leu Ser Val Pro Phe Ser Thr Trp Asp Gln Asp His Asp Leu Arg
            325                 330                 335

Arg Asp Lys Asn Cys Ala Lys Ser Leu Ser Gly Gly Trp Trp Phe Gly
        340                 345                 350

Thr Cys Ser His Ser Asn Leu Asn Gly Gln Tyr Phe Arg Ser Ile Pro
    355                 360                 365

Gln Gln Arg Gln Lys Leu Lys Lys Gly Ile Phe Trp Lys Thr Trp Arg
370                 375                 380

Gly Arg Tyr Tyr Pro Leu Gln Ala Thr Thr Met Leu Ile Gln Pro Met
385                 390                 395                 400

Ala Ala Glu Ala Ala Ser
            405

<210> SEQ ID NO 345
<211> LENGTH: 1221
<212> TYPE: DNA
<213> ORGANISM: Artificial Sequence
<220> FEATURE:
<223> OTHER INFORMATION: Description of Artificial Sequence: Synthetic
      hANGPTL4 polynucleotide

<400> SEQUENCE: 345
atgagcggtg ctccgacggc cggggcagcc ctgatgctct cgccgccac cgccgtgcta      60 ctgagcgctc agggcggacc cgtgcagtcc aagtcgccgc gctttgcgtc ctgggacgag     120
atgaatgtcc tggcgcacgg actcctgcag ctcggccagg ggctgcgcga acacgcggag    180
cgcacccgca gtcagctgag cgcgctggag cggcgcctga gcgcgtgcgg gtccgcctgt    240
cagggaaccg aggggtccac cgacctcccg ttagcccctg agagccgggt ggaccctgag    300
gtccttcaca gcctgcagac acaactcaag gctcagaaca gcaggatcca gcaactcttc    360
cacaaggtgg cccagcagca gcggcacctg gagaagcagc acctgcgaat tcagcatctg    420
caaagccagt ttggcctcct ggaccacaag cacctagacc atgaggtggc caagcctgcc    480
cgaagaaaga ggctgcccga gatggcccag ccagttgacc cggctcacaa tgtcagccgc    540

```
ctgcaccggc tgcccaggga ttgccaggag ctgttccagg ttggggagag gcagagtgga    600
ctatttgaaa tccagcctca ggggtctccg ccatttttgg tgaactgcaa gatgacctca    660
gatggaggct ggacagtaat tcagaggcgc acgatggct cagtggactt caaccggccc     720
tgggaagcct acaaggcggg gtttggggat ccccacggcg agttctggct gggtctggag    780
aaggtgcata gcatcacggg ggaccgcaac agccgcctgg ccgtgcagct gcgggactgg    840
gatggcaacg ccgagttgct gcagttctcc gtgcacctgg gtggcgagga cacggcctat    900
agcctgcagc tcactgcacc cgtggccggc cagctgggcg ccaccaccgt cccacccagc    960
ggcctctccg tacccttctc cacttgggac caggatcacg acctccgcag ggacaagaac   1020
tgcgccaaga gcctctctgg aggctggtgg tttggcacct gcagccattc aacctcaac    1080 ggccagtact ccgctccat cccacagcag cggcagaagc ttaagaaggg aatcttctgg    1140
aagacctggc ggggccgcta ctacccgctg caggccacca ccatgttgat ccagcccatg   1200
gcagcagagg cagcctccta g                                              1221
```

<210> SEQ ID NO 346
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Cys Gly Gly Cys Gly Gly
1               5

<210> SEQ ID NO 347
<211> LENGTH: 177
<212> TYPE: PRT
<213> ORGANISM: Homo sapiens

<400> SEQUENCE: 347

Ala Pro Met Gly Gly Pro Glu Leu Ala Gln His Glu Glu Leu Thr Leu
1               5                   10                  15

Leu Phe His Gly Thr Leu Gln Leu Gly Gln Ala Leu Asn Gly Val Tyr
            20                  25                  30

Arg Thr Thr Glu Gly Arg Leu Thr Lys Ala Arg Asn Ser Leu Gly Leu
        35                  40                  45

Tyr Gly Arg Thr Ile Glu Leu Leu Gly Gln Glu Val Ser Arg Gly Arg
    50                  55                  60

Asp Ala Ala Gln Glu Leu Arg Ala Ser Leu Leu Glu Thr Gln Met Glu
65                  70                  75                  80

Glu Asp Ile Leu Gln Leu Gln Ala Glu Ala Thr Ala Glu Val Leu Gly
                85                  90                  95

Glu Val Ala Gln Ala Gln Lys Val Leu Arg Asp Ser Val Gln Arg Leu
            100                 105                 110

Glu Val Gln Leu Arg Ser Ala Trp Leu Gly Pro Ala Tyr Arg Glu Phe
        115                 120                 125

Glu Val Leu Lys Ala His Ala Asp Lys Gln Ser His Ile Leu Trp Ala
    130                 135                 140

Leu Thr Gly His Val Gln Arg Gln Arg Glu Met Val Ala Gln Gln
145                 150                 155                 160

His Arg Leu Arg Gln Ile Gln Glu Arg Leu His Thr Ala Ala Leu Pro
                165                 170                 175

Ala

<210> SEQ ID NO 348
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Ala Pro Met Gly Gly Pro Glu Leu Ala Gln His Glu Glu Leu Thr
1               5                   10                  15

<210> SEQ ID NO 349
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Pro Met Gly Gly Pro Glu Leu Ala Gln His Glu Glu Leu Thr Leu
1               5                   10                  15

<210> SEQ ID NO 350
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Met Gly Gly Pro Glu Leu Ala Gln His Glu Glu Leu Thr Leu Leu
1               5                   10                  15

<210> SEQ ID NO 351
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Gly Gly Pro Glu Leu Ala Gln His Glu Glu Leu Thr Leu Leu Phe
1               5                   10                  15

<210> SEQ ID NO 352
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Gly Pro Glu Leu Ala Gln His Glu Glu Leu Thr Leu Leu Phe His
1               5                   10                  15

<210> SEQ ID NO 353
<211> LENGTH: 15
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 353

Pro Glu Leu Ala Gln His Glu Glu Leu Thr Leu Leu Phe His Gly
1               5                   10                  15

<210> SEQ ID NO 354
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Glu Leu Ala Gln His Glu Glu Leu Thr Leu Leu Phe His Gly Thr
1               5                   10                  15

<210> SEQ ID NO 355
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Leu Ala Gln His Glu Glu Leu Thr Leu Leu Phe His Gly Thr Leu
1               5                   10                  15

<210> SEQ ID NO 356
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Ala Gln His Glu Glu Leu Thr Leu Leu Phe His Gly Thr Leu Gln
1               5                   10                  15

<210> SEQ ID NO 357
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Gln His Glu Glu Leu Thr Leu Leu Phe His Gly Thr Leu Gln Leu
1               5                   10                  15

<210> SEQ ID NO 358
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Thr Ala Glu Val Leu Gly Glu Val Ala Ala Gly Gln Lys Val Leu
1               5                   10                  15

```
<210> SEQ ID NO 359
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

Val Tyr Arg Thr Thr Glu Gly Arg Leu Ala Ala Ala Arg Asn Ser
1               5                   10                  15

<210> SEQ ID NO 360
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Gly Val Tyr Arg Thr Thr Glu Gly Arg Ala Ala Lys Ala Arg Asn
1               5                   10                  15

<210> SEQ ID NO 361
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Val Gln Arg Leu Glu Val Gln Leu Arg Ala Gly Trp Leu Gly Pro
1               5                   10                  15

<210> SEQ ID NO 362
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Leu Thr Gly His Val Gln Arg Gln Arg Ala Ala Met Val Ala Gln
1               5                   10                  15

<210> SEQ ID NO 363
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Val Leu Lys Ala His Ala Asp Lys Gln Ala Ala Ile Leu Trp Ala
1               5                   10                  15

<210> SEQ ID NO 364
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364
```

```
Leu Arg Asp Ser Val Gln Arg Leu Glu Ala Ala Leu Arg Ser Ala
1               5                   10                  15

<210> SEQ ID NO 365
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Arg Arg Glu Met Val Ala Gln Gln His Ala Ala Arg Gln Ile Gln
1               5                   10                  15

<210> SEQ ID NO 366
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Val Ser Arg Gly Arg Asp Ala Ala Gln Ala Ala Arg Ala Ser Leu
1               5                   10                  15

<210> SEQ ID NO 367
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Ala Tyr Arg Glu Phe Glu Val Leu Lys Gly Ala Ala Asp Lys Gln
1               5                   10                  15

<210> SEQ ID NO 368
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Gln Arg Gln Arg Arg Glu Met Val Ala Gln
1               5                   10
```

METHODS OF TREATING OBESITY WITH ANTI-ANGPTL8 ANTIBODIES

CROSS-REFERENCE TO RELATED APPLICATIONS

This application claims the benefit under 35 U.S.C. § 119(e) of U.S. provisional application No. 62/423,639, filed on Nov. 17, 2016, the disclosure of which is herein incorporated by reference in its entirety.

SEQUENCE STATEMENT

The instant application contains a Sequence Listing, which has been submitted electronically in ASCII format and is hereby incorporated by reference in its entirety. Said ASCII copy, created on Nov. 15, 2017, is named SequenceList_30.TXT and is 158 kilobytes in size.

FIELD OF THE INVENTION

The present invention relates to antibodies, and antigen-binding fragments thereof, which specifically bind angiopoietin-like protein (ANGPTL) 8, compositions comprising these antibodies and methods of use thereof.

BACKGROUND

ANGPTL8 (alternatively called TD26, RIFL, Lipasin, C19orf80 and Betatrophin) is a newly recognized ANGPTL family member that has been implicated in both triglyceride (TG) and glucose metabolism. It is a circulating protein that is expressed primarily in liver and adipose tissue. Unlike ANGPTL3 and ANGPTL4, ANGPTL8 lacks a fibrinogen like domain at the C-terminus, but contains an N-terminal coiled-coil domain, much like other ANGPTL family members. Phylogenetic analysis reveals that ANGPTL8 shares common ancestors with ANGPTL3 and ANGPTL4 (Fu, Z. et. al., (2013), Biochem. Biophys. Res. Commun. 430:1126-1131).

Hepatic overexpression of ANGPTL8 is associated with hypertriglyceridemia, whereas inactivation of Angptl8 causes a reduction in plasma TG levels (Quagliarini, F. et. al. (2012), Proc. Natl. Acad. Sci. USA 109(48):19751-19756; Wang, Y. et. al. (2013), Proc. Natl. Acad. Sci. USA 110: 16109-16114). Despite the consensus that ANGPTL8 is involved in lipid regulation, the mechanism responsible for this process is still under debate. One proposed mechanism is that ANGPTL8 inhibits lipoprotein lipase (LPL) activity, resulting in reduced triglyceride hydrolysis and clearance (Zhang, R. et. al., (2012), Biochem. Biophys. Res. Commun. 424:786-792).

ANGPTL8 has also been reported to play a role in beta cell proliferation and beta cell mass in mice, where insulin resistance was induced by an insulin receptor antagonist, S961 (Yi, P. et. al. (2013), Cell 153:747-758). However, subsequent studies revealed that ANGPTL8 is not required for beta cell function, or the beta cell growth response to insulin resistance. Furthermore, overexpression of ANGPTL8 does not increase beta cell area or improve glycemic control (Gusarova, V. et. al. (2014) Cell 159:691-696).

Since hepatic overexpression of ANGPTL8 is associated with hypertriglyceridemia and since inactivation of Angptl8 results in a reduction in plasma triglyceride levels, an inhibitor or antagonist of ANGPTL8 may prove effective in treating a disease characterized in part by elevated levels of triglycerides, such as, but not limited to, hypertriglyceridemia.

Zhang reported that a monoclonal antibody to lipasin, when injected intraperitoneally to wildtype mice, decreased serum triglyceride levels (Zhang, R. (2015), Endocrine Society's 97$^{th}$ Annual Meeting, Presentation No. OR13-6, March 5-8, San Diego, Calif.). However, no fully human antibodies specific for ANGPTL8 have been described to date that may be used in a clinical setting to treat diseases, or conditions characterized by elevated levels of triglycerides, including hypertriglyceridemia.

Accordingly, there is a need in the art for novel antagonists of ANGPTL8, such as the antibodies described herein, for treating patients suffering from hypertriglyceridemia and other disorders or conditions associated with elevated triglyceride and lipid levels.

BRIEF SUMMARY OF THE INVENTION

The present invention provides antibodies and antigen-binding fragments thereof that bind to angiopoietin-like protein 8 (ANGPTL8). One aspect of the invention provides human antibodies and antigen-binding fragments thereof that bind to/interact with ANGPTL8, whereby such binding and/or interaction results in the lowering of triglyceride levels in a mammal.

Accordingly, in a first aspect, the invention provides fully human monoclonal antibodies (mAbs) and antigen-binding fragments thereof that specifically bind, neutralize, inhibit, block, abrogate, reduce, or interfere with, at least one activity of ANGTPL8, in particular, human ANGPTL8 (amino acids 22-198 of GenBank accession number NP_061157.3=amino acids 1-177 of SEQ ID NO:340). The activity of ANGPTL8 that can be neutralized, inhibited, blocked, abrogated, reduced or interfered with, by an antibody or antigen-binding fragment thereof of the invention, includes, but is not limited to, the inhibition of LPL activity by ANGPTL8.

In one embodiment, the invention provides a monoclonal antibody or antigen-binding fragment thereof that specifically binds to ANGPTL8 and neutralizes, or inhibits at least one activity associated with ANGPTL8, wherein the antibody or antigen-binding fragment thereof exhibits one or more of the following characteristics:

a) is a fully human monoclonal antibody;
b) binds specifically to a linear epitope in the N-terminal region of human ANGPTL8 as defined by SEQ ID NO: 337;
c) does not bind to a linear epitope in the N-terminal region of human ANGPTL8 as defined by SEQ ID NO: 337;
d) does not bind to the N-terminal coiled-coil region of human ANGPTL3 peptide of SEQ ID NO: 338, or to the N-terminal coiled-coil region of human ANGPTL4 peptide of SEQ ID NO: 339;
e) binds human ANGPTL8 at 25° C. with a $K_D$ of less than about 150 pM and binds monkey ANGPTL8 at 25° C. with a $K_D$ of less than about 90 pM as measured by surface plasmon resonance;
f) lowers triglyceride levels in a mammal by about 68% (maximum) when administered subcutaneously at a dose of about 10 mg/kg;
g) lowers triglyceride levels in a mammal for a period ranging from about 7 days to 21 days, when administered subcutaneously at doses ranging from about 5 mg/kg to about 25 mg/kg;
h) comprises a heavy chain variable region (HCVR) having an amino acid sequence selected from the group consisting of SEQ ID NO: 2, 18, 34, 50, 66, 82, 98, 114, 130, 146, 162, 178, 194, 210, 226, 242, 258, 266, 274, 282, 290, 298, 306, 314 and 330;

i) comprises a light chain variable region (LCVR) having an amino acid sequence selected from the group consisting of SEQ ID NO: 10, 26, 42, 58, 74, 90, 106, 122, 138, 154, 170, 186, 202, 218, 234, 250, and 322; or j) cross-competes with a reference antibody, wherein the reference antibody comprises a heavy chain variable region (HCVR) and a light chain variable region (LCVR) amino acid sequence selected from the group consisting of any of the HCVR and LCVR amino acid sequences of Table 1.

In one embodiment, an antibody or antigen-binding fragment thereof of the present invention can neutralize, inhibit, block, abrogate, reduce or interfere with, an activity of hANGPTL8 by binding to an epitope of hANGPTL8 that is directly involved in the targeted activity of hANGPTL8 (e.g. the LPL inhibitory activity of ANGPTL8). In another embodiment, the antibody or antigen-binding fragment thereof of the present invention improves triglyceride clearance.

In another embodiment, an antibody or antigen-binding fragment thereof of the invention can neutralize, inhibit, block, abrogate, reduce or interfere with, an activity of hANGPTL8 by binding to an epitope of hANGPTL8 that is not directly involved in the targeted activity of hANGPTL8, but the antibody or fragment binding thereto may either by steric overlap or by allosteric effects at sites different from the antibody-antigen contact surface inhibit, block, abrogate, reduce or interfere with, the targeted activity of hANGPTL8.

In another embodiment, an antibody or fragment thereof of the invention binds to an epitope of hANGPTL8 that is not directly involved in the targeted activity (e.g., inhibiting LPL activity, and the like) of hANGPTL8 (i.e., a non-blocking antibody), but the antibody or fragment thereof results in lowering of triglyceride levels in vivo, compared to the lowering of triglyceride levels in the absence of the antibody or fragment thereof.

In one embodiment, the invention features an isolated anti-hANGPTL8 antibody or antigen-binding fragment thereof that binds to an epitope situated within the N-terminal region at residues 1-39 of SEQ ID NO: 340 (shown also as SEQ ID NO: 337).

In another embodiment, the invention provides an isolated antibody or antigen-binding fragment of an antibody that binds to an epitope situated within the N-terminal region of human ANGPTL8 at residues 1-39 of SEQ ID NO: 340 (shown also as SEQ ID NO: 337), but does not bind to the N-terminal coiled-coil region of hANGPTL3 (SEQ ID NO:338), or to the N-terminal coiled-coil region of hANGPTL4 (SEQ ID NO:339).

In one embodiment, the invention features an isolated anti-hANGPTL8 antibody or antigen-binding fragment thereof that binds to an epitope situated outside of the region of human ANGPTL8 defined by amino acid residues 1-39 of SEQ ID NO: 340 (shown also as SEQ ID NO: 337), i.e. amino acid residues 40-177 of SEQ ID NO: 340), and neutralizes, inhibits, abrogates, reduces or interferes with, at least one activity of hANGPTL8.

In one embodiment, the invention features an isolated anti-hANGPTL8 antibody or antigen-binding fragment thereof that binds to human ANGPTL8 (amino acid residues 1-177 of SEQ ID NO: 340; See also amino acid residues 22-198 of GenBank accession number NP_061157.3), but does not cross react with a related protein, such as human ANGPTL3 (amino acid sequence of SEQ ID NO: 342, encoded by the nucleic acid sequence shown in SEQ ID NO: 343), or human ANGPTL4 (amino acid sequence of SEQ ID NO: 344, encoded by the nucleic acid sequence shown in SEQ ID NO:345).

The antibodies of the invention can be full-length (for example, an IgG1 or IgG4 antibody) or may comprise only an antigen-binding portion (for example, a Fab, F(ab')$_2$ or scFv fragment), and may be modified to affect functionality, e.g., to increase persistence in the host or to eliminate residual effector functions (Reddy et al., 2000, J. Immunol. 164:1925-1933). In certain embodiments, the antibodies may be bispecific.

Exemplary anti-ANGPTL8 antibodies of the present invention are listed in Tables 1 and 2 herein. Table 1 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of exemplary anti-ANGPTL8 antibodies. Table 2 sets forth the nucleic acid sequence identifiers of the HCVRs, LCVRs, HCDR1, HCDR2 HCDR3, LCDR1, LCDR2 and LCDR3 of the exemplary anti-ANGPTL8 antibodies.

The present invention provides antibodies, or antigen-binding fragments thereof, comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

The present invention also provides antibodies, or antigen-binding fragments thereof, comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

The present invention also provides antibodies, or antigen-binding fragments thereof, comprising an HCVR and an LCVR amino acid sequence pair (HCVR/LCVR) comprising any of the HCVR amino acid sequences listed in Table 1 paired with any of the LCVR amino acid sequences listed in Table 1.

In one embodiment, the invention provides an isolated antibody or antigen-binding fragment thereof that binds specifically to and/or inhibits at least one activity associated with ANGPTL8, wherein the antibody or antigen-binding fragment comprises a HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/250, 266/250, 274/250, 282/250, 290/250, 306/250, 314/322, and 330/322.

In one embodiment, the invention provides an isolated antibody or antigen-binding fragment thereof that binds specifically to and/or inhibits at least one activity associated with ANGPTL8, wherein the antibody or antigen-binding fragment comprises a HCVR/LCVR amino acid sequence pair selected from the group consisting of SEQ ID NOs: 66/74, 162/170, 194/202 and 314/322.

In one embodiment, the invention provides an isolated antibody or antigen-binding fragment thereof that binds specifically to and/or inhibits at least one activity associated with ANGPTL8, wherein the antibody or antigen-binding fragment comprises the HCVR/LCVR amino acid sequence pair of SEQ ID NOs: 162/170.

In one embodiment, the invention provides an isolated antibody or antigen-binding fragment thereof that binds to and/or inhibits at least one activity associated with ANGPTL8, wherein the antibody or antigen-binding fragment comprises: (a) three heavy chain complementarity determining regions (CDRs) (HCDR1, HCDR2 and HCDR3) contained within any one of the heavy chain variable region (HCVR) sequences as set forth in Table 1; and (b) three light chain CDRs (LCDR1, LCDR2 and LCDR3) contained within any one of the light chain variable region (LCVR) sequences as set forth in Table 1.

In one embodiment, the invention provides an isolated antibody or antigen-binding fragment thereof that binds specifically to and/or inhibits at least one activity associated with ANGPTL8, wherein the antibody or antigen-binding fragment comprises:

(a) a HCDR1 domain having an amino acid sequence selected from the group consisting of SEQ ID NOs: 4, 20, 36, 52, 68, 84, 100, 116, 132, 148, 164, 180, 196, 212, 228, 244, 260, 268, 276, 284, 292, 300, 308, 316 and 332;

(b) a HCDR2 domain having an amino acid sequence selected from the group consisting of SEQ ID NOs: 6, 22, 38, 54, 70, 86, 102, 118, 134, 150, 166, 182, 198, 214, 230, 246, 262, 270, 278, 286, 294, 302, 310, 318, and 334;

(c) a HCDR3 domain having an amino acid sequence selected from the group consisting of SEQ ID NOs: 8, 24, 40, 56, 72, 88, 104, 120, 136, 152, 168, 184, 200, 216, 232, 248, 264, 272, 280, 288, 296, 304, 312, 320 and 336;

(d) a LCDR1 domain having an amino acid sequence selected from the group consisting of SEQ ID NOs: 12, 28, 44, 60, 76, 92, 108, 124, 140, 156, 172, 188, 204, 220, 236, 252 and 324;

(e) a LCDR2 domain having an amino acid sequence selected from the group consisting of SEQ ID NOs: 14, 30, 46, 62, 78, 94, 110, 126, 142, 158, 174, 190, 206, 222, 238, 254, and 326; and (f) a LCDR3 domain having an amino acid sequence selected from the group consisting of SEQ ID NOs: 16, 32, 48, 64, 80, 96, 112, 128, 144, 160, 176, 192, 208, 224, 240, 256 and 328.

The present invention also provides antibodies, or antigen-binding fragments thereof, comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity.

The present invention also provides antibodies, or antigen-binding fragments thereof, comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present invention provides antibodies, or antigen-binding fragments thereof, comprising an HCDR3/LCDR3 amino acid sequence pair contained within any of the exemplary anti-ANGPTL8 antibodies listed in Table 1. In certain embodiments, the HCDR3/LCDR3 amino acid sequence pair is selected from the group consisting of SEQ ID NOs: 72/80 (e.g., H4H15321P), 168/176 (e.g., H4H15341P), 200/208 (e.g., H4H15345P), and 320/328 (e.g., H4H15367P2). In one embodiment, the HCDR3/LCDR3 amino acid sequence pair is SEQ ID NO: 168/176 (e.g., H4H15341P).

The present invention also provides antibodies, or antigen-binding fragments thereof, comprising a set of six CDRs (i.e., HCDR1-HCDR2-HCDR3-LCDR1-LCDR2-LCDR3) contained within any of the exemplary anti-ANGPTL8 antibodies listed in Table 1. In certain embodiments, the HCDR1-HCDR2-HCDR3-LCDR1-LCDR2-LCDR3 amino acid sequence set is selected from the group consisting of SEQ ID NOs: 68-70-72-76-78-80 (e.g., H4H15321P); 164-166-168-172-174-176 (e.g., H4H15341P); 196-198-200-204-206-208 (e.g., H4H15345P); 316-318-320-324-326-328 (e.g., H4H15367P2). In one embodiment, the HCDR1-HCDR2-HCDR3-LCDR1-LCDR2-LCDR3 amino acid sequence set is SEQ ID NOs: 164-166-168-172-174-176 (e.g., H4H15341P).

In a related embodiment, the present invention provides antibodies, or antigen-binding fragments thereof, comprising a set of six CDRs (i.e., HCDR1-HCDR2-HCDR3-LCDR1-LCDR2-LCDR3) contained within an HCVR/LCVR amino acid sequence pair as defined by any of the exemplary anti-ANGPTL8 antibodies listed in Table 1. For example, the present invention includes antibodies, or antigen-binding fragments thereof, comprising the HCDR1-HCDR2-HCDR3-LCDR1-LCDR2-LCDR3 amino acid sequences set contained within an HCVR/LCVR amino acid sequence pair selected from the group consisting of SEQ ID NOs: 66/74 (e.g., H4H15321P), 162/170 (e.g., H4H15341P); 194/202 (e.g., H4H15345P); 314/322 (e.g., H415367P2). Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches.

See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

The present invention includes anti-ANGPTL8 antibodies having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

The present invention also provides for antibodies and antigen-binding fragments thereof that compete for specific binding to ANGPTL8 with a reference antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

In one embodiment, the invention provides an isolated monoclonal antibody or antigen-binding fragment thereof that competes for binding to ANGPTL8 with a reference antibody comprising an HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/250, 266/250, 274/250, 282/250, 290/250, 306/250, 314/322, and 330/322.

The present invention also provides antibodies and antigen-binding fragments thereof that bind the same epitope on ANGPTL8 as a reference antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

In one embodiment, the invention provides an isolated monoclonal antibody or antigen-binding fragment thereof that binds to the same epitope on ANGPTL8 as a reference antibody comprising an HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/250, 266/250, 274/250, 282/250, 290/250, 306/250, 314/322, and 330/322.

In one embodiment, the isolated antibody that binds specifically to and/or inhibits at least one activity associated with ANGPTL8, is a recombinantly produced human monoclonal antibody.

In one embodiment, the isolated antibody that binds specifically to and/or inhibits at least one activity associated with ANGPTL8, is a recombinantly produced human monoclonal antibody having a HCVR and/or an LCVR sequence selected from the amino acid sequences found in Table 1.

In one embodiment, the isolated antibody that binds specifically to and/or inhibits at least one activity associated with ANGPTL8, is a recombinantly produced human monoclonal antibody having a HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/250, 266/250, 274/250, 282/250, 290/250, 306/250, 314/322, and 330/322.

In one embodiment, the invention provides a fully human monoclonal antibody or antigen-binding fragment thereof that neutralizes ANGPTL8 activity, wherein the antibody or fragment thereof exhibits one or more of the following characteristics: (i) comprises a HCVR having an amino acid sequence selected from the group consisting of SEQ ID NO: 2, 18, 34, 50, 66, 82, 98, 114, 130, 146, 162, 178, 194, 210, 226, 242, 258, 266, 274, 282, 290, 298, 306, 314 and 330; (ii) comprises a LCVR having an amino acid sequence selected from the group consisting of SEQ ID NO: 10, 26, 42, 58, 74, 90, 106, 122, 138, 154, 170, 186, 202, 218, 234, 250, and 322; (iii) comprises a HCDR3 domain having an amino acid sequence selected from the group consisting of SEQ ID NOs: 8, 24, 40, 56, 72, 88, 104, 120, 136, 152, 168, 184, 200, 216, 232, 248, 264, 272, 280, 288, 296, 304, 312, 320 and 336, or a substantially similar sequence thereof having at least 90%, at least 95%, at least 98% or at least 99% sequence identity; and a LCDR3 domain having an amino acid sequence selected from the group consisting of SEQ ID NOs: 16, 32, 48, 64, 80, 96, 112, 128, 144, 160, 176, 192, 208, 224, 240, 256 and 328, or a substantially similar sequence thereof having at least 90%, at least 95%, at least 98% or at least 99% sequence identity; (iv) comprises a HCDR1 domain having an amino acid sequence selected from the group consisting of SEQ ID NOs: 4, 20, 36, 52, 68, 84, 100, 116, 132, 148, 164, 180, 196, 212, 228, 244, 260, 268, 276, 284, 292, 300, 308, 316 and 332, or a substantially similar sequence thereof having at least 90%, at least 95%, at least 98% or at least 99% sequence identity; a HCDR2 domain having an amino acid sequence selected from the group consisting of SEQ ID NOs: 6, 22, 38, 54, 70, 86, 102, 118, 134, 150, 166, 182, 198, 214, 230, 246, 262, 270, 278, 286, 294, 302, 310, 318, and 334, or a substantially similar sequence thereof having at least 90%, at least 95%, at least 98% or at least 99% sequence identity; a LCDR1 domain having an amino acid sequence selected from the group consisting of SEQ ID NOs: 12, 28, 44, 60, 76, 92, 108, 124, 140, 156, 172, 188, 204, 220, 236, 252 and 324, or a substantially similar sequence thereof having at least 90%, at least 95%, at least 98% or at least 99% sequence identity; and a LCDR2 domain having an amino acid sequence selected from the group consisting of SEQ ID NOs: 14, 30, 46, 62, 78, 94, 110, 126, 142, 158, 174, 190, 206, 222, 238, 254, and 326, or a substantially similar sequence thereof having at least 90%, at least 95%, at least 98% or at least 99% sequence identity; (v) binds specifically to the N-terminal region of human ANGPTL8 defined by SEQ ID NO: 337; vi) does not bind specifically to the N-terminal region of human ANGPTL8 defined by SEQ ID NO: 337; vii) does not bind to the N-terminal coiled-coil region of human ANGPTL3 peptide of SEQ ID NO: 338, or to the N-terminal coiled-coil region of human ANGPTL4 peptide of SEQ ID NO: 339; viii) binds human ANGPTL8 at 25° C. with a $K_D$ of less than about 150 pM and binds monkey ANGPTL8 at 25° C. with a $K_D$ of less than about 90 pM as measured by surface plasmon resonance; ix) lowers triglyceride levels in a mammal by about 68% (maximum) when administered subcutaneously at a dose of about 10 mg/kg; x) lowers triglyceride levels in a mammal for a period ranging from about 7 days to 21 days, when administered subcutaneously at doses ranging from about 5 mg/kg to about 25 mg/kg; xi) cross-competes with a reference antibody, wherein the reference antibody comprises a heavy chain variable region (HCVR) and a light chain variable region (LCVR) amino acid sequence selected from the group consisting of any of the HCVR and LCVR amino acid sequences of Table 1.

In a second aspect, the present invention also provides nucleic acid molecules encoding anti-ANGPTL8 antibodies or portions thereof. For example, the present invention provides nucleic acid molecules encoding any of the HCVR amino acid sequences listed in Table 1; in certain embodiments the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto.

The present invention also provides nucleic acid molecules encoding any of the LCVR amino acid sequences listed in Table 1. In certain embodiments the nucleic acid molecule comprises a polynucleotide sequence selected from any of the LCVR nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR1 amino acid sequences listed in Table 1. In certain embodiments the nucleic acid molecule comprises a polynucleotide sequence selected from any of the HCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR2 amino acid sequences listed in Table 1. In certain embodiments the nucleic acid molecule comprises a polynucleotide sequence selected from any of the HCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR3 amino acid sequences listed in Table 1. In certain embodiments the nucleic acid molecule comprises a polynucleotide sequence selected from any of the HCDR3 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR1 amino acid sequences listed in Table 1. In certain embodiments the nucleic acid molecule comprises a polynucleotide sequence selected from any of the LCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR2 amino acid sequences listed in Table 1. In certain embodiments the nucleic acid molecule comprises a polynucleotide sequence selected from any of the LCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR3 amino acid sequences listed in Table 1. In certain embodiments the nucleic acid molecule comprises a polynucleotide sequence selected from any of the LCDR3 nucleic acid sequences listed in Table 2, or a substantially similar sequence thereof having at least 90%, at least 95%, at least 98% or at least 99% sequence identity thereto.

The present invention also provides nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by any of the exemplary anti-ANGPTL8 antibodies listed in Table 1.

The present invention also provides nucleic acid molecules encoding an LCVR, wherein the LCVR comprises a set of three CDRs (i.e., LCDR1-LCDR2-LCDR3), wherein the LCDR1-LCDR2-LCDR3 amino acid sequence set is as defined by any of the exemplary anti-ANGPTL8 antibodies listed in Table 1.

The present invention also provides nucleic acid molecules encoding both an HCVR and an LCVR, wherein the HCVR comprises an amino acid sequence of any of the HCVR amino acid sequences listed in Table 1, and wherein the LCVR comprises an amino acid sequence of any of the LCVR amino acid sequences listed in Table 1. In certain embodiments, the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto, and a polynucleotide sequence selected from any of the LCVR nucleic acid sequences listed in Table 2, or a substantially similar sequence thereof having at least 90%, at least 95%, at least 98% or at least 99% sequence identity thereto. In certain embodiments according to this aspect of the invention, the nucleic acid molecule encodes an HCVR and LCVR, wherein the HCVR and LCVR are both derived from the same anti-ANGPTL8 antibody listed in Table 1.

The present invention also provides recombinant expression vectors capable of expressing a polypeptide comprising a heavy or light chain variable region of an anti-ANGPTL8 antibody. For example, the present invention includes recombinant expression vectors comprising any of the nucleic acid molecules mentioned above, i.e., nucleic acid molecules encoding any of the HCVR, LCVR, and/or CDR sequences as set forth in Table 1. Also included within the scope of the present invention are host cells into which such vectors have been introduced, as well as methods of producing the antibodies or portions thereof by culturing the host cells under conditions permitting production of the antibodies or antibody fragments, and recovering the antibodies and antibody fragments so produced.

In one embodiment, the isolated antibody that binds specifically to and/or inhibits at least one activity associated with ANGPTL8, is a recombinantly produced human monoclonal antibody having a HCVR and/or a LCVR encoded by a nucleic acid sequence selected from the nucleic acid sequences found in Table 2.

In one embodiment, the invention provides an isolated nucleic acid molecule encoding an antibody or fragment thereof that binds specifically to human ANGPTL8, wherein the antibody or an antigen binding fragment thereof comprises (a) the complementarity determining regions (CDRs) of a heavy chain variable region (HCVR) having an amino acid sequence as set forth in Table 1; and (b) the CDRs of a light chain variable region (LCVR) having an amino acid sequence as set forth in Table 1.

In one embodiment, the invention provides an isolated nucleic acid molecule encoding an antibody or antigen-binding fragment thereof that binds specifically to human ANGPTL8, wherein the antibody or antigen-binding fragment comprises an HCVR selected from the group consisting of an amino acid sequence as set forth in Table 1 and a LCVR selected from the group consisting of an amino acid sequence as set forth in Table 1.

In a third aspect, the invention provides a pharmaceutical composition comprising a recombinant human monoclonal antibody or antigen-binding fragment thereof, which specifically binds ANGPTL8 and a pharmaceutically acceptable carrier.

In one embodiment, the invention provides a pharmaceutical composition comprising at least one antibody specific for human ANGPTL8 selected from an antibody or an antigen-binding fragment thereof of any of the anti-ANGPTL8 antibodies found in Table 1 and a pharmaceutically acceptable carrier or diluent.

In a related aspect, the invention features a composition, which is a combination of an anti-ANGPTL8 antibody and a second therapeutic agent. In one embodiment, the second therapeutic agent is any agent that is advantageously combined with an anti-ANGPTL8 antibody.

In one embodiment, the second therapeutic agent may be an agent capable of lowering triglycerides or reducing at least one symptom in a patient suffering from a disease or condition characterized by high triglyceride levels, such as hypertriglyceridemia.

In certain embodiments, the second therapeutic agent may be an agent that helps to counteract or reduce any possible side effect(s) associated with the antibody or antigen-binding fragment of an antibody of the invention, if such side effect(s) should occur.

The second therapeutic agent may be a small molecule drug, a protein/polypeptide, an antibody, a nucleic acid molecule, such as an anti-sense molecule, or a siRNA. The second therapeutic agent may be synthetic or naturally derived.

It will also be appreciated that the antibodies and pharmaceutically acceptable compositions of the present invention can be employed in other combination therapies, that is, the antibodies and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an antibody may be administered concurrently with another agent used to treat the same disorder), or they may achieve different effects (e.g., control of any adverse effects). As used herein, additional therapeutic agents that are normally administered to treat or prevent a particular disease, or condition, are appropriate for the disease, or condition, being treated.

In a related embodiment, the invention features a composition, which is a combination of an antibody or antigen-binding fragment thereof of the invention, and a second therapeutic agent, such as (1) 3-hydroxy-3-methylglutaryl-coenzyme A (HMG-CoA) reductase inhibitors, such as cerivastatin, atorvastatin, simvastatin, pitavastatin, rosuvastatin, fluvastatin, lovastatin, pravastatin, and the like; (2) inhibitors of cholesterol uptake and/or bile acid re-absorption; (3) niacin, which increases lipoprotein catabolism; (4) fibrates or amphipathic carboxylic acids, which reduce TG level, low-density lipoprotein (LDL) level and improve high-density lipoprotein (HDL) levels; and (5) activators of the LXR transcription factor that plays a role in cholesterol elimination such as 22-hydroxycholesterol, or fixed combinations such as ezetimibe plus simvastatin; a statin with a bile resin (e.g., cholestyramine, colestipol, colesevelam), a fixed combination of niacin plus a statin (e.g., niacin with lovastatin); or with other lipid lowering agents such as omega-3-fatty acid ethyl esters (for example, omacor).

Furthermore, the second therapeutic agent can be one or more other inhibitors of ANGPTL8 as well as inhibitors of other molecules, such as ANGPTL3, ANGPTL4, ANGPTL5, ANGPTL6, apolipoprotein C-III (APOC3) and proprotein convertase subtilisin/kexin type 9 (PCSK9), which are involved in lipid metabolism, in particular, cholesterol and/or triglyceride homeostasis. Inhibitors of these molecules include small molecules, antisense molecules and antibodies that specifically bind to these molecules and block their activity.

In one embodiment, if the anti-ANGPTL8 antibodies of the invention are used to treat a disease such as diabetes (e.g., type 2 diabetes), then these antibodies may be used in combination with one or more of the following treatments for diabetes that are currently available. These include the following: insulin, an insulin analog (see below), a biguanide (metformin), a sulfonylurea (e.g. glyburide, glipizide), a PPAR gamma agonist (e.g. pioglitazone, rosiglitazone), an alpha glucosidase inhibitor (e.g. acarbose, voglibose), a glucagon-like peptide 1 (GLP-1) agonist (e.g., BYETTA® (exenatide), TRULICITY™ (dulaglutide), VICTOZA® (liraglutide), Lyxumia® (lixisenatide), Tanzeum™ (albiglutide)), a dipeptidyl peptidase IV (DPP-4) inhibitor (e.g. saxagliptin (ONGLYZA®), sitaliptin (JANUVIA®), and vildagliptin (GALVUS®), a sodium-glucose co-transporter 2 (SGLT2) inhibitor (e.g., INVOKANA™ (canagliflozin), FORXIGA® (dapagliflozin), empagliflozin, ipragliflozin, tofogliflozin), SYMLIN® (pramlintide), a glucagon receptor antagonist (as described in, for example, U.S. Pat. No. 8,545,847), and a glucagon antagonist.

In certain related embodiments, the composition may include a second agent selected from the group consisting of non-sulfonylurea secretagogues, insulin analogs, including fast acting (e.g., Lispro, Aspart, Glulisine) and long acting (e.g. Detemir insulin, Degludec insulin, or Glargine insulin, exendin-4 polypeptides, beta 3 adrenoceptor agonists, inhibitors of cholesterol uptake and/or bile acid re-absorption, LDL-cholesterol antagonists, cholesteryl ester transfer protein antagonists (e.g. torcetrapib, anacetrapib, dalcetrapib, or evacetrapib), endothelin receptor antagonists, growth hormone antagonists, insulin sensitizers, amylin mimetics or agonists, cannabinoid receptor antagonists, glucagon-like peptide-1 receptor agonists, melanocortins, melanin-concentrating hormone receptor agonists, SNRIs, a fibroblast growth factor 21 (FGF21) mimetic (See, for example, US20110002845 and US20080261236), a fibroblast growth factor receptor 1c (FGFR1c) agonist (See, for example, US20110150901), an inhibitor of advanced glycation end product formation, such as, but not limited to, aminoguanidine, and protein tyrosine phosphatase inhibitors.

In related embodiments, the second therapeutic agent may be one or more other therapeutic agents, such as analgesics, anti-inflammatory agents, including non-steroidal anti-inflammatory drugs (NSAIDS), such as Cox-2 inhibitors, and the like, so as to ameliorate and/or reduce the symptoms accompanying the underlying condition, if needed.

In a fourth aspect, the invention provides a method for neutralizing, inhibiting, blocking, abrogating, reducing or interfering with, at least one activity associated with ANGPTL8 in a patient in need thereof, the method comprising administering any one or more of the antibodies of the invention, as found in Table 1, or a pharmaceutical composition comprising any one or more of these antibodies to a patient in need thereof, wherein at least one activity associated with ANGPTL8 is reduced or diminished.

In one embodiment, the invention provides a therapeutic method comprising administering to a subject in need thereof a therapeutically effective amount of a pharmaceutical composition comprising one or more anti-hANGPTL8 antibodies or antigen-binding fragments thereof of the invention and, optionally one or more additional therapeutic agents as described above.

In a fifth aspect, the invention provides a method for treating a disease or condition associated in part with elevated expression and/or activity of ANGPTL8, the method comprising administering an ANGPTL8 inhibitor/antagonist, wherein the ANGPTL8 inhibitor/antagonist is an antibody or an antigen-binding fragment thereof specific for ANGPTL8. In one embodiment, the antibody or an antigen-binding fragment thereof specific for ANGPTL8 comprises an HCVR selected from the group consisting of an amino acid sequence from Table 1 and a LCVR selected from the group consisting of an amino acid sequence from Table 1.

In one embodiment, the disease or disorder treatable by the methods of the invention is any disease or condition which is improved, ameliorated, inhibited or prevented, or at least one symptom associated with the disease is reduced in severity or frequency of occurrence, compared to that without anti-hANGPTL8 antibody treatment (e.g., ANGPTL8-mediated diseases or disorders), by removing, inhibiting, reducing, or otherwise interfering with, ANGPTL8 activity. Examples of diseases or disorders treatable by the methods of the invention include, but are not limited to, those involving lipid metabolism, such as hyperlipidemia, hyperlipoproteinemia and dyslipidemia, including atherogenic dyslipidemia, diabetic dyslipidemia, hypertriglyceridemia, including severe hypertriglyceridemia with TG>1000 mg/dL and associated acute pancreatitis, hypercholesterolemia, chylomicronemia, mixed dyslipidemia (obesity, metabolic syndrome, diabetes, etc.), lipodystrophy, lipoatrophy, and the like, which are caused by, for example, decreased LPL activity and/or LPL deficiency, altered ApoC2, ApoE deficiency, increased ApoB, increased production and/or decreased elimination of very low-density lipoprotein (VLDL), certain drug treatment (e.g., glucocorticoid treatment-induced dyslipidemia), any genetic predisposition, diet, life style, and the like.

The methods of the invention can also prevent or treat diseases or disorders associated with or resulting from triglyceridemia, hypertriglyceridemia, hyperlipidemia, hyper-lipoproteinemia, and/or dyslipidemia, including, but not limited to, cardiovascular diseases or disorders, such as atherosclerosis, aneurysm, hypertension, angina, stroke, cerebrovascular diseases, congestive heart failure, coronary artery diseases, myocardial infarction, peripheral vascular diseases, and the like; acute pancreatitis; nonalcoholic steatohepatitis (NASH); blood sugar disorders, such as diabetes; obesity, and the like.

In one embodiment, at least one antibody of the invention, or an antigen-binding fragment thereof, may be used to treat metabolic syndrome associated dyslipidemia, obesity, or for preventing weight gain, or for maintaining a normal weight.

In one embodiment, the invention provides a method for lowering blood triglyceride levels, or for treating a condition or disease associated with, or characterized in part by high blood triglyceride levels, or at least one symptom or complication associated with the condition or disease, the method comprising administering a pharmaceutical composition comprising one or more antibodies specific for human ANGPTL8 from Table 1, to a patient in need thereof, such that blood triglyceride levels are lowered or that the condition or disease is mediated, or at least one symptom or complication associated with the condition or disease is alleviated or reduced in severity.

In one embodiment, at least one antibody of the invention, or an antigen-binding fragment thereof, may be used alone or in combination with a second or third therapeutic agent to treat hypertriglyceridemia, or at least one symptom associated with hypertriglyceridemia, or may be used to treat a patient at risk for acquiring hypertriglyceridemia, for example, in a patient who has a genetic predisposition for developing hypertriglyceridemia, e.g. familial hypertriglyceridemia or familial dysbetalipoproteinemia.

Other conditions may predispose a patient to high levels of triglycerides. For example, certain medications such as beta blockers, birth control pills, diuretics, steroids, or the use of tamoxifen may lead to elevated levels of triglycerides and as such, may increase a patient's likelihood of developing conditions, or complications associated with high levels of triglycerides, such as atherosclerosis, stroke, heart attack, and other cardiac conditions.

In addition, certain other conditions may lead to high levels of triglycerides, including obesity, poorly controlled diabetes, hypothyroidism, kidney disease, or alcohol consumption.

In one embodiment, the antibodies may be used to prevent the onset of a disease or disorder characterized in part by elevated blood triglyceride levels, or to prevent the likelihood of developing such disease or disorder, or to mitigate the severity of the disease or disorder, or at least one symptom associated with the disease or disorder. It is envisioned that the antibodies of the invention may be used alone, or as adjunct therapy with other agents or methods known to be standard care for treating patients suffering from diseases or conditions characterized in part by elevated blood triglyceride levels, such as, but not limited to, hypertriglyceridemia. Such standard therapy may include fluid administration, or administration of any other pharmaceutical agents useful for lowering blood triglycerides, or lipids, or for weight reduction.

In one embodiment, the use of the antibodies described herein, may be an effective means of achieving normal levels of triglycerides, thereby ameliorating, or preventing one or more symptoms of, or long-term complications associated with a disease characterized by high triglyceride levels.

In one embodiment, the antibodies of the invention may be used in the preparation of a medicament for use in treating any disease or disorder characterized in part by elevated levels of triglycerides.

The antibodies of the invention may be used as short-term therapy in an acute setting, or they may be envisioned for long-term use as chronic therapy.

In one aspect, the invention provides a method for achieving a reduction of body weight in a subject, the method comprising administering an ANGPTL8 inhibitor, wherein the ANGPTL8 inhibitor/antagonist is an antibody or antigen-binding fragment thereof specific for ANGPTL8, or a pharmaceutical composition comprising the antibody or antigen-binding fragment thereof, to the subject, wherein at least one activity of ANGPTL8 is reduced or diminished.

The terms inhibitor and antagonist are used interchangeably herein.

In another aspect, the invention provides a method for achieving a reduction of fat mass in a subject, the method comprising administering an ANGPTL8 inhibitor/antagonist, wherein the ANGPTL8 inhibitor/antagonist is an antibody or antigen-binding fragment thereof specific for ANGPTL8, or a pharmaceutical composition comprising the antibody or antigen-binding fragment thereof, to the subject, wherein at least one activity of ANGPTL8 is reduced or diminished.

In still another aspect, the invention provides a method for increasing energy expenditure in a subject, the method comprising administering an ANGPTL8 inhibitor/antagonist, wherein the ANGPTL8 inhibitor/antagonist is an antibody or antigen-binding fragment thereof specific for ANGPTL8, or a pharmaceutical composition comprising the antibody or antigen-binding fragment thereof, to the subject, wherein at least one activity of ANGPTL8 is reduced or diminished.

In yet another aspect, the invention provides a method for increasing HDL-C in a subject, the method comprising administering an ANGPTL8 inhibitor/antagonist, wherein the ANGPTL8 inhibitor/antagonist is an antibody or antigen-binding fragment thereof specific for ANGPTL8, or a pharmaceutical composition comprising the antibody or antigen-binding fragment thereof, to the subject, wherein at least one activity of ANGPTL8 is reduced or diminished. In one embodiment, circulating triglycerides (TGs) in said subject are reduced by at least 50% one day after said administering of an ANGPTL8 inhibitor/antagonist.

In additional embodiments of methods according to the invention, the antibody or antigen-binding fragment thereof specific for ANGPTL8 comprises a heavy chain variable region/light chain variable region (HCVR/LCVR) sequence pair as set forth in SEQ ID NOs:162/170 or 314/322.

In additional embodiments of methods according to the invention, the antibody or antigen-binding fragment thereof specific for ANGPTL8 comprises HCDR1/HCDR2/HCDR3/LCDR1/LCDR2/LCDR3 domains having amino acid sequences of SEQ ID NO: 164/166/168/172/174/176 or 316/318/320/324/326/328, respectively.

In one aspect, the invention provides a method for treating a condition or disease associated with obesity, or at least one symptom or complication associated with the condition or disease, by administering an ANGPTL8 inhibitor/antagonist, wherein the ANGPTL8 inhibitor/antagonist is an antibody or antigen-binding fragment thereof specific for ANGPTL8, or a pharmaceutical composition comprising the antibody or antigen-binding fragment thereof, to a patient in need thereof, such that the condition or disease is mediated, or the at least one symptom or complication associated with the condition or disease is alleviated or reduced in frequency or severity.

In additional embodiments, the methods according to the invention further comprise the administration of a secondary therapeutic agent. In still further embodiments, the second therapeutic agent is selected from the group consisting of an isolated antibody, or an antigen-binding fragment thereof, that specifically binds to angiopoietin-like protein 3 (ANGPTL3), angiopoietin-like protein 4 (ANGPTL4), angiopoietin-like protein 5 (ANGPTL5), angiopoietin-like protein 6 (ANGPTL6) and human proprotein convertase subtilisin/kexin type 9 (PCSK9). The second therapeutic agent can, without limitation, be selected from the group consisting of insulin, an insulin analog, a biguanide (metformin), a sulfonylurea (e.g. glyburide, glipizide), a PPAR gamma agonist (e.g. pioglitazone, rosiglitazone), an alpha glucosidase inhibitor (e.g. acarbose, voglibose), a glucagon-like peptide 1 (GLP-1) agonist (e.g., BYETTA® (exenatide), TRULICITY™ (dulaglutide), VICTOZA® (liraglutide), LYXUMIA® (lixisenatide, TANZEUM™ (albiglutide), or an analogue of any of the foregoing, a dipeptidyl peptidase IV (DPP-4) inhibitor (e.g. saxagliptin (ONGLYZA®), sitaliptin (JANUVIA®), and vildagliptin (GALVUS®), a sodium-glucose co-transporter 2 (SGLT2) inhibitor (e.g., INVOKANA™ (canagliflozin), FORXIGA® (dapagliflozin), empagliflozin, ipragliflozin, tofogliflozin), SYMLIN® (pramlintide), a glucagon receptor antagonist, a non-sulfonylurea secretagogue, an insulin analog (e.g., fast acting Lispro, Aspart, Glulisine and long acting Detemir insulin, Degludec insulin, or Glargine insulin), exendin-4 polypeptides, beta 3 adrenoceptor agonists, inhibitors of cholesterol uptake and/or bile acid re-absorption, LDL-cholesterol antagonists, cholesteryl ester transfer protein antagonists (e.g. torcetrapib, anacetrapib, dalcetrapib, or evacetrapib), endothelin receptor antagonists, growth hormone antagonists, insulin sensitizers, amylin mimetics or agonists, cannabinoid receptor antagonists, melanocortins, melanin-concentrating hormone receptor agonists, SNRIs, a fibroblast growth factor 21 (FGF21) mimetic, a fibroblast growth factor receptor 1c (FGFR1c) agonist, an inhibitor of advanced glycation endproduct formation (e.g. aminoguanidine), and protein tyrosine phosphatase inhibitors.

In one aspect, the invention provides a use of an ANGPTL8 inhibitor/antagonist, wherein the ANGPTL8 inhibitor/antagonist is an antibody or antigen-binding fragment thereof specific for ANGPTL8, or a pharmaceutical composition comprising the antibody or antigen-binding fragment thereof, in achieving a reduction of body weight in a subject, achieving a reduction of fat mass in a subject, increasing energy expenditure in a subject, increasing HDL-C in a subject, or treating a condition or disease associated with obesity.

In another aspect, the invention provides a use of an ANGPTL8 inhibitor/antagonist, wherein the ANGPTL8 inhibitor/antagonist is an antibody or antigen-binding fragment thereof specific for ANGPTL8, or a pharmaceutical composition comprising the antibody or antigen-binding fragment thereof, in the preparation of a medicament for achieving a reduction of body weight in a subject, achieving a reduction of fat mass in a subject, increasing energy expenditure in a subject, increasing HDL-C in a subject, or treating a condition or disease associated with obesity.

In still another aspect, the invention provides a pharmaceutical composition for achieving a reduction of body weight in a subject, achieving a reduction of fat mass in a subject, increasing energy expenditure in a subject, increasing HDL-C in a subject, or treating a condition or disease associated with obesity, wherein the composition comprises an ANGPTL8 inhibitor/antagonist, wherein the ANGPTL8 inhibitor/antagonist is an antibody or antigen-binding fragment thereof specific for ANGPTL8.

Other embodiments will become apparent from a review of the ensuing detailed description.

BRIEF DESCRIPTION OF THE FIGURES

FIGS. 3A and 3B show the effect of the H4H15341P mAb on serum lipoprotein lipase (LPL) (3A) and hepatic lipase (3B) in ANGPTL8 mice compared to control antibody. Statistics were done by unpaired student's t-test; $p<0.01$ FIG. 4 shows the effect of the mAb H4H15341P in a lipid tolerance test in ANGPTL8 mice. Administration of the H4H15341P mAb was assessed for lowering of triglyceride levels after acute fat loading compared to control antibody. Statistics were done by 2-way ANOVA with Bonferroni post-test; **p<0.0001

FIGS. 7A, 7B, 7C, 7D, 7E, 7F, and 7G. Multiple dose administration of H4H15341P reduces serum triglycerides, body weight and fat content, and increases energy expenditure in ANGPTL8$^{hum/hum}$ mice. Serum samples were collected from male ANGPTL8$^{hum/hum}$ mice (n=8/group, 7 weeks old) in non-fasted state. Thereafter, the mice were placed on a high-fat, high-cholesterol diet (HFHC). Seven days later, the mice received weekly subcutaneous injections of H4H15341P or control antibody (10 mg/kg). Serum samples were collected non-fasted six days after each injection. Changes in TG measured over the course of the study (7A). Body weights were monitored weekly (7B). Body composition was measured at 15 weeks (7C). Respiratory exchange ratio (RER) (7D), energy expenditure (7E), food intake (7F) and locomotor activity (7G) were measured during dark and light cycles in H4H15341P and control antibody treated mice. All values are mean±SEM. Statistical analysis was conducted by repeated measures 2-way ANOVA with Bonferroni correction post-test (7A and 7B) or Welch's t-test (7C-7G). *P<0.05; P<0.01; *P<0.001; ****P<0.0001.

DETAILED DESCRIPTION

Figure 1A:
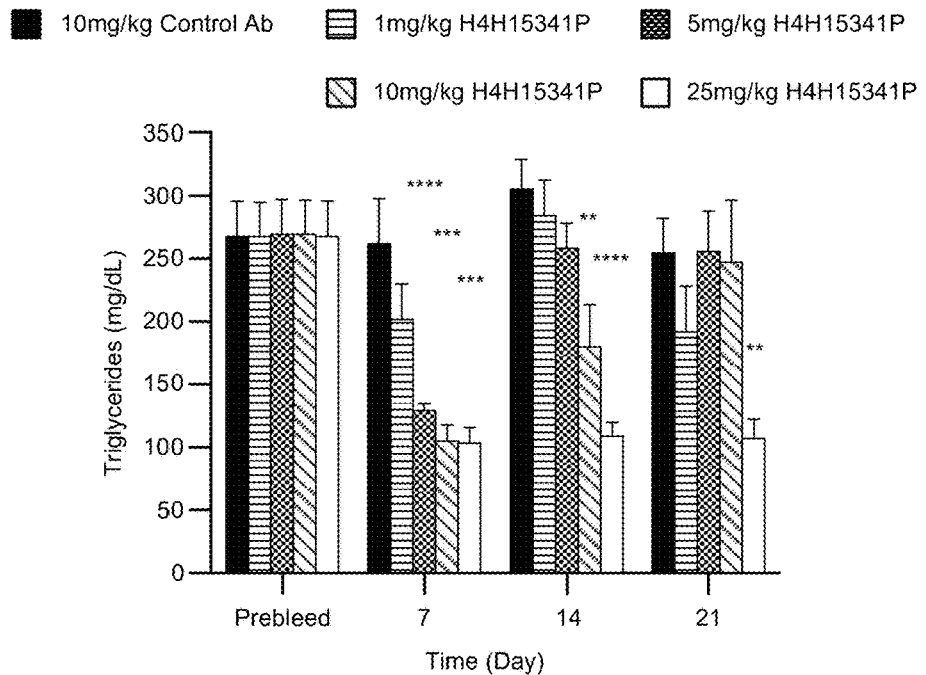
FIGS. 1A and 1B show the mean+/−SEM of serum triglyceride (1A) and total cholesterol (1B) concentration in humanized ANGPTL8 mice administered a single subcutaneous dose of H4H15341P. Doses administered were 1, 5, 10, or 25 mg/kg on day 0 of the study. Statistical comparison was done by 2-way ANOVA of differences from Control Ab, *$p<0.05$, $p<0.01$, *$p<0.001$, ****$p<0.0001$
Figure 1B:
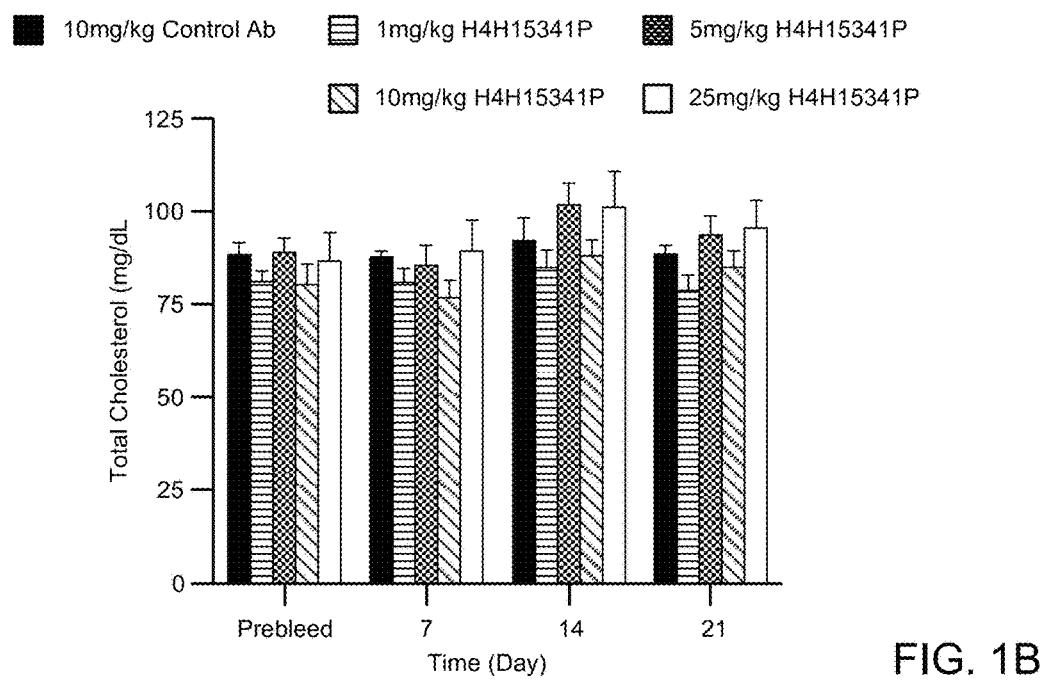

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Definitions

"Angiopoietin-like protein 8" or, "ANGPTL8," is a member of the angiopoietin family of proteins, and is sometimes referred to as TD26, RIFL, Lipasin, C19orf80 and Betatrophin. "ANGPTL8", as used herein, refers to human ANGPTL8 comprising the amino acid sequence as set forth in amino acid residues 1-177 of SEQ ID NO: 340. The full-length human ANGPTL8 amino acid sequence, including the signal sequence, can also be found in GenBank accession number NP_061157.3, while the full-length nucleic acid sequence encoding human ANGPTL8 is known (Ejarque, et al. 2017 *Transl Res* 184:35-44). The N-terminal coiled-coil domain of human ANGPTL8 spans amino acid residues 1-39 of SEQ ID NO: 340 and is also depicted as SEQ ID NO: 337. All references to proteins, polypeptides and protein fragments herein are intended to refer to the human version of the respective protein, polypeptide or protein fragment unless explicitly specified as being from a non-human species. Thus, the expression "ANGPTL8" means human ANGPTL8 unless specified as being from a non-human species, e.g., "mouse ANGPTL8," "monkey ANGPTL8," etc.

The term "human angiopoietin-like protein 3" or "hANGPTL3", as used herein, refers to ANGPTL3 having the nucleic acid sequence shown in SEQ ID NO:343 and the amino acid sequence of SEQ ID NO:342, or a biologically active fragment thereof. The N-terminal coiled-coil domain of human ANGPTL3 is depicted as SEQ ID NO: 338.

The term "human angiopoietin-like protein 4" or "hANGPTL4", as used herein, refers to ANGPTL4 having the nucleic acid sequence shown in SEQ ID NO:345 and the amino acid sequence of SEQ ID NO:344, or a biologically active fragment thereof. The N-terminal coiled-coil domain of human ANGPTL4 is depicted as SEQ ID NO: 339.

The specific embodiments, antibody or antibody fragments of the invention may be conjugated to a therapeutic moiety ("immunoconjugate"), such as a second ANGPTL8 antagonist, or any other therapeutic moiety useful for treating a disease or condition caused in part by elevated triglyceride levels.

As used herein, the expression "anti-ANGPTL8 antibody" includes both monovalent antibodies with a single specificity, as well as bispecific antibodies comprising a first arm that binds ANGPTL8 and a second arm that binds a second (target) antigen, wherein the anti-ANGPTL8 arm comprises any of the HCVR/LCVR or CDR sequences as set forth in Table 1 herein.

The term "antibody", as used herein, means any antigen-binding molecule or molecular complex comprising at least one complementarity determining region (CDR) that specifically binds to or interacts with a particular antigen (e.g., ANGPTL8). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-ANGPTL8 antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The term "human antibody", as used herein, is intended to include non-naturally occurring human antibodies. The term includes antibodies that are recombinantly produced in a non-human mammal, or in cells of a non-human mammal. The term is not intended to include antibodies isolated from or generated in a human subject.

The antibodies of the invention may, in some embodiments, be recombinant human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. In certain embodiments, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

The antibodies of the invention may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The anti-ANGPTL8 antibodies disclosed herein may comprise one or more amino acid substitutions, insertions and/or deletions in the framework and/or CDR regions of the heavy and light chain variable domains. Such mutations can be readily ascertained by comparing the amino acid sequences disclosed herein to sequences available from, for example, public antibody sequence databases. Once obtained, antibodies and antigen-binding fragments that contain one or more mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes anti-ANGPTL8 antibodies comprising variants of any of the HCVR, LCVR, and/or CDR amino acid sequences disclosed herein having one or more conservative substitutions. For example, the present invention includes anti-ANGPTL8 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth in Table 1 herein.

A "blocking antibody" or a "neutralizing antibody", as used herein (or an "antibody that neutralizes ANGPTL8 activity"), is intended to refer to an antibody whose binding to and/or interaction with ANGPTL8 results in inhibition of at least one biological activity of ANGPTL8. For example, an antibody of the invention may inhibit the lipoprotein lipase inhibitory activity of ANGPTL8, or it may lower plasma triglycerides through a mechanism other than through inhibition of the LPL inhibitory activity of ANGPTL8. This inhibition of the biological activity of ANGPTL8 can be assessed by measuring one or more indicators of ANGPTL8 biological activity by one or more of several standard in vitro or in vivo assays known in the art. An alternate activity is the triglyceride lowering activity associated with an antibody of the invention.

The term "surface plasmon resonance", or "SPR", as used herein, refers to an optical phenomenon that allows for the analysis of real-time biomolecular interactions by detection of alterations in protein concentrations within a biosensor matrix, for example using a BIACORE™ system (Pharmacia Biosensor AB, Uppsala, Sweden and Piscataway, N.J.), or a MASS-1 system (Sierra Sensors, Hamburg, Germany and Greenville, R.I.).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol.

215: 403 410 and (1997) Nucleic Acids Res. 25:3389 402, each of which is herein incorporated by reference.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

The term "treating" or "treatment", as used herein, refers to an approach for obtaining beneficial or desired clinical results. In one embodiment of the invention, a beneficial or desired clinical result includes, but is not limited to, an improvement in blood triglyceride levels, or an improvement in any one or more conditions, diseases, or symptoms associated with, or resulting from, elevated levels of triglycerides, including, but not limited to hypertriglyceridemia, etc.

pH-Dependent Binding

The present invention includes anti-ANGPTL8 antibodies with pH-dependent binding characteristics. For example, an anti-ANGPTL8 antibody of the present invention may exhibit reduced binding to ANGPTL8 at acidic pH as compared to neutral pH. Alternatively, anti-ANGPTL8 antibodies of the invention may exhibit enhanced binding to ANGPTL8 at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding to ANGPTL8 at acidic pH as compared to neutral pH" is expressed in terms of a ratio of the $K_D$ value of the antibody binding to ANGPTL8 at acidic pH to the $K_D$ value of the antibody binding to ANGPTL8 at neutral pH (or vice versa). For example, an antibody or antigen-binding fragment thereof may be regarded as exhibiting "reduced binding to ANGPTL8 at acidic pH as compared to neutral pH" for purposes of the present invention if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment of the present invention can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0. 25.0, 30.0, 40.0, 50.0, 60.0, 70.0, 100.0 or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained.

Anti-ANGPTL8 Antibodies Comprising Fc Variants

According to certain embodiments of the present invention, anti-ANGPTL8 antibodies are provided comprising an Fc domain comprising one or more mutations, which enhance or diminish antibody binding to the FcRn receptor, e.g., at acidic pH as compared to neutral pH. For example, the present invention includes anti-ANGPTL8 antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., N297A) modification.

For example, the present invention includes anti-ANGPTL8 antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); 257I and 311I (e.g., P257I and O311I); 257I and 434H (e.g., P257I and N434H); 376V and 434H (e.g., D376V and N434H); 307A, 380A and 434A (e.g., T307A, E380A and N434A); and 433K and 434F (e.g., H433K and N434F). All possible combinations of the foregoing Fc domain mutations, and other mutations within the antibody variable domains disclosed herein, are contemplated within the scope of the present invention.

The present invention also includes anti-ANGPTL8 antibodies comprising a chimeric heavy chain constant ($C_H$) region, wherein the chimeric $C_H$ region comprises segments derived from the $C_H$ regions of more than one immunoglobulin isotype. For example, the antibodies of the invention may comprise a chimeric $C_H$ region comprising part or all of a $C_H2$ domain derived from a human IgG1, human IgG2 or human IgG4 molecule, combined with part or all of a $C_H3$ domain derived from a human IgG1, human IgG2 or human IgG4 molecule. According to certain embodiments, the antibodies of the invention comprise a chimeric $C_H$ region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. According to certain embodiments, the chimeric hinge region comprises amino acid residues derived from a human IgG1 or a human IgG4 upper hinge and amino acid residues derived from a human IgG2 lower hinge. An antibody comprising a chimeric $C_H$ region as described herein may, in certain embodiments, exhibit modified Fc effector functions without adversely affecting the therapeutic or pharmacokinetic properties of the antibody. (See, e.g., U.S. Provisional Appl. No. 61/759,578, filed Feb. 1, 2013, the disclosure of which is hereby incorporated by reference in its entirety).

Biological Characteristics of the Antibodies

The present invention includes antibodies and antigen-binding fragments thereof that bind ANGPTL8 with high affinity. For example, the present invention includes anti-ANGPTL8 antibodies that bind human or monkey ANGPTL8 with a $K_D$ of less than about 150 nM, as measured by surface plasmon resonance (SPR) at 25° C., or at 37° C., e.g., using recombinant ANGPTL8 protein with a mouse IgG2a Fc C-terminal fusion, in an assay format as defined in Examples 3 and 4 herein, or a substantially similar assay. According to certain embodiments, anti-ANGPTL8 antibodies are provided that bind human or monkey ANGPTL8 at 25° C. or 37° C. with a $K_D$ of less than about 90 nM, or less than about 50 nM, less than about 3 nM, less than about 2 nM, less than about 1 nM, less than about 900 pM, less than about 500 pM, less than about 300 pM, less than about 150 pM, or less than about 90 pM, as measured by surface plasmon resonance, e.g., using an assay format as defined in Examples 3 and 4 herein, or a substantially similar assay.

The present invention also includes antibodies and antigen-binding fragments thereof that bind the peptide of SEQ ID NO: 337 derived from the N-terminal region of human ANGPTL8 with a dissociative half-life (t½) of greater than about 100 minutes as measured by surface plasmon resonance at 25° C. or 37° C., e.g., using an assay format as defined in Example 3 herein, or a substantially similar assay. According to certain embodiments, anti-ANGPTL8 antibodies are provided that bind peptides derived from the N-terminal region of human ANGPTL8 at 25° C. with a t½ of greater than or equal to about 110 minutes, greater than about 120 minutes, greater than about 130 minutes, greater than about 200 minutes, greater than about 300 minutes, greater than about 400 minutes, greater than about 500 minutes, or longer, as measured by surface plasmon resonance, e.g., using an assay format as defined in Example 3 herein, or a substantially similar assay.

The present invention also includes antibodies and antigen-binding fragments thereof that lower triglycerides in a mammal by about 20%, or by about 30%, or by about 40%, or by about 50%, or by about 60%, or greater when administered subcutaneously at a dose of about 0.1 mg/kg, or about 1 mg/kg, or about 10 mg/kg, or about 25 mg/kg, or about 50 mg/kg, or about 100 mg/kg. The effect of an antibody of the invention on lowering plasma triglycerides may last from at least 7 days after administration to about 3 weeks, or 4 weeks after administration, or longer.

An antibody of the invention comprises a heavy chain variable region (HCVR) having an amino acid sequence selected from the group consisting of SEQ ID NO: 2, 18, 34, 50, 66, 82, 98, 114, 130, 146, 162, 178, 194, 210, 226, 242, 258, 266, 274, 282, 290, 298, 306, 314 and 330; and a light chain variable region (LCVR) having an amino acid sequence selected from the group consisting of SEQ ID NO: 10, 26, 42, 58, 74, 90, 106, 122, 138, 154, 170, 186, 202, 218, 234, 250, and 322; or may cross-compete with a reference antibody, wherein the reference antibody comprises a heavy chain variable region (HCVR) and a light chain variable region (LCVR) amino acid sequence selected from the group consisting of any of the HCVR and LCVR amino acid sequences of Table 1.

An antibody of the invention may comprise a HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/250, 266/250, 274/250, 282/250, 290/250, 306/250, 314/322, and 330/322.

An antibody of the invention may comprise:

(a) a HCDR1 domain having an amino acid sequence selected from the group consisting of SEQ ID NOs: 4, 20, 36, 52, 68, 84, 100, 116, 132, 148, 164, 180, 196, 212, 228, 244, 260, 268, 276, 284, 292, 300, 308, 316 and 332;

(b) a HCDR2 domain having an amino acid sequence selected from the group consisting of SEQ ID NOs: 6, 22, 38, 54, 70, 86, 102, 118, 134, 150, 166, 182, 198, 214, 230, 246, 262, 270, 278, 286, 294, 302, 310, 318, and 334;

(c) a HCDR3 domain having an amino acid sequence selected from the group consisting of SEQ ID NOs: 8, 24, 40, 56, 72, 88, 104, 120, 136, 152, 168, 184, 200, 216, 232, 248, 264, 272, 280, 288, 296, 304, 312, 320 and 336;

(d) a LCDR1 domain having an amino acid sequence selected from the group consisting of SEQ ID NOs: 12, 28, 44, 60, 76, 92, 108, 124, 140, 156, 172, 188, 204, 220, 236, 252 and 324;

(e) a LCDR2 domain having an amino acid sequence selected from the group consisting of SEQ ID NOs: 14, 30, 46, 62, 78, 94, 110, 126, 142, 158, 174, 190, 206, 222, 238, 254, and 326; and (f) a LCDR3 domain having an amino acid sequence selected from the group consisting of SEQ ID NOs: 16, 32, 48, 64, 80, 96, 112, 128, 144, 160, 176, 192, 208, 224, 240, 256 and 328.

The antibodies of the present invention may possess one or more of the aforementioned biological characteristics, or any combination thereof. The foregoing list of biological characteristics of the antibodies of the invention is not intended to be exhaustive. Other biological characteristics of the antibodies of the present invention will be evident to a person of ordinary skill in the art from a review of the present disclosure including the working Examples herein.

Epitope Mapping and Related Technologies

The epitope to which the antibodies of the present invention bind may consist of a single contiguous sequence of 3 or more (e.g., 3, 4, 5, 6, 7, 8, 9, 10, 11, 12, 13, 14, 15, 16, 17, 18, 19, 20 or more) amino acids of an ANGPTL8 protein. Alternatively, the epitope may consist of a plurality of non-contiguous amino acids (or amino acid sequences) of ANGPTL8.

Various techniques known to persons of ordinary skill in the art can be used to determine whether an antibody "interacts with one or more amino acids" within a polypeptide or protein. Exemplary techniques include, e.g., routine cross-blocking assay such as that described *Antibodies*, Harlow and Lane (Cold Spring Harbor Press, Cold Spring Harb., N.Y.), alanine scanning mutational analysis, peptide blots analysis (Reineke, 2004, Methods Mol Biol 248:443-463), and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) *Anal. Chem.* 73:256A-265A.

The present invention further includes anti-ANGPTL8 antibodies that bind to the same epitope as any of the specific exemplary antibodies described herein (e.g. antibodies comprising any of the amino acid sequences as set forth in Table 1 herein). Likewise, the present invention also includes anti-ANGPTL8 antibodies that compete for binding to ANGPTL8 with any of the specific exemplary antibodies described herein (e.g. antibodies comprising any of the amino acid sequences as set forth in Table 1 herein).

One can easily determine whether an antibody binds to the same epitope as, or competes for binding with, a reference anti-ANGPTL8 antibody by using routine methods known in the art and exemplified herein. For example, to determine if a test antibody binds to the same epitope as a reference anti-ANGPTL8 antibody of the invention, the reference antibody is allowed to bind to an ANGPTL8 protein. Next, the ability of a test antibody to bind to the ANGPTL8 molecule is assessed. If the test antibody is able to bind to ANGPTL8 following saturation binding with the reference anti-ANGPTL8 antibody, it can be concluded that the test antibody binds to a different epitope than the reference anti-ANGPTL8 antibody. On the other hand, if the test antibody is not able to bind to the ANGPTL8 molecule following saturation binding with the reference anti-ANGPTL8 antibody, then the test antibody may bind to the same epitope as the epitope bound by the reference anti-ANGPTL8 antibody of the invention. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990:50:1495-1502). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding (or cross-competes for binding) with a reference anti-ANGPTL8 antibody, the above-described binding methodology is performed in two orientations: In a first orientation, the reference antibody is allowed to bind to a ANGPTL8 protein under saturating conditions followed by assessment of binding of the test antibody to the ANGPTL8 molecule. In a second orientation, the test antibody is allowed to bind to an ANGPTL8 molecule under saturating conditions followed by assessment of binding of the reference antibody to the ANGPTL8 molecule. If, in both orientations, only the first (saturating) antibody is capable of binding to the ANGPTL8 molecule, then it is concluded that the test antibody and the reference antibody compete for binding to ANGPTL8. As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

Preparation of Human Antibodies

The anti-ANGPTL8 antibodies of the present invention can be fully human (non-naturally occurring) antibodies. Methods for generating monoclonal antibodies, including fully human monoclonal antibodies are known in the art. Any such known methods can be used in the context of the present invention to make human antibodies that specifically bind to human ANGPTL8.

Using VELOCIMMUNE® technology (see, for example, U.S. Pat. No. 6,596,541, Regeneron Pharmaceuticals, VELOCIMMUNE®) or any other known method for generating monoclonal antibodies, high affinity chimeric antibodies to an allergen are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

As described in the experimental section below, the high affinity chimeric antibodies, which are isolated having a human variable region and a mouse constant region, are characterized and selected for desirable characteristics, including affinity, selectivity, epitope, etc. The mouse constant regions are then replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

In general, the antibodies of the instant invention possess very high affinities, typically possessing $K_D$ of from about $10^{-12}$ through about $10^{-9}$ M, when measured by binding to antigen either immobilized on solid phase or in solution phase.

Bioequivalents

The anti-ANGPTL8 antibodies and antibody fragments of the present invention encompass proteins having amino acid sequences that vary from those of the described antibodies but that retain the ability to bind human ANGPTL8. Such variant antibodies and antibody fragments comprise one or more additions, deletions, or substitutions of amino acids when compared to parent sequence, but exhibit biological activity that is essentially equivalent to that of the described antibodies. Likewise, the anti-ANGPTL8 antibody-encoding DNA sequences of the present invention encompass sequences that comprise one or more additions, deletions, or substitutions of nucleotides when compared to the disclosed sequence, but that encode an anti-ANGPTL8 antibody or antibody fragment that is essentially bioequivalent to an anti-ANGPTL8 antibody or antibody fragment of the invention. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-ANGPTL8 antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include anti-ANGPTL8 antibody variants comprising amino acid changes, which modify the glycosylation characteristics of the antibodies, e.g., mutations which eliminate or remove glycosylation.

Multispecific Antibodies

The antibodies of the present invention may be monospecific or multispecific (e.g., bispecific). Multispecific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The anti-ANGPTL8 antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity.

The present invention includes bispecific antibodies wherein one arm of an immunoglobulin binds human ANGPTL8, and the other arm of the immunoglobulin is specific for a second antigen. The ANGPTL8-binding arm can comprise any of the HCVR/LCVR or CDR amino acid sequences as set forth in Table 1 herein.

An exemplary bispecific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bispecific antibody format described above are contemplated within the scope of the present invention.

Other exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

Therapeutic Formulation and Administration

The invention provides pharmaceutical compositions comprising the anti-ANGPTL8 antibodies or antigen-binding fragments thereof of the present invention. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™, Life Technologies, Carlsbad, Calif.), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient may vary depending upon the age and the size of the patient, target disease, conditions, route of administration, and the like. The preferred dose is typically calculated according to body weight or body surface area. In an adult patient, it may be advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering anti-ANGPTL8 antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu, et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition of the present invention include, but are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Immunoconjugates

The invention encompasses a human anti-ANGPTL8 monoclonal antibody conjugated to a therapeutic moiety ("immunoconjugate"), such as an agent that is capable of reducing blood triglyceride or lipid levels. The type of therapeutic moiety that may be conjugated to the anti-ANGPTL8 antibody will take into account the condition to be treated and the desired therapeutic effect to be achieved. For example, for treating hypertriglyceridemia, or any other condition whereby it is desirable to lower blood triglycerides, and/or to maintain normal blood triglyceride levels, an agent may be conjugated to the ANGPTL8 antibody. Alternatively, if the desired therapeutic effect is to treat the sequelae or symptoms associated with hypertriglyceridemia, or any other condition resulting from high, or uncontrolled blood triglyceride levels, it may be advantageous to conjugate an agent appropriate to treat the sequelae or symptoms of the condition. Examples of suitable agents for forming immunoconjugates are known in the art, see for example, WO 05/103081.

Therapeutic Uses of the Antibodies

The present antibodies are useful for lowering blood triglyceride levels, for example, in a patient suffering from hypertriglyceridemia, and also for the treatment of a wide range of conditions and disorders in which inhibiting the activity of ANGPTL8 is beneficial. Thus, the antibodies may find use for example to prevent, treat, or alleviate, diseases or conditions or associated symptoms or sequelae, of the endocrine system, the central nervous system, the peripheral nervous system, the cardiovascular system, the pulmonary system, and the gastrointestinal system, while reducing and or eliminating one or more of the unwanted side effects associated with the current treatments.

For example, the antibodies of the invention may be used to treat a disease or disorder including, but not limited to, those involving lipid metabolism, such as hyperlipidemia, hyperlipoproteinemia and dyslipidemia, including atherogenic dyslipidemia, diabetic dyslipidemia, hypertriglyceridemia, including severe hypertriglyceridemia with TG>1000 mg/dL and associated acute pancreatitis, hypercholesterolemia, chylomicronemia, mixed dyslipidemia (obesity, metabolic syndrome, diabetes, etc.), lipodystrophy, lipoatrophy, and the like, which are caused by, for example, decreased LPL activity and/or LPL deficiency, altered ApoC2, ApoE deficiency, increased ApoB, increased production and/or decreased elimination of very low-density lipoprotein (VLDL), certain drug treatment (e.g., glucocorticoid treatment-induced dyslipidemia), any genetic predisposition, diet, life style, and the like.

The methods of the invention can also prevent or treat diseases or disorders associated with or resulting from triglyceridemia, hypertriglyceridemia, hyperlipidemia, hyper-lipoproteinemia, and/or dyslipidemia, including, but not limited to, cardiovascular diseases or disorders, such as atherosclerosis, aneurysm, hypertension, angina, stroke, cerebrovascular diseases, congestive heart failure, coronary artery diseases, myocardial infarction, peripheral vascular diseases, and the like; acute pancreatitis; nonalcoholic steatohepatitis (NASH); blood sugar disorders, such as diabetes (e.g., Type II diabetes); obesity, and the like.

The methods of the invention can also prevent or treat diseases or disorders associated with obesity. In certain embodiments, methods of the invention can be used to achieve a reduction in body weight, achieve a reduction of fat mass, increase energy expenditure, induce expression of brown fat specific genes, and/or increase HDL-C in a subject by administering an ANGPTL8 inhibitor/antagonist.

In one embodiment, at least one antibody of the invention, or an antigen-binding fragment thereof, may be used to treat metabolic syndrome associated dyslipidemia, obesity, or for preventing weight gain, or for maintaining a normal weight.

In one embodiment, the invention provides a method for lowering blood triglyceride levels, or for treating a condition or disease associated with, or characterized in part by high blood triglyceride levels, or at least one symptom or complication associated with the condition or disease, the method comprising administering a pharmaceutical composition comprising one or more antibodies specific for human ANGPTL8 from Table 1, to a patient in need thereof, such that blood triglyceride levels are lowered or that the condition or disease is mediated, or at least one symptom or complication associated with the condition or disease is alleviated or reduced in severity.

In one embodiment, at least one antibody of the invention, or an antigen-binding fragment thereof, may be used alone or in combination with a second or third therapeutic agent to treat hypertriglyceridemia, or at least one symptom associated with hypertriglyceridemia, or may be used to treat a patient at risk for acquiring hypertriglyceridemia, for example, in a patient who has a genetic predisposition for developing hypertriglyceridemia, e.g. familial hypertriglyceridemia or familial dysbetalipoproteinemia.

Other conditions may predispose a patient to high levels of triglycerides. For example, certain medications such as beta blockers, birth control pills, diuretics, steroids, or the use of tamoxifen may lead to elevated levels of triglycerides and as such, may increase a patient's likelihood of developing conditions, or complications associated with high levels of triglycerides, such as atherosclerosis, stroke, heart attack, and other cardiac conditions.

In addition, certain other conditions may lead to high levels of triglycerides, including obesity, poorly controlled diabetes, hypothyroidism, kidney disease, or alcohol consumption.

In one embodiment, the antibodies may be used to prevent the onset of a disease or disorder characterized in part by elevated blood triglyceride levels, or to prevent the likelihood of developing such disease or disorder, or to mitigate the severity of the disease or disorder, or at least one symptom associated with the disease or disorder. It is envisioned that the antibodies of the invention may be used alone, or as adjunct therapy with other agents or methods known to be standard care for treating patients suffering from diseases or conditions characterized in part by elevated blood triglyceride levels, such as, but not limited to, hypertriglyceridemia. Such standard therapy may include fluid administration, or administration of any other pharmaceutical agents useful for lowering blood triglycerides, or lipids, or for weight reduction.

In one embodiment, the use of the antibodies described herein, may be an effective means of achieving normal levels of triglycerides, thereby ameliorating, or preventing one or more symptoms of, or long-term complications associated with a disease characterized by high triglyceride levels.

It is envisioned that the antibodies of the invention may be used in an acute setting (for short term use), or for longer term (chronic) use.

Combination Therapies

Combination therapies may include an anti-ANGPTL8 antibody of the invention and any additional therapeutic agent that may be advantageously combined with an antibody of the invention, or with a biologically active fragment of an antibody of the invention.

For example, when the antibodies of the invention are contemplated for use in treating a disease or condition characterized in part by elevated triglyceride levels, such as hypertriglyceridemia, a second therapeutic agent may be employed to aid in further lowering of triglyceride levels, or to reduce at least one symptom in a patient suffering from a disease or condition characterized by high blood triglyceride levels. Such a second agent may be selected from, for example, another ANGPTL8 antagonist (e.g. another different anti-ANGPTL8 antibody or small molecule inhibitor of ANGPTL8), or may include other therapeutic moieties useful for treating triglyceridemia, or other diseases or conditions associated with, or resulting from elevated blood triglyceride levels, or agents useful for treating any long-term complications associated with elevated and/or uncontrolled blood triglyceride levels.

In related embodiments, the invention features a composition, which is a combination of an antibody or antigen-binding fragment thereof of the invention, and a second therapeutic agent, such as (1) 3-hydroxy-3-methylglutaryl-coenzyme A (HMG-CoA) reductase inhibitors, such as cerivastatin, atorvastatin, simvastatin, pitavastatin, rosuvastatin, fluvastatin, lovastatin, pravastatin, and the like; (2) inhibitors of cholesterol uptake and/or bile acid re-absorption; (3) niacin, which increases lipoprotein catabolism; (4) fibrates or amphipathic carboxylic acids, which reduce low-density lipoprotein (LDL) level, improve high-density lipoprotein (HDL) and TG levels, and reduce the number of non-fatal heart attacks; and (5) activators of the LXR transcription factor that plays a role in cholesterol elimination such as 22-hydroxycholesterol, or fixed combinations such as ezetimibe plus simvastatin; a statin with a bile resin (e.g., cholestyramine, colestipol, colesevelam), a fixed combination of niacin plus a statin (e.g., niacin with lovastatin); or with other lipid lowering agents such as omega-3-fatty acid ethyl esters (for example, omacor).

Furthermore, the second therapeutic agent can be one or more other inhibitors/antagonists of glucagon or an inhibitor/antagonist of the glucagon receptor, as well as inhibitors of other molecules, such as other inhibitors of ANGPTL8, as well as inhibitors of other molecules, such as ANGPTL3, ANGPTL4, ANGPTL5, ANGPTL6, apolipoprotein C-III (also referred to as APOC3; see for example, inhibitors of APOC3 described in U.S. Pat. Nos. 8,530,439, 7,750,141, 7,598,227 and volanesorsen, also referred to as ISIS-APOCIIIRx) and proprotein convertase subtilisin/kexin type 9 (PCSK9), which are involved in lipid metabolism, in particular, cholesterol and/or triglyceride homeostasis. Inhibitors of these molecules include small molecules, anti-sense molecules and antibodies that specifically bind to these molecules and block their activity.

In one embodiment, if the anti-ANGPTL3 antibodies of the invention are used to treat a disease such as diabetes (e.g., type 2 diabetes), then these antibodies may be used in combination with one or more of the following treatments for diabetes that are currently available. These include the following: insulin, an insulin analog (see below), a biguanide (metformin), a sulfonylurea (e.g. glyburide, glipizide), a PPAR gamma agonist (e.g. pioglitazone, rosiglitazone), an alpha glucosidase inhibitor (e.g. acarbose, voglibose), a glucagon-like peptide 1 (GLP-1) receptor agonist (e.g., BYETTA® (exenatide), TRULICITY™ (dulaglutide), VICTOZA® (liraglutide), LYXUMIA® (lixisenatide), TANZEUM™ (albiglutide), or an analogue of any of the foregoing), a dipeptidyl peptidase IV (DPP-4) inhibitor (e.g. saxagliptin (ONGLYZA®), sitaliptin (JANUVIA®), and vildagliptin (GALVUS®), a sodium-glucose co-transporter 2 (SGLT2) inhibitor (e.g., INVOKANA™ (canagliflozin), FORXIGA® (dapagliflozin), empagliflozin, ipragliflozin, tofogliflozin), (SYMLIN® (pramlintide), a glucagon receptor antagonist (as described in, for example, U.S. Pat. No. 8,545,847), and a glucagon antagonist.

In certain related embodiments, the composition may include a second agent selected from the group consisting of non-sulfonylurea secretagogues, insulin analogs, including fast acting (e.g., Lispro, Aspart, Glulisine) and long acting (e.g. Detemir insulin, Degludec insulin, or Glargine insulin, exendin-4 polypeptides, beta 3 adrenoceptor agonists, inhibitors of cholesterol uptake and/or bile acid re-absorption, LDL-cholesterol antagonists, cholesteryl ester transfer protein antagonists (e.g. torcetrapib, anacetrapib, dalcetrapib, or evacetrapib), endothelin receptor antagonists, growth hormone antagonists, insulin sensitizers, amylin mimetics or agonists, cannabinoid receptor antagonists, glucagon-like peptide-1 receptor agonists, melanocortins, melanin-concentrating hormone receptor agonists, SNRIs, a fibroblast growth factor 21 (FGF21) mimetic (See, for example, US20110002845 and US20080261236), a fibroblast growth factor receptor 1c (FGFR1c) agonist (See, for example, US20110150901), an inhibitor of advanced glycation end product formation, such as, but not limited to, aminoguanidine, and protein tyrosine phosphatase inhibitors.

In related embodiments, the second therapeutic agent may be one or more other therapeutic agents, such as analgesics, anti-inflammatory agents, including non-steroidal anti-inflammatory drugs (NSAIDS), such as Cox-2 inhibitors, and the like, so as to ameliorate and/or reduce the symptoms accompanying the underlying condition, if needed.

The additional therapeutically active component(s) may be administered prior to, concurrent with, or after the administration of the anti-ANGPTL8 antibody of the present invention. For purposes of the present disclosure, such administration regimens are considered the administration of an anti-ANGPTL8 antibody "in combination with" a second therapeutically active component.

Administration Regimens

According to certain embodiments of the present invention, multiple doses of an anti-ANGPTL8 antibody (or a pharmaceutical composition comprising a combination of an anti-ANGPTL8 antibody and any of the additional therapeutically active agents mentioned herein) may be administered to a subject over a defined time course. The methods according to this aspect of the invention comprise sequentially administering to a subject multiple doses of an anti-ANGPTL8 antibody of the invention. As used herein, "sequentially administering" means that each dose of anti-ANGPTL8 antibody is administered to the subject at a different point in time, e.g., on different days separated by a predetermined interval (e.g., hours, days, weeks or months). The present invention includes methods which comprise sequentially administering to the patient a single initial dose of an anti-ANGPTL8 antibody, followed by one or more secondary doses of the anti-ANGPTL8 antibody, and optionally followed by one or more tertiary doses of the anti-ANGPTL8 antibody.

The terms "initial dose," "secondary doses," and "tertiary doses," refer to the temporal sequence of administration of the anti-ANGPTL8 antibody of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of anti-ANGPTL8 antibody, but generally may differ from one another in terms of frequency of administration. In certain embodiments, however, the amount of anti-ANGPTL8 antibody contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of anti-ANGPTL8 antibody, which is administered to a patient prior to the administration of the very next dose in the sequence with no intervening doses.

The methods according to this aspect of the invention may comprise administering to a patient any number of secondary and/or tertiary doses of an anti-ANGPTL8 antibody. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient. The administration regimen may be carried out indefinitely over the lifetime of a particular subject, or until such treatment is no longer therapeutically needed or advantageous.

In embodiments involving multiple secondary doses, each secondary dose may be administered at the same frequency as the other secondary doses. For example, each secondary dose may be administered to the patient 1 to 2 weeks or 1 to 2 months after the immediately preceding dose. Similarly, in embodiments involving multiple tertiary doses, each tertiary dose may be administered at the same frequency as the other tertiary doses. For example, each tertiary dose may be administered to the patient 2 to 12 weeks after the immediately preceding dose. In certain embodiments of the invention, the frequency at which the secondary and/or tertiary doses are administered to a patient can vary over the course of the treatment regimen. The frequency of administration may also be adjusted during the course of treatment by a physician depending on the needs of the individual patient following clinical examination.

Diagnostic Uses of the Antibodies

The anti-ANGPTL8 antibodies of the present invention may also be used to detect and/or measure ANGPTL8 in a sample, e.g., for diagnostic purposes. For example, an anti-ANGPTL8 antibody, or fragment thereof, may be used to diagnose a condition or disease characterized by aberrant expression (e.g., over-expression, under-expression, lack of expression, etc.) of ANGPTL8. Exemplary diagnostic assays for ANGPTL8 may comprise, e.g., contacting a sample, obtained from a patient, with an anti-ANGPTL8 antibody of the invention, wherein the anti-ANGPTL8 antibody is labeled with a detectable label or reporter molecule or used as a capture ligand to selectively isolate ANGPTL8 protein from patient samples. Alternatively, an unlabeled anti-ANGPTL8 antibody can be used in diagnostic applications in combination with a secondary antibody which is itself detectably labeled. The detectable label or reporter molecule can be a radioisotope, such as $^{3}H$, $^{14}C$, $^{32}C$, $^{35}S$, or $^{125}I$; a fluorescent or chemiluminescent moiety such as fluorescein isothiocyanate, or rhodamine; or an enzyme such as alkaline phosphatase, β-galactosidase, horseradish peroxidase, or luciferase.

Specific exemplary assays that can be used to detect or measure ANGPTL8 in a sample include enzyme-linked immunosorbent assay (ELISA), radioimmunoassay (RIA), and fluorescence-activated cell sorting (FACS).

Samples that can be used in ANGPTL8 diagnostic assays according to the present invention include any tissue or fluid sample obtainable from a patient, which contains detectable quantities of ANGPTL8 protein, or fragments thereof, under normal or pathological conditions. Generally, levels of ANGPTL8 in a particular sample obtained from a healthy patient (e.g., a patient not afflicted with a disease or condition associated with abnormal ANGPTL8 levels or activity) will be measured to initially establish a baseline, or standard, level of ANGPTL8. This baseline level of ANGPTL8 can then be compared against the levels of ANGPTL8 measured in samples obtained from individuals suspected of having a ANGPTL8 related disease or condition, or symptoms associated with such disease or condition.

EXAMPLES

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, preferred methods and materials are now described. All publications mentioned herein are incorporated herein by reference in their entirety.

Example 1. Generation of Anti-ANGPTL8 Antibodies

Anti-ANGPTL8 antibodies were obtained by immunizing a VELOCIMMUNE® mouse (i.e., an engineered mouse comprising DNA encoding human immunoglobulin heavy and kappa light chain variable regions) with an immunogen comprising a recombinant human ANGPTL8 expressed with a C-terminal mouse IgG2a tag (see SEQ ID NO: 340). The antibody immune response was monitored by an ANGPTL8-specific immunoassay. When a desired immune response was achieved, several fully human anti-ANGPTL8 antibodies were generated from antigen-positive B cells as described in US 2007/0280945A1, incorporated by reference herein in its entirety.

Certain biological properties of the exemplary anti-ANGPTL8 antibodies generated in accordance with the methods of this Example are described in detail in the Examples set forth below.

Example 2. Heavy and Light Chain Variable Region Amino Acid and Nucleic Acid Sequences Table 1 sets forth the amino acid sequence identifiers of the heavy and light chain variable regions and CDRs of selected anti-ANGPTL8 antibodies of the invention. The corresponding nucleic acid sequence identifiers are set forth in Table 2.

TABLE 1

Amino Acid Sequence Identifiers
SEQ ID NOs:

| Antibody Designation | HCVR | HCDR1 | HCDR2 | HCDR3 | LCVR | LCDR1 | LCDR2 | LCDR3 |
|---|---|---|---|---|---|---|---|---|
| H4H15314P2 | 2 | 4 | 6 | 8 | 10 | 12 | 14 | 16 |
| H4H15316P | 18 | 20 | 22 | 24 | 26 | 28 | 30 | 32 |
| H4H15318P | 34 | 36 | 38 | 40 | 42 | 44 | 46 | 48 |
| H4H15319P | 50 | 52 | 54 | 56 | 58 | 60 | 62 | 64 |
| H4H15321P | 66 | 68 | 70 | 72 | 74 | 76 | 78 | 80 |
| H4H15323P | 82 | 84 | 86 | 88 | 90 | 92 | 94 | 96 |
| H4H15330P | 98 | 100 | 102 | 104 | 106 | 108 | 110 | 112 |
| H4H15331P | 114 | 116 | 118 | 120 | 122 | 124 | 126 | 128 |
| H4H15334P | 130 | 132 | 134 | 136 | 138 | 140 | 142 | 144 |
| H4H15335P | 146 | 148 | 150 | 152 | 154 | 156 | 158 | 160 |
| H4H15341P | 162 | 164 | 166 | 168 | 170 | 172 | 174 | 176 |
| H4H15343P | 178 | 180 | 182 | 184 | 186 | 188 | 190 | 192 |
| H4H15345P | 194 | 196 | 198 | 200 | 202 | 204 | 206 | 208 |
| H4H15346P | 210 | 212 | 214 | 216 | 218 | 220 | 222 | 224 |
| H4H15347P | 226 | 228 | 230 | 232 | 234 | 236 | 238 | 240 |
| H4H15350P2 | 242 | 244 | 246 | 248 | 250 | 252 | 254 | 256 |
| H4H15353P2 | 258 | 260 | 262 | 264 | 250 | 252 | 254 | 256 |
| H4H15354P2 | 266 | 268 | 270 | 272 | 250 | 252 | 254 | 256 |
| H4H15355P2 | 274 | 276 | 278 | 280 | 250 | 252 | 254 | 256 |
| H4H15357P2 | 282 | 284 | 286 | 288 | 250 | 252 | 254 | 256 |
| H4H15361P2 | 290 | 292 | 294 | 296 | 250 | 252 | 254 | 256 |
| H4H15362P2 | 298 | 300 | 302 | 304 | 250 | 252 | 254 | 256 |
| H4H15363P2 | 306 | 308 | 310 | 312 | 250 | 252 | 254 | 256 |
| H4H15367P2 | 314 | 316 | 318 | 320 | 322 | 324 | 326 | 328 |
| H4H15369P2 | 330 | 332 | 334 | 336 | 322 | 324 | 326 | 328 |

TABLE 2

Nucleic Acid Sequence Identifiers
SEQ ID NOs:

| Antibody Designation | HCVR | HCDR1 | HCDR2 | HCDR3 | LCVR | LCDR1 | LCDR2 | LCDR3 |
|---|---|---|---|---|---|---|---|---|
| H4H15314P2 | 1 | 3 | 5 | 7 | 9 | 11 | 13 | 15 |
| H4H15316P | 17 | 19 | 21 | 23 | 25 | 27 | 29 | 31 |
| H4H15318P | 33 | 35 | 37 | 39 | 41 | 43 | 45 | 47 |
| H4H15319P | 49 | 51 | 53 | 55 | 57 | 59 | 61 | 63 |
| H4H15321P | 65 | 67 | 69 | 71 | 73 | 75 | 77 | 79 |
| H4H15323P | 81 | 83 | 85 | 87 | 89 | 91 | 93 | 95 |
| H4H15330P | 97 | 99 | 101 | 103 | 105 | 107 | 109 | 111 |
| H4H15331P | 113 | 115 | 117 | 119 | 121 | 123 | 125 | 127 |
| H4H15334P | 129 | 131 | 133 | 135 | 137 | 139 | 141 | 143 |
| H4H15335P | 145 | 147 | 149 | 151 | 153 | 155 | 157 | 159 |
| H4H15341P | 161 | 163 | 165 | 167 | 169 | 171 | 173 | 175 |
| H4H15343P | 177 | 179 | 181 | 183 | 185 | 187 | 189 | 191 |
| H4H15345P | 193 | 195 | 197 | 199 | 201 | 203 | 205 | 207 |
| H4H15346P | 209 | 211 | 213 | 215 | 217 | 219 | 221 | 223 |
| H4H15347P | 225 | 227 | 229 | 231 | 233 | 235 | 237 | 239 |
| H4H15350P2 | 241 | 243 | 245 | 247 | 249 | 251 | 253 | 255 |
| H4H15353P2 | 257 | 259 | 261 | 263 | 249 | 251 | 253 | 255 |
| H4H15354P2 | 265 | 267 | 269 | 271 | 249 | 251 | 253 | 255 |
| H4H15355P2 | 273 | 275 | 277 | 279 | 249 | 251 | 253 | 255 |

TABLE 2-continued

Nucleic Acid Sequence Identifiers
SEQ ID NOs:

| Antibody Designation | HCVR | HCDR1 | HCDR2 | HCDR3 | LCVR | LCDR1 | LCDR2 | LCDR3 |
|---|---|---|---|---|---|---|---|---|
| H4H15357P2 | 281 | 283 | 285 | 287 | 249 | 251 | 253 | 255 |
| H4H15361P2 | 289 | 291 | 293 | 295 | 249 | 251 | 253 | 255 |
| H4H15362P2 | 297 | 299 | 301 | 303 | 249 | 251 | 253 | 255 |
| H4H15363P2 | 305 | 307 | 309 | 311 | 249 | 251 | 253 | 255 |
| H4H15367P2 | 313 | 315 | 317 | 319 | 321 | 323 | 325 | 327 |
| H4H15369P2 | 329 | 331 | 333 | 335 | 321 | 323 | 325 | 327 |

Antibodies are typically referred to herein according to the following nomenclature: Fc prefix (e.g. "H1H," "H1M," "H2M", "H4H", etc.), followed by a numerical identifier (e.g. "15321," "15341," "15350," etc.), followed by a "P" or "N" suffix, as shown in Tables 1 and 2. Thus, according to this nomenclature, an antibody may be referred to herein as, e.g., "H4H15321P", etc. The H4H prefix on the antibody designations used herein indicate the particular Fc region isotype of the antibody. For example, an "H4H" antibody has a human IgG4 Fc, an "H1M" antibody has a mouse IgG1 Fc, and an "H2M" antibody has a mouse IgG2 Fc, (all variable regions are fully human as denoted by the first 'H' in the antibody designation). As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)—which are indicated by the numerical identifiers shown in Tables 1 and 2—will remain the same, and the binding properties are expected to be identical or substantially similar regardless of the nature of the Fc domain.

Example 3: Surface Plasmon Resonance (SPR) Determination of Dissociation Rate Constants ($k_d$) for ANGPTL8 Antibodies Binding to ANGPTL8, ANGPTL3, and ANGPTL4 Peptides It was previously demonstrated that antibodies binding to the N-terminal coiled-coil region of ANGPTL3 [WO 2012/174178 A1; Lee et al. (2009) JBC, 284:13735-13745] and ANGPTL4 [Desai et al. (2007) PNAS, 104:11766-11771] blocked the LPL inhibitory activity of the ANGPTL proteins. In this experiment, antibodies against ANGPTL8 were tested for binding to a peptide from the N-terminal region of ANGPTL8.

Dissociation rate constants for ANGPTL8 antibodies binding to human ANGPTL8 peptide (hANGPTL8 peptide, SEQ ID NO: 337) were determined using a real-time surface plasmon resonance based MASS-1 biosensor platform. The assay utilized a format where ANGPTL8 antibodies were captured on the sensor surface and peptides were injected over the antibody surface. Peptides from the N-terminal coiled-coil region of human ANGPTL3 (hANGPTL3 peptide, SEQ ID NO: 338) and human ANGPTL4 (hANGPTL4 peptide, SEQ ID NO: 339) were also included as controls. Also included was a control antibody (H4H268P from US2011/0159015A1) that binds to the ANGPTL4 peptide and a negative isotype control antibody. All binding studies were performed in 10 mM HEPES pH 7.4, 150 mM NaCl, 3 mM EDTA, and 0.05% v/v Surfactant Tween-20 (HBS-ET running buffer) at 25° C. The HCA sensor surface was derivatized via amine coupling to a monoclonal mouse anti-human Fc antibody (GE, # BR-1008-39), and to this surface was captured approximately 1000RU of each ANGPTL8 antibody or control antibody. Peptide stock solutions were diluted in HBS-ET running buffer to 500 nM and injected over the antibody-captured surfaces for 4 minutes at a flow rate of 304/minute followed by the dissociation of bound peptide in HBS-ET running buffer for 10 minutes.

The association phase of peptides binding to captured ANGPTL8 antibodies could not be fit to a 1:1 binding model; therefore, only the dissociation rate constant ($k_d$) values were calculated by fitting the real-time binding sensorgrams using Scrubber 2.0c curve-fitting software. Dissociative half-lives ($t\frac{1}{2}$) were calculated from $k_d$ as:

$$t1/2(\min) = \frac{\ln\{2\}}{60 * kd}$$

Binding parameters for the ANGPTL8, ANGPTL3, and ANGPTL4 N-terminal region peptides binding to captured ANGPTL8 antibodies, the control ANGPTL4 antibody, and the isotype control antibody are shown in Tables 3-5.

Results:

Under these experimental conditions, the maximum non-specific binding signal exhibited by 500 nM of hANGPTL8, hANGPTL3, or hANGPTL4 peptides to blank anti-hFc surface was 3 RUs. Hence, binding interactions with signals that were three-fold above the 3 RU non-specific background (i.e., ≥9RU) were considered specific binding interactions. Based on this criterion, antibody-peptide binding signals less than 9 RUs were considered non-binding (NB in Table 1).

From this binding study it was shown that ANGPTL8 antibodies H4H15321P, H4H15367P2, and H4H15345P bind specifically to the N-terminal region ANGPTL8 peptide (SEQ ID NO: 337). None of the ANGPTL8 antibodies bound to the hANGPTL3 (SEQ ID NO: 338) or hANGPTL4 (SEQ ID NO: 339) N-terminal region peptides.

TABLE 3

Binding of anti-ANGPTL8 monoclonal antibody to hANGPTL8 peptide at 25° C.

| mAb Captured | mAb Capture Level (RU)* | 500 nM hANGPTL8 peptide Bound (RU) | kd (1/s) | t½ (min) |
|---|---|---|---|---|
| H4H15321P | 1101 ± 6.1 | 61 | 8.29E−05 | 139 |
| H4H15367P2 | 1116 ± 17.4 | 43 | 9.82E−05 | 118 |
| H4H15345P | 1096 ± 3.6 | 37 | 2.03E−05 | 570 |
| H4H15361P2 | 1394 ± 12.3 | 4 | NB | NB |
| H4H15347P | 1554 ± 54.6 | 0 | NB | NB |

TABLE 3-continued

Binding of anti-ANGPTL8 monoclonal antibody to hANGPTL8 peptide at 25° C.

| mAb Captured | mAb Capture Level (RU)* | 500 nM hANGPTL8 peptide Bound (RU) | kd (1/s) | t½ (min) |
|---|---|---|---|---|
| H4H15318P | 1087 ± 31.5 | 0 | NB | NB |
| H4H15350P2 | 1298 ± 30.7 | 0 | NB | NB |
| H4H15363P2 | 1281 ± 13.7 | 0 | NB | NB |
| H4H15346P | 1277 ± 26.3 | 0 | NB | NB |
| H4H15334P | 1256 ± 5.3 | 0 | NB | NB |
| H4H15335P | 1625 ± 31 | 0 | NB | NB |
| H4H15343P | 1129 ± 19.8 | 0 | NB | NB |
| H4H15357P2 | 1159 ± 13.1 | 0 | NB | NB |
| H4H15353P2 | 1296 ± 8.5 | 0 | NB | NB |
| H4H15341P | 1023 ± 30.1 | 0 | NB | NB |
| H4H15369P2 | 1196 ± 54.2 | 0 | NB | NB |
| H4H15330P | 1168 ± 20.1 | 0 | NB | NB |
| H4H15362P2 | 1131 ± 15.5 | 0 | NB | NB |
| H4H15319P | 974 ± 3.5 | 0 | NB | NB |
| H4H15316P | 1107 ± 24.7 | 0 | NB | NB |
| H4H15323P | 1068 ± 16.4 | 0 | NB | NB |
| H4H15354P2 | 1297 ± 8.5 | 0 | NB | NB |
| H4H15355P2 | 1323 ± 25.4 | 0 | NB | NB |
| H4H15314P2 | 1011 ± 3.4 | 0 | NB | NB |
| H4H15331P | 1264 ± 16.8 | −1 | NB | NB |
| (α-AngPTL4 Ab) | 1281 ± 50.2 | 0 | NB | NB |
| Negative isotype control Ab | 1092 ± 41.5 | 0 | NB | NB |
| Blank α-hFc Surface | 5 ± 0.3 | 3 | NB | NB |

*This column displays the average and standard deviation of antibody surface densities used for binding to ANGPTL8.

TABLE 4

Binding of anti-ANGPTL8 monoclonal antibody to hANGPTL3 shift peptide at 25° C.

| mAb Captured | mAb Capture Level (RU)* | 500 nM hANGPTL3 peptide Bound (RU) | kd (1/s) | t½ (min) |
|---|---|---|---|---|
| H4H15321P | 1101 ± 6.1 | 0 | NB | NB |
| H4H15367P2 | 1116 ± 17.4 | 0 | NB | NB |
| H4H15345P | 1096 ± 3.6 | 0 | NB | NB |
| H4H15361P2 | 1394 ± 12.3 | 0 | NB | NB |
| H4H15347P | 1554 ± 54.6 | −1 | NB | NB |
| H4H15318P | 1087 ± 31.5 | 0 | NB | NB |
| H4H15350P2 | 1298 ± 30.7 | 0 | NB | NB |
| H4H15363P2 | 1281 ± 13.7 | 0 | NB | NB |
| H4H15346P | 1277 ± 26.3 | 0 | NB | NB |
| H4H15334P | 1256 ± 5.3 | 0 | NB | NB |
| H4H15335P | 1625 ± 31 | −1 | NB | NB |
| H4H15343P | 1129 ± 19.8 | 0 | NB | NB |
| H4H15357P2 | 1159 ± 13.1 | 0 | NB | NB |
| H4H15353P2 | 1296 ± 8.5 | 0 | NB | NB |
| H4H15341P | 1023 ± 30.1 | 0 | NB | NB |
| H4H15369P2 | 1196 ± 54.2 | 0 | NB | NB |
| H4H15330P | 1168 ± 20.1 | −1 | NB | NB |
| H4H15362P2 | 1131 ± 15.5 | 0 | NB | NB |
| H4H15319P | 974 ± 3.5 | 0 | NB | NB |
| H4H15316P | 1107 ± 24.7 | 0 | NB | NB |
| H4H15323P | 1068 ± 16.4 | 0 | NB | NB |
| H4H15354P2 | 1297 ± 8.5 | 0 | NB | NB |
| H4H15355P2 | 1323 ± 25.4 | 0 | NB | NB |
| H4H15314P2 | 1011 ± 3.4 | 0 | NB | NB |
| H4H15331P | 1264 ± 16.8 | 0 | NB | NB |
| (α-AngPTL4 Ab) | 1281 ± 50.2 | 0 | NB | NB |
| Negative isotype control Ab | 1092 ± 41.5 | 0 | NB | NB |
| Blank α-hFc Surface | 5 ± 0.3 | 0 | NB | NB |

*This column displays the average and standard deviation of antibody surface densities used for binding to ANGPTL3 peptide.

TABLE 5

Binding of anti-ANGPTL8 monoclonal antibody to hAngPTL4 peptide at 25° C.

| mAb Captured | mAb Capture Level (RU)* | 500 nM hAngPTL4 peptide Bound (RU) | kd (1/s) | t½ (min) |
|---|---|---|---|---|
| H4H15321P | 1101 ± 6.1 | 0 | NB | NB |
| H4H15367P2 | 1116 ± 17.4 | 0 | NB | NB |
| H4H15345P | 1096 ± 3.6 | 0 | NB | NB |
| H4H15361P2 | 1394 ± 12.3 | 0 | NB | NB |
| H4H15347P | 1554 ± 54.6 | 0 | NB | NB |
| H4H15318P | 1087 ± 31.5 | 0 | NB | NB |
| H4H15350P2 | 1298 ± 30.7 | 0 | NB | NB |
| H4H15363P2 | 1281 ± 13.7 | 0 | NB | NB |
| H4H15346P | 1277 ± 26.3 | 0 | NB | NB |
| H4H15334P | 1256 ± 5.3 | 1 | NB | NB |
| H4H15335P | 1625 ± 31 | 1 | NB | NB |
| H4H15343P | 1129 ± 19.8 | 0 | NB | NB |
| H4H15357P2 | 1159 ± 13.1 | 0 | NB | NB |
| H4H15353P2 | 1296 ± 8.5 | 0 | NB | NB |
| H4H15341P | 1023 ± 30.1 | 0 | NB | NB |
| H4H15369P2 | 1196 ± 54.2 | 0 | NB | NB |
| H4H15330P | 1168 ± 20.1 | 0 | NB | NB |
| H4H15362P2 | 1131 ± 15.5 | 0 | NB | NB |
| H4H15319P | 974 ± 3.5 | 0 | NB | NB |
| H4H15316P | 1107 ± 24.7 | 0 | NB | NB |
| H4H15323P | 1068 ± 16.4 | 0 | NB | NB |
| H4H15354P2 | 1297 ± 8.5 | 0 | NB | NB |
| H4H15355P2 | 1323 ± 25.4 | 0 | NB | NB |
| H4H15314P2 | 1011 ± 3.4 | 1 | NB | NB |
| H4H15331P | 1264 ± 16.8 | 0 | NB | NB |
| (α-AngPTL4 Ab) | 1281 ± 50.2 | 23 | 1.02E−03 | 11 |
| Negative isotype control Ab | 1092 ± 41.5 | 0 | NB | NB |
| Blank α-hFc Surface | 5 ± 0.3 | 0 | NB | NB |

*This column displays the average and standard deviation of antibody surface densities used for binding to ANGPTL4 peptide.

Example 4: Determination of Kinetic Binding Parameters for H4H15341P Binding to Full-Length Human and Monkey ANGPTL8 Proteins by Surface Plasmon Resonance (SPR)

The equilibrium dissociation constant ($K_D$) for ANGPTL8 antibody H4H15341P binding to full-length human and cynomolgus monkey ANGPTL8 proteins was determined using a real-time surface plasmon resonance-based MASS-1 biosensor platform. For the assay H4H15341P was injected over sensor surfaces onto which human or monkey ANGPTL8 proteins were immobilized. All binding studies were performed in 10 mM HEPES pH 7.4, 150 mM NaCl, 3 mM EDTA, and 0.05% v/v Surfactant Tween-20 (HBS-ET running buffer) at 25° C. The HCA sensor surface was first derivatized by amine coupling goat anti-mouse IgG2a polyclonal antibody (Southern Biotech, #1080-01) onto which was then captured approximately 30 RU (binding units) of human ANGPTL8 expressed with C-terminal mouse IgG2a Fc tag (hANGPTL8-mFc; SEQ ID NO: 340) or monkey ANGPTL8 expressed with C-terminal mouse IgG2a Fc tag (MfANGPTL8-mFc; SEQ ID NO: 341). Different concentrations of ANGPTL8 mAb were first prepared in HBS-ET running buffer (300 nM-1.23 nM; 3-fold serial dilution) and then injected over the ANGPTL8-mFc captured surfaces for 4 minutes at a flow rate of 304/minute followed by the dissociation of bound mAb in HBS-ET running buffer for 10 minutes.

Kinetic association ($k_a$) and dissociation ($k_d$) rate constants were determined by fitting the real-time binding sensorgrams to a 1:1 binding model with mass transport limitation using Scrubber 2.0c curve-fitting software. Binding dissociation equilibrium constants ($K_D$) and dissociative half-lives (t½) were calculated from the kinetic rate constants as:

$$K_D(M) = \frac{kd}{ka}, \text{ and } t1/2(\min) = \frac{\ln\{2\}}{60 * kd}$$

Binding kinetic parameters for anti-ANGPTL8 mAb binding to hANGPTL8-mFc and MfANGPTL8-mFc at 25° C. is shown in Table 6.

Results:

Antibody H4H15341 bound to both human and monkey ANGPTL8 proteins immobilized on the sensor surface and did not exhibit measurable dissociation during the recorded dissociation phase. To obtain an estimate of the binding affinity the dissociation rate constant, $k_d$, was fixed at the upper detection limit under the experimental conditions, 1.0E-05 1/s. The equilibrium dissociation constant ($K_D$) values of H4H15341P binding to hANGPTL8-mFc and MfANGPTL8-mFc were estimated to be 117 pM and 86 pM or lower, respectively.

TABLE 6

Binding kinetics parameters of H4H15341P binding to hANGPTL8-mFc and MfANGPTL8-mFc at 25° C.

| Capture Surface | $k_a$ (1/Ms) | $k_d$ (1/s) | $K_D$ (M) | t½ (min) |
|---|---|---|---|---|
| hANGPTL8-mFc | 8.50E+04 | 1.00E−05* | ≤1.17E−10 | ≥1155 |
| MfANGPTL8-mFc | 1.16E+05 | 1.00E−05* | ≤8.60E−11 | ≥1155 |

*No dissociation of anti-ANGPTL8 mAb was observed under the experimental conditions; therefore, the value of $k_d$ was fixed at the upper detection limit of 1.00E−05 s$^{-1}$.

Example 5: Determination of Human and Monkey ANGPTL8 Binding Specificity by Bio-Layer Interferometry (BLI)

Binding of ANGPTL8 antibodies to human and monkey ANGPTL8 proteins was investigated using Bio-layer Interferometry with an Octet HTX biosensor platform (ForteBio, A Division of Pall Life Sciences). All experiments were performed at 25° C. in 10 mM HEPES pH 7.4, 150 mM NaCl, 0.05% v/v Surfactant Tween-20, and 1 mg/ml BSA with the reaction multiwell plate agitated at 1000 rpm. Approximately 1.6 nm of human ANGPTL8 produced with a C-terminal mouse IgG2a Fc tag (hANGPTL8-mFc; SEQ ID NO: 340) or cynomolgus monkey ANGPTL8 produced with a C-terminal mouse IgG2a Fc tag (MfANGPTL8-mFc; SEQ ID NO: 341) was captured onto anti-mFc (AMC) Octet biosensors by submerging the sensors into wells containing 10 µg/mL of each protein for 4 minutes. Under the same conditions a negative control protein with the same mFc tag (hLDLR-mFc) was also coupled to the AMC sensor. All four sensors, three protein-coupled and one blank, were then submerged into wells containing 100 nM of different ANGPTL8 monoclonal antibodies or an isotype control for 4 minutes. Binding signals observed after the 4-minute binding step are tabulated in Table 7.

Results:

Among 25 ANGPTL8 mAbs tested in this study, 24 antibodies displayed binding signals higher than the maximum binding signals on the irrelevant control sensor tips (0.03 nm; this value was used to calculate binding signals as fold above background). Among the 24 human ANGPTL8 binders, 20 displayed positive binding on the monkey ANGPTL8 protein. The 4 antibodies that did not bind to monkey ANGPTL8 protein also displayed low binding signal on the human ANGPTL8 protein with values between 1-2-fold above the background binding signal. For the 24 antibodies binding to human ANGPTL8 protein, 4 antibodies (H4H15362P2, H4H15321P, H4H15330P, H4H15367P2) showed binding signals of 10-fold above background. Another group of 12 antibodies displayed binding signals between 5-10-fold above background. The remaining antibodies bound the human ANGPTL8 protein with binding signals that were between 1-5-fold above the background level.

TABLE 7

Binding specificity of 100 nM ANGPTL8 monoclonal antibodies to human and monkey ANGPTL8-mFc captured on Octet biosensors

| | mAb Binding Response (nm) | | | |
|---|---|---|---|---|
| mAb PID# | hANGPTL8.mFc Captured Surface | MfANGPTL8.mFc Captured Surface | Irrelevant control (hLDLR.mFc) Captured Surface | Blank AMC Sensor |
| H4H15362P2 | 0.39 | 0.36 | 0.03 | 0.01 |
| H4H15321P | 0.36 | 0.51 | 0.01 | 0.00 |
| H4H15330P | 0.34 | 0.39 | 0.02 | 0.01 |
| H4H15367P2 | 0.32 | 0.33 | 0.01 | 0.00 |

TABLE 7-continued

Binding specificity of 100 nM ANGPTL8 monoclonal antibodies to human and monkey ANGPTL8-mFc captured on Octet biosensors

| | mAb Binding Response (nm) | | | |
|---|---|---|---|---|
| mAb PID# | hANGPTL8.mFc Captured Surface | MfANGPTL8.mFc Captured Surface | Irrelevant control (hLDLR.mFc) Captured Surface | Blank AMC Sensor |
| H4H15363P2 | 0.25 | 0.26 | 0.01 | 0.02 |
| H4H15347P | 0.25 | 0.29 | 0.01 | 0.03 |
| H4H15345P | 0.25 | 0.31 | 0.00 | 0.01 |
| H4H15319P | 0.22 | 0.26 | −0.01 | 0.00 |
| H4H15361P2 | 0.20 | 0.21 | 0.01 | 0.02 |
| H4H15318P | 0.19 | 0.20 | 0.01 | 0.01 |
| H4H15323P | 0.18 | 0.15 | 0.00 | 0.00 |
| H4H15350P2 | 0.17 | 0.20 | 0.00 | −0.01 |
| H4H15343P | 0.17 | 0.20 | −0.01 | 0.01 |
| H4H15331P | 0.16 | 0.21 | 0.01 | 0.01 |
| H4H15355P2 | 0.15 | 0.13 | 0.02 | 0.03 |
| H4H15353P2 | 0.15 | 0.11 | 0.02 | 0.02 |
| H4H15369P2 | 0.14 | 0.17 | 0.00 | 0.01 |
| H4H15357P2 | 0.13 | 0.08 | 0.01 | 0.02 |
| H4H15341P | 0.12 | 0.10 | 0.02 | 0.03 |
| H4H15346P | 0.07 | 0.01 | 0.00 | −0.01 |
| H4H15335P | 0.06 | 0.04 | 0.01 | 0.01 |
| H4H15354P2 | 0.05 | 0.03 | 0.01 | 0.02 |
| H4H15334P | 0.05 | 0.01 | 0.00 | 0.03 |
| H4H15314P2 | 0.04 | 0.01 | 0.01 | 0.00 |
| H4H15316P | 0.03 | 0.02 | 0.02 | 0.02 |
| Negative Isotype control Ab | 0.01 | 0.00 | 0.01 | 0.01 |

Example 6: In Vivo Effect of IgG4 Anti-hANGPTL8 Antibodies on Circulating Triglyceride Levels in Humanized ANGPTL8 Mice The effect of anti-hANGPTL8 antibodies on serum triglyceride (TG) levels was determined in humanized ANGPTL8 mice. Mice were pre-bled 7 days before the experiment and put into groups of five mice each for each antibody tested. Antibodies were administered at 10 mg/kg dose (anti-hANGPTL8 and isotype-matched (hIgG4) control with irrelevant specificity) by subcutaneous injection on Day 0 of the study. Mice were bled (nonfasted) at consecutive days after antibody injections and TG levels were determined in the serum by ADVIA® 1800 Serum Chemistry Analyzer (Siemens). Averages were calculated for each of the time points for all tested antibodies. Results, expressed as (mean±SEM) of serum TG concentration, are shown in Tables 8-13.

Levels of circulating anti-hANGPTL8 (Serum Ab) were also determined using a standard ELISA assay. Briefly, plates were coated with a goat anti-human Fc antibody (Sigma-Aldrich) to capture Serum Ab. Serum was then added to the plates and captured antibodies were detected by chemiluminescence using a horseradish peroxidase (HRP) conjugated goat anti-human IgG antibody (Sigma-Aldrich). Results, expressed as (mean±SEM) of are shown in Tables 14-19. Control: Mice that received an isotype-matched Control Ab Results:

The effect of 25 mAbs to hANGPTL8 on circulating TG levels were tested in humanized ANGPTL8 mice. Antibody H4H15341P led to significant reduction in circulating TG (up to 68% average) after administration (compared to control mAb).

TABLE 8

Study 1, serum triglycerides (mg/dL)

| Days after injection | Antibody | | | | | | | | | |
|---|---|---|---|---|---|---|---|---|---|---|
| | Control | | H4H15321P | | H4H15331P | | H4H15343P | | H4H15367P2 | |
| | Mean | SEM | Mean | SEM | Mean | SEM | Mean | SEM | Mean | SEM |
| −7 | 205.4 | 14.20 | 203.8 | 19.68 | 206.6 | 16.20 | 205.2 | 12.13 | 203.6 | 14.21 |
| 1 | 233.6 | 16.93 | 239.4 | 28.61 | 259.8 | 35.52 | 196.8 | 16.05 | 222.0 | 27.41 |
| 4 | 210.4 | 12.79 | 233.2 | 26.19 | 244.4 | 33.83 | 175.2 | 10.32 | 234.8 | 27.28 |
| 7 | 261.0 | 19.66 | 235.6 | 33.82 | 241.8 | 55.74 | 201.8 | 23.50 | 203.2 | 27.79 |

TABLE 9

Study 2, serum triglycerides (mg/dL)

| Days after injection | Control | | H4H15341P | | H4H15319P | | H4H15318P | |
|---|---|---|---|---|---|---|---|---|
| | Mean | SEM | Mean | SEM | Mean | SEM | Mean | SEM |
| −7 | 214.8 | 20.08 | 211.4 | 21.67 | 213.6 | 20.50 | 212.8 | 20.00 |
| 1 | 255.4 | 25.18 | 82.0 | 3.35 | 217.4 | 26.92 | 235.2 | 24.62 |
| 4 | 228.6 | 33.43 | 93.6 | 7.69 | 195.0 | 29.93 | 270.6 | 34.28 |
| 7 | 197.0 | 21.22 | 90.8 | 7.68 | 235.4 | 35.70 | 209.6 | 31.88 |
| 14 | 223.0 | 14.98 | 126.4 | 21.75 | 185.2 | 29.94 | 166.0 | 24.58 |

| Days after injection | Antibody | | | |
|---|---|---|---|---|
| | H4H15355P2 | | H4H15345P | |
| | Mean | SEM | Mean | SEM |
| −7 | 214.4 | 19.18 | 213.0 | 20.34 |
| 1 | 248.2 | 45.93 | 228.8 | 37.97 |
| 4 | 221.2 | 30.30 | 195.80 | 23.87 |
| 7 | 254.2 | 37.93 | 252.60 | 25.24 |
| 14 | 219.4 | 36.69 | 190.60 | 13.13 |

TABLE 10

Study 3, serum triglycerides (mg/dL)

| Days after injection | Control | | H4H15350P2 | | H4H15314P2 | | H4H15330P | | H4H15361P2 | |
|---|---|---|---|---|---|---|---|---|---|---|
| | Mean | SEM | Mean | SEM | Mean | SEM | Mean | SEM | Mean | SEM |
| −7 | 247.8 | 23.88 | 242.8 | 21.60 | 244.0 | 26.34 | 243.2 | 22.29 | 242.4 | 25.29 |
| 1 | 214.6 | 20.37 | 206.6 | 21.60 | 228.2 | 35.33 | 206.6 | 25.44 | 215.4 | 20.20 |
| 4 | 222.4 | 13.78 | 198.2 | 22.61 | 192.4 | 17.25 | 216.6 | 15.84 | 200.0 | 15.89 |
| 7 | 288.8 | 35.41 | 274.6 | 45.48 | 238.6 | 21.21 | 244.4 | 14.61 | 247.4 | 37.93 |

TABLE 11

Study 4, serum triglycerides (mg/dL)

| Days after injection | Control | | H4H15357P2 | | H4H15363P2 | | H4H15347P | | H4H15369P | |
|---|---|---|---|---|---|---|---|---|---|---|
| | Mean | SEM | Mean | SEM | Mean | SEM | Mean | SEM | Mean | SEM |
| −7 | 197.0 | 18.29 | 201.6 | 25.18 | 201.6 | 26.15 | 200.4 | 24.71 | 198.8 | 22.43 |
| 1 | 227.6 | 46.41 | 221.6 | 37.35 | 189.4 | 5.963 | 194.6 | 28.33 | 217.0 | 39.68 |
| 6 | 194.0 | 18.06 | 211.2 | 35.96 | 190.6 | 20.21 | 248.2 | 16.12 | 223.0 | 25.61 |

TABLE 12

Study 5, serum triglycerides (mg/dL)

| Days after injection | Control | | H4H15353P2 | | H4H15323P | | H4H15362P2 | |
|---|---|---|---|---|---|---|---|---|
| | Mean | SEM | Mean | SEM | Mean | SEM | Mean | SEM |
| −7 | 199.2 | 26.68 | 197.4 | 27.02 | 199.8 | 30.33 | 200.8 | 27.55 |
| 2 | 217.2 | 16.09 | 184.4 | 28.67 | 179.8 | 35.99 | 166.6 | 26.76 |
| 8 | 161.8 | 18.58 | 185.4 | 24.78 | 187.0 | 38.76 | 180.2 | 18.22 |
| 14 | 227.2 | 33.70 | 216.4 | 11.74 | 212.4 | 31.29 | 173.2 | 17.75 |

TABLE 12-continued

Study 5, serum triglycerides (mg/dL)

| Days after injection | H4H15334P | | H4H15354P2 | |
|---|---|---|---|---|
| | Mean | SEM | Mean | SEM |
| −7 | 199.8 | 26.25 | 200.0 | 26.33 |
| 2 | 183.0 | 16.93 | 169.8 | 23.14 |
| 8 | 160.0 | 16.56 | 162.6 | 20.50 |
| 14 | 167.6 | 18.73 | 197.4 | 34.20 |

TABLE 13

Study 6, serum triglycerides (mg/dL)

| Days after injection | Control | | H4H15316P | | H4H15335P | | H4H15346P | |
|---|---|---|---|---|---|---|---|---|
| | Mean | SEM | Mean | SEM | Mean | SEM | Mean | SEM |
| −7 | 232.0 | 24.94 | 232.0 | 28.26 | 232.4 | 23.88 | 232.8 | 30.30 |
| 2 | 211.0 | 23.19 | 248.2 | 35.35 | 203.2 | 6.785 | 197.2 | 20.42 |
| 7 | 256.8 | 32.02 | 249.6 | 35.72 | 248.0 | 17.28 | 234.8 | 66.74 |

TABLE 14

Study 1, Serum Ab (µg/mL)

| Days after injection | Antibody | | | | | | | | | |
|---|---|---|---|---|---|---|---|---|---|---|
| | Control | | H4H15321P | | H4H15331P | | H4H15343P | | H4H15367P2 | |
| | Mean | SEM | Mean | SEM | Mean | SEM | Mean | SEM | Mean | SEM |
| 1 | 64.1 | 9.0 | 76.4 | 8.6 | 9.8 | 2.0 | 74.4 | 8.5 | 113.0 | 9.6 |
| 4 | 55.8 | 6.3 | 66.5 | 4.6 | 3.3 | 0.7 | 68.3 | 4.4 | 101.4 | 11.3 |

TABLE 15

Study 2, Serum Ab (µg/mL)

| Days after injection | Antibody | | | | | | | | |
|---|---|---|---|---|---|---|---|---|---|
| | Control | | H4H15341P | | H4H15319P | | H4H15318P | | |
| | Mean | SEM | Mean | SEM | Mean | SEM | Mean | SEM | |
| 1 | 50.8 | 3.9 | 104.0 | 18.7 | 81.8 | 8.2 | 74.4 | 8.5 | |
| 4 | 51.2 | 9.5 | 70.6 | 23.6 | 59.1 | 9.6 | 68.3 | 4.4 | |
| 7 | 40.9 | 5.4 | 50.7 | 13.3 | 46.8 | 8.9 | 68.3 | 4.4 | |
| 14 | 32.2 | 3.1 | 8.2 | 4.6 | 24.1 | 8.7 | 68.3 | 4.4 | |

| Days after injection | Antibody | | | |
|---|---|---|---|---|
| | H4H15355P2 | | H4H15345P | |
| | Mean | SEM | Mean | SEM |
| 1 | 68.4 | 3.8 | 59.3 | 3.6 |
| 4 | 58.4 | 3.0 | 46.3 | 16.2 |
| 7 | 35.7 | 6.6 | 50.1 | 3.9 |
| 14 | 3.1 | 0.8 | 35.9 | 4.6 |

TABLE 16

Study 3, Serum Ab (µg/mL)

| Days after injection | Antibody | | | | | | | | | |
|---|---|---|---|---|---|---|---|---|---|---|
| | Control | | H4H15350P2 | | H4H15314P2 | | H4H15330P | | H4H15361P2 | |
| | Mean | SEM | Mean | SEM | Mean | SEM | Mean | SEM | Mean | SEM |
| 1 | 47.3 | 7.0 | 57.2 | 23.4 | 89.9 | 13.0 | 38.3 | 14.7 | 50.0 | 13.6 |
| 4 | 50.6 | 13.4 | 66.1 | 22.6 | 69.9 | 12.9 | 35.4 | 0.9 | 57.4 | 10.1 |
| 7 | 38.8 | 9.2 | 39.9 | 14.7 | 48.6 | 17.3 | 30.0 | 5.1 | 38.7 | 11.1 |

TABLE 17

Study 4, Serum Ab (µg/mL)

| Days after injection | Antibody | | | | | | | | | |
|---|---|---|---|---|---|---|---|---|---|---|
| | Control | | H4H15357P2 | | H4H15363P2 | | H4H15347P | | H4H15369P | |
| | Mean | SEM | Mean | SEM | Mean | SEM | Mean | SEM | Mean | SEM |
| 1 | 100.9 | 100.9 | 78.4 | 26.7 | 93.2 | 10.1 | 53.6 | 7.5 | 99.7 | 15.6 |
| 6 | 84.0 | 84.0 | 56.9 | 14.8 | 62.0 | 7.6 | 9.5 | 2.9 | 68.0 | 12.0 |

TABLE 18

Study 5, Serum Ab (µg/mL)

| Days after injection | Antibody | | | | | | | | |
|---|---|---|---|---|---|---|---|---|---|
| | Control | | H4H15353P2 | | H4H15323P | | H4H15362P2 | | |
| | Mean | SEM | Mean | SEM | Mean | SEM | Mean | SEM | |
| 2 | 93.7 | 14.4 | 63.5 | 17.6 | 99.9 | 34.5 | 91.0 | 24.6 | |
| 8 | 79.8 | 8.7 | 42.8 | 11.1 | 50.3 | 9.7 | 50.8 | 10.3 | |
| 14 | 55.1 | 11.4 | 18.2 | 14.0 | 32.3 | 10.0 | 29.5 | 20.9 | |

| Days after injection | Antibody | | | |
|---|---|---|---|---|
| | H4H15334P | | H4H15354P2 | |
| | Mean | SEM | Mean | SEM |
| 2 | 64.4 | 15.0 | 71.3 | 7.2 |
| 8 | 38.7 | 7.1 | 46.0 | 15.4 |
| 14 | 8.6 | 4.6 | 30.1 | 26.6 |

TABLE 19

| | Study 6, Serum Ab (µg/mL) | | | | | | | |
|---|---|---|---|---|---|---|---|---|
| Days after injection | Antibody | | | | | | | |
| | Control | | H4H15316P | | H4H15335P | | H4H15346P | |
| | Mean | SEM | Mean | SEM | Mean | SEM | Mean | SEM |
| 2 | 87.4 | 9.2 | 79.3 | 18.5 | 66.9 | 17.5 | 61.1 | 22.8 |
| 7 | 97.4 | 23.0 | 77.9 | 12.8 | 78.6 | 16.2 | 56.7 | 23.7 |

Example 7: Dose Response of hANGPTL8 Antibody H4H15341P in Humanized ANGPTL8 Mice The effects of different doses of hANGPTL8 mAb, H4H15341P, on serum triglycerides (TG) were evaluated in humanized ANGPTL8 mice. Mice were pre-bled 7 days before the experiment and put into groups of five mice each for each dose tested. H4H15341P was administered at 1, 5, 10 and 25 mg/kg and isotype-matched (h IgG4) control with irrelevant specificity at 10 mg/kg by single-dose subcutaneous injection on Day 0 of the study. Mice were bled (nonfasted) at days 2, 7, 14 and 21 after antibody injection and TG levels were determined in the serum by ADVIA® 1800 Chemistry System (Siemens). Averages were calculated for each time point. Results, expressed as (mean±SEM) of serum TG concentration, are shown in FIG. 1A.

Figure 2:
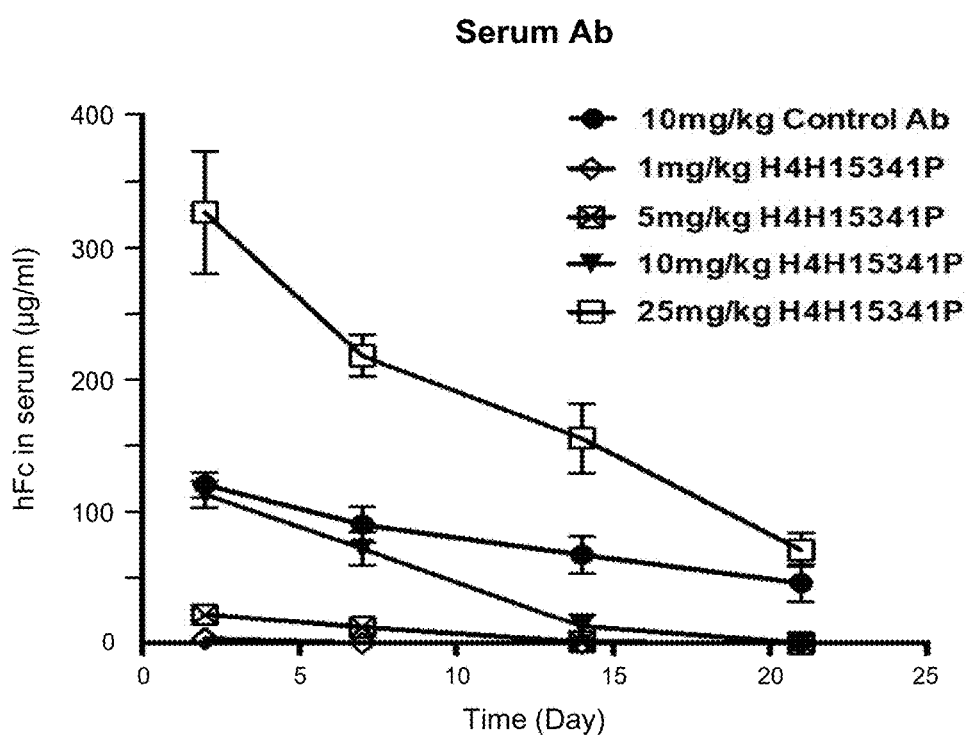
FIG. 2 shows the levels of circulating anti-human antibody after administration of one subcutaneous dose of H4H15341P at doses of 1, 5, 10, or 25 mg/kg.

Levels of circulating anti-human antibodies (Serum Ab) were determined using a standard ELISA assay. Briefly, plates were coated with a goat anti-human Fc antibody (Sigma-Aldrich) to capture Serum Ab. Serum was then added to the plates and captured antibodies were detected by chemiluminescence using a horseradish peroxidase (HRP) conjugated goat anti-human IgG antibody (Sigma-Aldrich). Results, expressed as (mean±SEM) are shown in FIG. 2. Control Ab refers to mice that received an isotype-matched control Ab.

Results:

The effect of 4 different doses of H4H15341P (anti-hANGPTL8) on circulating TG and cholesterol levels were tested in humanized ANGPTL8 mice. H4H15341P led to dose-dependent sustained significant reduction in serum TG (up to 66% average, compared to control mAb) with 5 mg/kg being the lowest efficacious dose. No effect was observed on total cholesterol levels.

Example 8. Evaluation of Lipoprotein Lipase (LPL) Activity after hANGPTL8 mAb Treatment in Humanized ANGPTL8 Mice The effect of hANGPTL8 mAb (H4H15341P) administration on LPL activity was evaluated in humanized ANGPTL8 mice. Mice were pre-bled 7 days before the experiment and put into groups of five mice each for each mAb tested. H4H15341P and Control Ab were administered at 10 mg/kg by single-dose subcutaneous injection on Day 0 of the study. On day 4 of the study, mice were dosed with heparin by intravenous injection via tail vein at 250 U/kg that releases LPL from vascular endothelial surfaces. Five minutes later mice were bled from the retro-orbital sinus and post-heparin plasma collected and fractionated to separate LPL from hepatic lipase using heparin-Sepharose chromatography. Post-heparin plasma was loaded onto 1.0-ml heparin-Sepharose HiTrap columns (GE Healthcare) controlled by the GE Akta Prime, equilibrated with 0.25 M NaCl, 20% glycerol, 1% BSA, 10 mM sodium phosphate, pH 6.5. The column was washed with 10 ml of the equilibration buffer and eluted with a 30 ml NaCl gradient (0.25-1.5 M in 20% glycerol, 1% BSA, 10 mM sodium phosphate, pH 6.5). Resulting fractions were pooled by hepatic lipase and LPL peaks and the lipase activities were assayed using Invitrogen Enzchek Lipase substrate (cat #E33955). The kinetic reaction was read on Molecular Devices SpectraMax i3 plate reader at 482 nm excitation/518 nm emission. Results, expressed as relative fluorescence units (RFU) (mean±SEM) are shown in FIGS. 3A and 3B. Control Ab refers to mice that received an isotype-matched negative control Ab.

Results

The results showed that administration of H4H15341P (anti-hANGPTL8) to humanized ANGPTL8 mice leads to a significant increase in LPL activity and has no effect on hepatic lipase activity.

Example 9. Lipid Tolerance Test in Humanized ANGPTL8 Mice Treated with hANGPTL8 mAb H4H15341P The effect of ANGPTL8 inhibition with the mAb H4H15341P on triglyceride clearance was evaluated by acute fat loading. Humanized ANGPTL8 mice were pre-bled 8 days before the experiment and put into groups of 6 mice each for each mAb tested. H4H15341P and isotype-matched control Ab were administered at 10 mg/kg by single-dose subcutaneous injection on Day 0 of the study. On day 4 of the study mice were fasted for 4 hours following intravenous administration of 20% intralipid (Baxter Healthcare, IL) at 2.5 µl/g body weight. TG level was evaluated in blood collected from the tail vein at subsequent time points. Results, expressed as (mean±SEM) of TG concentration are shown in FIG. 4. Control Ab refers to mice that received an isotype-matched negative control Ab.

Results

Administration of H4H15341P (anti-hANGPTL8) to humanized ANGPTL8 mice leads to a significantly lower TG level after acute fat load compared to control antibody. These data suggest that H4H15341P, by blocking ANGPTL8, promotes accelerated TG clearance from the circulation.

Example 10. HiSense Linear Epitope Mapping for Angiopoietin-Like Protein 8

Pepscan analysis using HiSense linear peptides was employed to establish linear epitopes for antibodies H4H15341P and H4H15367P2. The study was conducted at Pepscan Presto BV, (Zuidersluisweg 2, 8243RC Lelystad, The Netherlands). All Pepscan data is stored in the software package Peplab™, a proprietary database application developed in-house and built on a PostgreSQL storage back-end.

Synthesis of Peptides

To reconstruct epitopes of the target molecule, a library of peptides was synthesized. An amino functionalized polypropylene support was obtained by grafting with a proprietary hydrophilic polymer formulation, followed by reaction with t-butyloxycarbonyl-hexamethylenediamine (BocHMDA) using dicyclohexylcarbodiimide (DCC) with Nhydroxybenzotriazole (HOBt) and subsequent cleavage of the Boc-groups using trifluoroacetic acid (TFA). Standard Fmocpeptide synthesis was used to synthesize peptides on the amino-functionalized solid support by custom modified JANUS liquid handling stations (Perkin Elmer).

Coupling of Angiopoietin-Like Protein 8 onto the Array

The target protein was coupled on the mini-card as a positive control. To couple Angiopoietin-like protein 8 (hANGPTL8-mFc) onto the arrays, two cross-linking agents were used—m-maleimidobenzoyl-Nhydroxysuccinimide ester (MBS) and glutaraldehyde (GDA). For MBS 40 µl of hANGPTL8-mFc were mixed with 1 µl of MBS (2 mg/ml), incubated for 45 min at room temperature, and then applied onto the array at positions containing the linker motif CGGCGG (SEQ ID NO:346). For the GDA linking, 0.05% GDA in phosphate buffer (pH 5.0) was applied onto the array, incubated at room temperature for 4 hours, then hANGPTL8-mFc at concentration 5 or 20 µg/ml in phosphate buffer pH 8.0 was added onto the array on positions containing Gly only to allow coupling to the free N terminus.

ELISA Screening

The binding of antibody to each of the synthesized peptides was tested in a PEPSCAN-based ELISA. The peptide arrays were incubated with primary antibody solution (overnight at 4° C.). After washing, the peptide arrays were incubated with a 1/1000 dilution of an appropriate antibody peroxidase conjugate (goat anti-human HRP conjugate, Southern Biotech, catalog no. 2010-05) for one hour at 25° C. After washing, the peroxidase substrate 2,2′-azino-di-3-ethylbenzthiazoline sulfonate (ABTS) and 20 µl/ml of 3 percent $H_2O_2$ were added. After one hour, the color development was measured. The color development was quantified with a charge coupled device (CCD)—camera and an image processing system.

Screening Details

Antibody binding depends on a combination of factors, including concentration of the antibody and the amounts and nature of competing proteins in the ELISA buffer. Also, the pre-coat conditions (the specific treatment of the peptide arrays prior to incubation with the experimental sample) affect binding. These details are summed up as follows:

| Label | Dilution | Sample buffer | Pre-conditioning |
| --- | --- | --- | --- |
| H4H15341P | 1 µg/ml | 100% SQ | 100% SQ |
| H4H15367P2 | 1 µg/ml | 100% SQ | 100% SQ |
| Negative isotype control | 1 µg/ml | 100% SQ | 100% SQ |

For the Pepscan Buffer and Preconditioning (SQ), the numbers indicate the relative amount of competing protein (a combination of horse serum and ovalbumin).

Data Processing

The values obtained from the CCD camera range from 0 to 3000 mAU, similar to a standard 96-well plate ELISA-reader. The results are quantified and stored into the Peplab database. Occasionally, a well contains an air-bubble resulting in a false-positive value, the cards are manually inspected, and any values caused by an air-bubble are scored as 0.

Synthesis Quality Control

To verify the quality of the synthesized peptides, a separate set of positive and negative control peptides was synthesized in parallel. These were screened with antibody 57.9 (Posthumus, et al. 1990 *J Virol* 64:3304-3309).

Results

Design of Peptides

The following sets of peptides were synthesized on the target sequence:

Human ANGPTL8, mature sequence, amino acids 22-198 from NP_061157.3

```
                                                         (SEQ ID NO: 347)
  1  APMGGPELAQ HEELTLLFHG TLQLGQALNG VYRTTEGRLT KARNSLGLYG   50

51  RTIELLGQEV SRGRDAAQEL RASLLETQME EDILQLQAEA TAEVLGEVAQ  100

101  AQKVLRDSVQ RLEVQLRSAW LGPAYREFEV LKAHADKQSH ILWALTGHVQ  150

151  RQRREMVAQQ HRLRQIQERL HTAALPA                           177
```

The antibodies were tested for binding a series of 15-mer peptides covering the full sequence of ANGPTL8, each peptide offset by one amino acid from the next. Also included were double alanine ("AA") substitutions within the series of tested peptides for finer epitope analysis.

SET 1. Mimic: linear. Type: LIN

Description Peptides of length 15 derived from the target sequence of Angiopoietin-like protein 8 with an offset of one residue.

Sequences (first 10)

| | |
| --- | --- |
| APMGGPELAQHEELT | (SEQ ID NO: 348) |
| PMGGPELAQHEELTL | (SEQ ID NO: 349) |
| MGGPELAQHEELTLL | (SEQ ID NO: 350) |
| GGPELAQHEELTLLF | (SEQ ID NO: 351) |
| GPELAQHEELTLLFH | (SEQ ID NO: 352) |
| PELAQHEELTLLFHG | (SEQ ID NO: 353) |
| ELAQHEELTLLFHGT | (SEQ ID NO: 354) |
| LAQHEELTLLFHGTL | (SEQ ID NO: 355) |
| AQHEELTLLFHGTLQ | (SEQ ID NO: 356) |
| QHEELTLLFHGTLQL | (SEQ ID NO: 357) |

SET 2. Mimic: linear. Type: LIN.AA

Description Peptides of set 1, but with residues on positions 10 and 11 replaced by Ala. When a native Ala would occur on either position, it is replaced by Gly. The order of peptides in this set was randomized. The actual order on the array is shown.

Sequences (First 10)

TAEVLGEVAAGQKVL (SEQ ID NO: 358)

VYRTTEGRLAAARNS (SEQ ID NO: 359)

GVYRTTEGRAAKARN (SEQ ID NO: 360)

VQRLEVQLRAGWLGP (SEQ ID NO: 361)

LTGHVQRQRAAMVAQ (SEQ ID NO: 362)

VLKAHADKQAAILWA (SEQ ID NO: 363)

LRDSVQRLEAALRSA (SEQ ID NO: 364)

RREMVAQQHAARQIQ (SEQ ID NO: 365)

VSRGRDAAQAARASL (SEQ ID NO: 366)

AYREFEVLKGAADKQ (SEQ ID NO: 367)

The raw ELISA results of the screening were provided and plotted (box plot, data not shown) to depict each dataset and indicate the average ELISA signal, the distribution, and the outliers within each dataset. Depending on experiment conditions (amount of antibody, blocking strength, etc.), different distributions of ELISA data were obtained.

Antibody H4H15367P2

When tested under high stringency conditions, antibody H4H15367P2 avidly bound only one linear peptide comprised of sequence 1APMGGPELAQHEELT15 (SEQ ID NO: 348). This sample was tested twice under the same conditions and repeatedly yielded the same result. Antibody H4H15367P2 also strongly bound Angiopoietin-like protein 8, which was coupled onto the array as a positive control. Interestingly, somewhat weaker binding was obtained with the target protein coupled using MBS when compared to GDA coupling.

Antibody H4H15341P

When tested under high stringency conditions, antibody H4H15341P avidly bound a series of linear peptides, which contain common sequence $_{150}$QRQRREMVAQ$_{159}$ (SEQ ID NO: 368). Comparison of intensity profiles recorded on set 1 (native linear epitope mimics) and set 2 (double Ala mutants) indicates that residues R154, E155, and Q159 are essential for antibody binding. Antibody H4H15341P also strongly bound Angiopoietin-like protein 8, which was coupled onto the array as a positive control, regardless of the immobilization.

Negative Isotype Control

Negative isotype control did not bind any peptide present on the array. Furthermore, no detectable binding was recorded with Angiopoietin-like protein 8, which was coupled onto the array as a positive control. Negative isotype control was additionally tested with goat anti-human secondary conjugate used in Pepscan ELISA. The antibody can be recognized by this secondary.

Conclusion

Three antibodies provided for this study were tested on HiSense peptide arrays. It was possible to establish tentative linear epitopes for two antibodies. Despite repeated incubations, antibody Negative isotype control did not bind to the array. Core tentative epitopes identified in this study are listed as follows:

| Antibody | Core epitope |
|---|---|
| H4H15341P | $_{150}$QRQRREMVAQ$_{159}$ (SEQ ID NO: 368) |
| H4H15367P2 | $_{1}$APMGGPELAQHEELT$_{15}$ (SEQ ID NO: 348) |
| Negative isotype control | —. |

Thus, Antibodies H4H15341P and H4H15367P2 recognize distinct linear sequences within C- and N-termini respectively. The fact that signal obtained for antibody H4H15367P2 with MBS coupling was less than with GDA coupling, together with its localization on the extreme N terminus indicate that the N terminal amine itself may be part of the epitope. Additionally, for antibody H4H15341P double alanine mutants served to pinpoint residues that are critical for binding (residues underlined, above).

Antibody H4H15341P targets a C-terminal region of Angiopoietin-like protein 8, while H4H15367P2 targets the very N-terminus. Antibody Negative isotype control did not bind to the array.

Example 11: ANGPTL8 Blockade with a Monoclonal Antibody Promotes Plasma Triglyceride Clearance, Energy Expenditure and Weight Loss in Mice In the following example, ANGPTL8 blockade with a fully human monoclonal antibody is shown to decrease plasma TGs, increase LPL activity, and reduce body weight and fat content in mice. In addition to the data above, these data indicate that ANGPTL8 inhibition is a target for the treatment of hypertriglyceridemia and with added benefits on fat content and body weight.

Materials and Methods

Antibodies and Protein Reagents

As noted above, H4H15341P was derived using Regeneron's Velocimmune® technology platform (Macdonald, L. E., et al. 2014. PNAS USA 111: 5147-5152; Murphy, A. J et al. 2014. PNAS USA 111: 5153-5158) and is a fully human monoclonal antibody with high affinity to ANGPTL8 from monkey and humans. H4H15341P has a human IgG4 constant region with a stabilizing mutation in the hinge region (serine to proline in position 108) (Schreier, P. H., et al. 1981 *PNAS USA* 78(7):4495-4499) to minimize half-antibody formation (Labrijn, A. F., et al. 2009. Nature biotechnology 27: 767-771). An isotype-matched antibody with irrelevant specificity was used as control.

Binding Studies

The binding of H4H15341P to human and monkey ANGPTL8 was studied using surface plasmon resonance imaging (SPRi) based MASS-1 biosensor in 10 mM Hepes pH 7.4, 150 mM NaCl, 3 mM EDTA, and 0.05% v/v Surfactant Tween-20 (HBS-ET) running buffer at 25° C. The HCA sensor surface was first amine coupled with goat anti-mouse IgG2a polyclonal antibody (Southern Biotech, #1080-01) and around 30RU of ANGPTL8 expressed with C-terminal mouse IgG2a Fc tag (hANGPTL8-mFc) or monkey ANGPTL8 expressed with C-terminal mouse IgG2a Fc tag (mfANGPTL8-mFc) was captured. Different concentrations of H4H15341P, prepared in HBS-ET running buffer were later injected over hANGPTL8-mFc or mfANGPTL8-mFc captured surfaces for 4 minutes at a flow rate of 304/minute followed by the dissociation of bound mAb in HBS-ET running buffer for 10 minutes. Injection of running buffer without analyte was performed to allow subtraction of baseline drift resulting from the natural dissociation of captured mAb from the coupled goat anti-mouse IgG2a polyclonal antibody surface. The raw binding data were aligned to the start of the analyte injection followed by subtraction from the reference flow cell. The processed data were later analyzed using Scrubber (v. 2.0c, BioLogic Software), wherein the second reference subtraction using control buffer injections was performed. The association rate (ka), dissociation rate (ka) and dissociation constant (KD) were calculated by globally fitting the double reference subtracted binding data to a 1:1 Langmuir binding model with mass transport limitation using Scrubber 2.0c software.

Studies in Mice

Humanized ANGPTL8 mice (ANGPTL8$^{hum/hum}$ mice) were generated on 75% C57BI/6 and 25% 129S6/SvEv background using VelociGene technology (Valenzuela, D. M., et al. 2003. Nature biotechnology 21: 652-659). VelociGene allele identification number is VG7182. All procedures were conducted in compliance with protocols approved by the Regeneron Pharmaceuticals Institutional Animal Care and Use Committee. H4H15341P and control antibody were diluted with sterile PBS for subcutaneous (S.C.) injection into mice.

Single Administration Studies:

Male ANGPTL8$^{hum/hum}$ mice were maintained on chow diet (5001, LabDiet) and fed ad libitum. To establish a baseline for serum chemistry parameters, serum samples were collected 7 days prior to antibody administration in the non-fasted state. On study day 0, mice were sorted into treatment groups based on their serum TG levels. Mice (n=5/group) (ad libitum) were administered single S.C. injections of H4H15341P or control antibody at the indicated doses. Subsequent serum samples were collected from non-fasted mice over the duration of the study and analyzed for serum chemistry parameters and human ANGPTL8 levels. Post-heparin plasma LPL activity was measured 4 days after single administration of H4H15341P (10 mg/kg). Post-heparin plasma was fractionated on a heparin column to separate hepatic lipase and LPL as described previously (Wang, Y., F. et al. 2013. PNAS USA 110: 16109-16114). TG hydrolase activity was measured using EnzCheck substrate (Thermo Fisher Scientific) as described elsewhere (Basu, D., J. Manjur, and W. Jin. 2011. The Journal of Lipid Research 52: 826-832). Lipid tolerance tests were performed 4 days after single dose of H4H15341P (10 mg/kg). Mice were fasted for 2 hr before intravenous administration of 20% intralipid (Baxter Healthcare) at 2.5 µl/g body weight. TGs were evaluated in blood collected from tail at subsequent time points.

Multiple Administration Studies:

Seven days prior to antibody administration (day −7), baseline serum chemistries were measured in non-fasted animals. On day −6, male ANGPTL8$^{hum/hum}$ mice were placed on high fat high cholesterol (HFHC) diet (21% fat, 0.21% cholesterol, Research Diets). On study day 0, mice were sorted into treatment groups based on their serum TGs and body weights (n=8/group). Mice were injected with H4H15341P or control antibody once a week (S.C., 10 mg/kg) for 16 weeks. Body weights were measured weekly. Body composition and metabolic analysis was evaluated at 15 and 14 weeks, respectively. Mice were sacrificed one week after the last antibody injection and liver, heart, muscle, epididymal and subcutaneous white and brown adipose tissues were collected.

Serum Chemistry Analyses

Serum TG, total cholesterol (TC), LDL-C and HDL-C levels were determined in serum using an ADVIA® 1800 blood chemistry analyzer (Bayer, Leverkusen, Germany). Lipoproteins separation by HPLC was performed as described previously (Gusarova, V., et al. 2015. J Lipid Res 56: 1308-1317).

Body Composition, Metabolic Rate and Food Intake Measurements

Body composition was measured using µCT using the Quantum FX micro CT preclinical in vivo imaging system (Caliper Life Sciences) as described elsewhere (Mastaitis, J., et al. 2015. PNAS USA 112: 1845-1849). Metabolic cage data were generated using the Oxymax Lab Animal Monitoring System: CLAMS (Columbus Instruments). Mice were individually monitored in cages with center feeds for 96 hr. Data generated in the first 24 hr were omitted from the analysis. Food intake was measured continuously and divided into calories consumed per light and dark phase of the light cycle. VO$_2$ and VCO$_2$ were measured in 17-min intervals over a 4-d span and plotted over time in hours. Energy expenditure was calculated as a function of the respiratory quotient and the oxygen consumption, normalized to body weight. In addition, as the groups had divergent body weights at the time of analysis, energy expenditure was expressed as Kcal/hr per mouse using an adjusted mean body weight of the two groups combined. This was achieved using analysis of covariance (ANCOVA) with body weight as the covariance, as described (Arch J R, et al. 2006. Int J Obes (Lond) 30(9):1322-1331; Whittle A J, et al. 2015. Nat Commun 6:8951). Briefly, the adjusted energy expenditure for each animal was calculated as Y=y−b(x−X) and plotted as mean±SEM for each group, where Y is single animal adjusted energy expenditure (Kcal/hr), y—single animal energy expenditure (Kcal/hr), x—single animal body weight (kg), X—adjusted mean body weight of the 2 treatment groups combined (kg), b—the slope of the line of energy expenditure plotted versus body weight for each animal and each treatment group calculated by linear regression analysis.

Glucose Measurements, Glucose and Insulin Tolerance Tests

Blood glucose was measured from tail tip using Accu-Chek glucometer (Roche, Basel, Switzerland). For oral glucose tolerance test mice were fasted overnight (16 hr) followed by oral gavage of glucose at 2 g/kg body weight. Blood glucose level was evaluated at 0, 15, 30, 60 and 120 min post-injection. For insulin tolerance test mice were fasted for 4 hr followed by intraperitoneal injection of 2 U/Kg of human insulin (Eli Lilly). Blood glucose level was evaluated at 0, 15, 30, 60 and 120 min post-injection.

TG Tissue Content

Liver, heart, gastrocnemius muscle, epididymal and subcutaneous white adipose tissues, and brown adipose tissue were collected at the end of multiple administration of H4H15341P to ANGPTL8hum/hum mice and lipids were extracted as described (Folch J. et al. 1957. J Biol Chem. 226(1):497-509). Lipids were solubilized as outlined earlier (Carr T P Andresen C J, Rudel L L. 1993. Clinical biochemistry. 26(1):39-42). The levels of TG were measured using enzymatic assays (Infinity, Thermo Fisher Scientific) and normalized to wet tissue weight.

Study in Cynomolgus Monkeys

The study was performed at Crown Bioscience (Taicang, Jiangsu, China). Eighteen spontaneous hypertriglyceridemic monkeys were selected based on their non-fasted serum TG levels and divided into 3 groups. The monkeys were individually housed, had free access to water and were fed twice daily with a complete nutritionally balanced diet (Shanghai Shilin Biotechnology), enriched with seasonal fruits and vegetables. All animal procedures were approved by the Crown Bioscience Institutional Animal Care and Use Committee and performed according to guidelines approved by the Association for Assessment and Accreditation of Laboratory Animal Care. On day 0 the monkeys were administrated H4H15341P at 3, 7 or 10 mg/kg. Blood (4 ml) was collected into BD sterile venous blood collection tubes (ACCU-CHEK Active, Roche) from non-fasted animals at 1- to 5-day intervals up to day 45. After TG levels for all animals returned to baseline, animals were allowed to washout for at least 2 weeks, and then 5 animals were selected for the treatment with saline. Blood was collected on consecutive days after saline administration on the same schedule as the H4H15341P-injected groups. Serum TG, TC, LDL-C and HDL-C were measured by ADVIA®2400 (Siemens).

Data Analysis

All data are shown as mean±SEM. Statistical analyses were performed utilizing Graph Pad Prism 6.0 software. LPL and HL activities in H4H15341P and control antibody-treated mice were compared by Welch's t-test. All other parameters were analyzed by two-way ANOVA with repeated measures. If a significant F ratio was obtained with two-way ANOVA, post-hoc analysis was conducted between groups with Bonferroni's or Sidak's post-tests. In the monkey study, the average of each parameter on day −15, −7, and 0 was used as the baseline value.

Results

In Vitro Characterization of ANGPTL8 Blocking Antibody

Figure 9A:
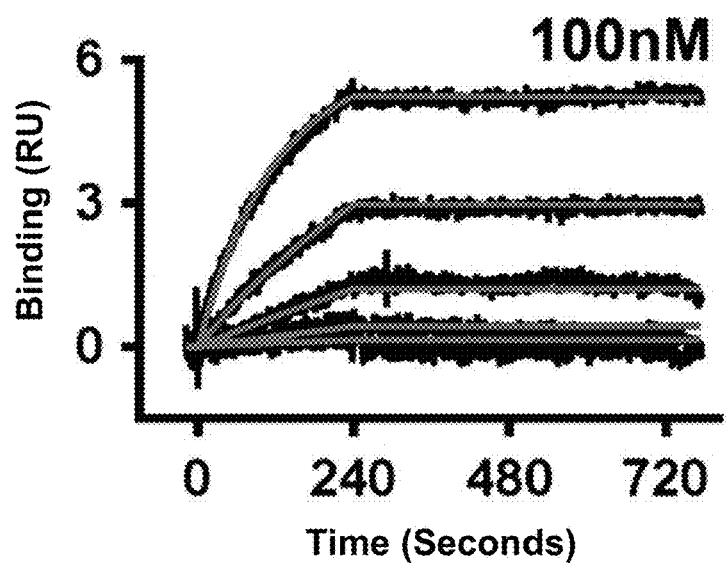
FIGS. 9A and 9B. Sensorgrams for H4H15341P binding to hANGPTL8-mFc and mfANGPTL8-mFc. Around 30RU of hANGPTL8-mFc (9A) or mfANGPTL8-mFc (9B) was first captured on the goat anti-mouse IgG2a polyclonal antibody immobilized HCA surface. Different concentrations of H4H15341P, serially diluted by three-fold in HBS-ET running buffer were later injected for 4 minutes followed by a dissociation step of 10 minutes. Binding sensorgrams are shown in black while global fits generated to calculate kinetic values are shown in grey. Highest antigen concentration used to fit the binding data is also provided and results of the kinetic analysis are tabulated in Table 20.
Figure 9B:
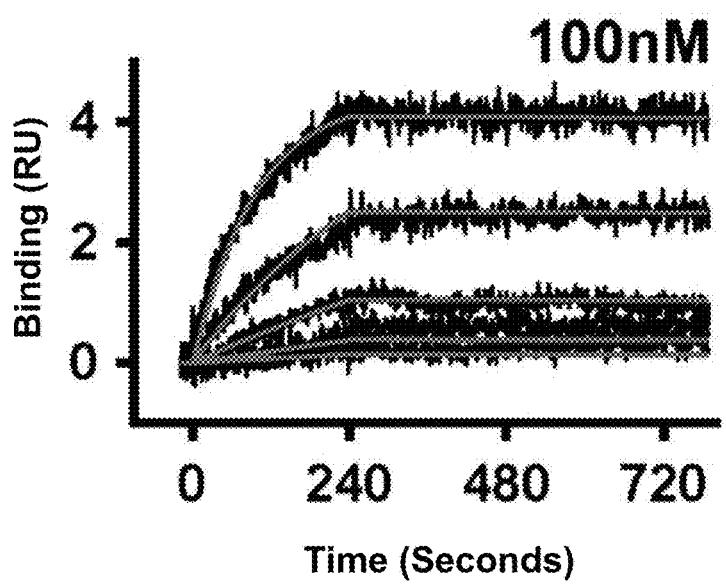
Figure 10A:
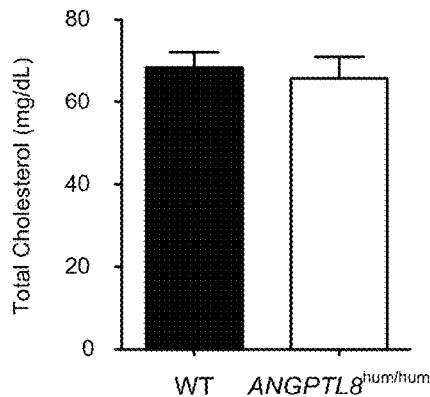
FIGS. 10A, 10B, 10C, and 10D. Metabolic parameters of H4H15341P and control antibody treated HFHC-fed ANGPTL8$^{hum/hum}$ mice. Circulating lipid levels were evaluated from the serum collected from male ANGPTL8$^{hum/hum}$ mice and their wild type littermates. (10A) Total cholesterol, (10B) triglycerides, (10C) LDL-C, and (10D) HDL-C are shown. All values are mean±SEM. Statistical analysis was conducted by Welch's t-test. *P<0.01
Figure 10B:
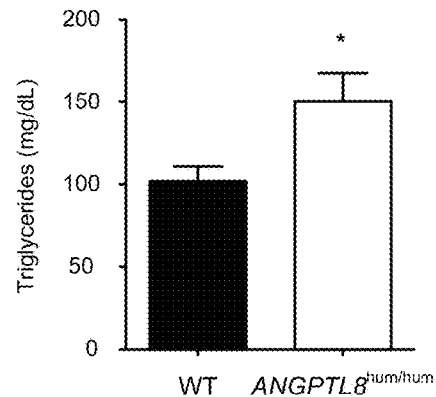
Figure 10C:
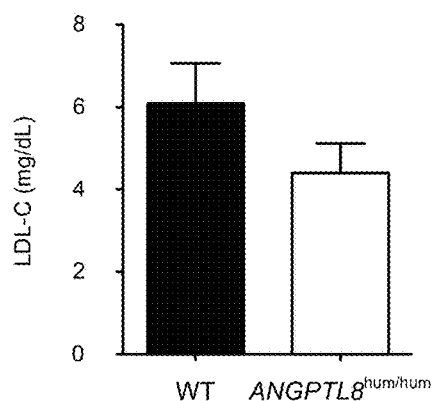
Figure 10D:
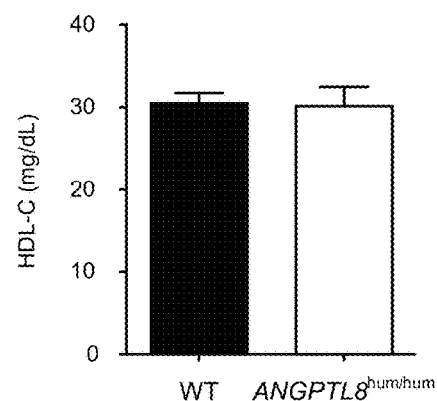

The relative affinities of ANGPTL8 blocking antibody H4H15341P to human, mouse and monkey ANGPTL8 were compared using surface plasmon resonance. H4H15341P binds human and monkey ANGPTL8 with comparable affinities (Table 20 and FIGS. 9A and 9B). H4H15341P does not bind mouse ANGPTL8 or human or mouse ANGPTL3 or ANGPTL4 (data not shown).

TABLE 20

Summary of binding kinetic parameters for the interaction of H4H15341P with hANGPTL8-mFc or mfANGPTL8-mFc.

| Capture Surface | Kinetic Binding Parameters | | | |
|---|---|---|---|---|
| | $k_a$ (M$^{-1}$s$^{-1}$) | $k_d$ (s$^{-1}$) | $K_D$ (M) | t½ (min) |
| hANGPTL8-mFc | $8.5 \times 10^4$ | $1 \times 10^{-5}$* | $\leq 1.17 \times 10^{-10}$ | $\geq 1155$ |
| mfANGPTL8-mFc | $1.16 \times 10^5$ | $1 \times 10^{-5}$* | $\leq 8.6 \times 10^{-11}$ | $\geq 1155$ |

*indicates that no dissociation of H4H15341P was observed from hANGPTL8-mFc or mfANGPTL8-mFc captured surfaces and $k_d$ value was manually fixed to $1 \times 10^5$ s$^{-1}$ while fitting the binding curves.

Figure 5A:
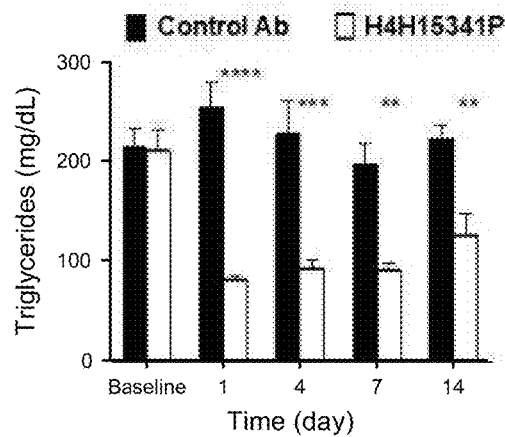
FIGS. 5A, 5B, 5C, 5D, 5E, and 5F show that mAb H4H15341P reduces serum triglyceride in ANGPTL8$^{hum/hum}$ mice. Serum samples were collected from non-fasted male ANGPTL8$^{hum/hum}$ mice (n=5/group) 7 days before (baseline) and at the indicated days following a single subcutaneous injection of H4H15341P or control antibody (10 mg/kg). Serum triglyceride (5A) and cholesterol (5B) were measured enzymatically. Serum (20 μl) from each mouse collected 7 days after treatment with H4H15341 or control antibody was size-fractionated by HPLC. Triglyceride (5C) and cholesterol (5D) were measured in each fraction. (5E) Total (free plus antibody-bound) serum levels of human ANGPTL8 were measured by ELISA. (5F) Dose-dependent lowering of serum triglycerides by H4H15341P in chow-fed ANGPTL8$^{hum/hum}$ mice measured 7 and 14 days after antibody administration. Values are mean±SEM, except for the chromatograms where only mean values are shown. Statistical analysis was conducted by 2-way ANOVA with Sidak's correction post-test. P<0.01; *P<0.001; ****P<0.0001.
Figure 5B:
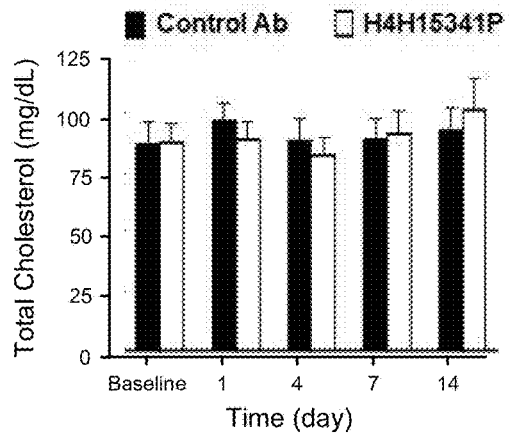
Figure 5C:
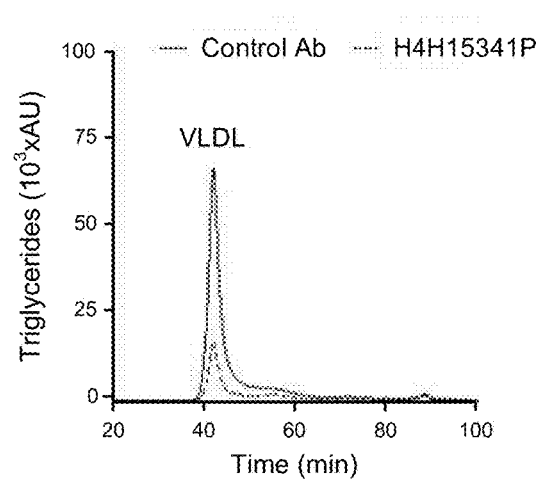
Figure 5D:
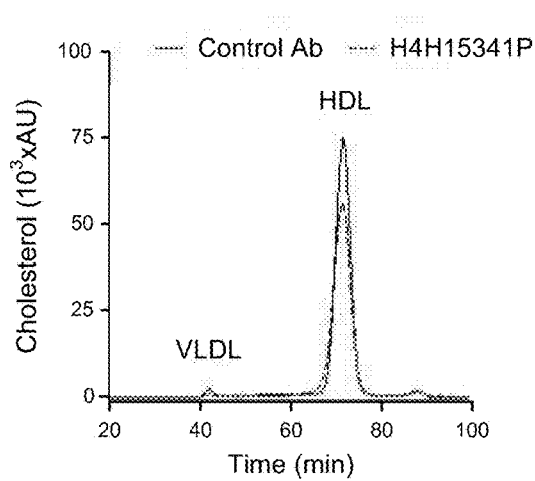
Figure 5E:
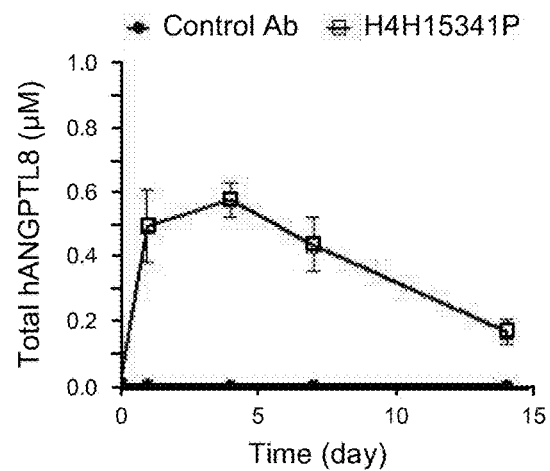
Figure 5F:
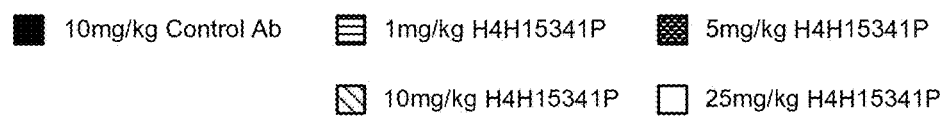
Figure 5F:
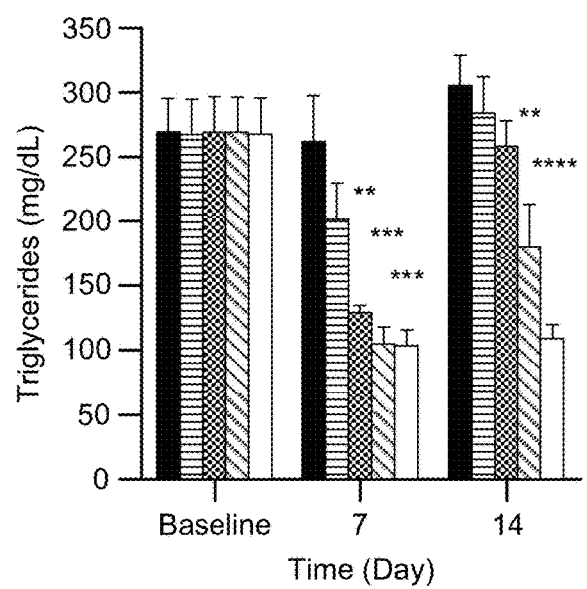

ANGPTL8 Antibody Blockade Lowers Serum Triglycerides Via Upregulation of Lipoprotein Lipase Activity To evaluate the effect of human ANGPTL8 antibody on serum lipid levels, humanized ANGPTL8 mice (ANGPTL8$^{hum/hum}$) were generated. These mice had slightly increased baseline TGs with other lipids similar to wildtype mice (FIGS. 10A-10D). Single administration of H4H15341P (10 mg/kg) to chow fed ANGPTL8$^{hum/hum}$ mice significantly reduced circulating TGs compared to control antibody treatment (FIG. 5A), but did not affect total cholesterol levels (FIG. 5B). HPLC separation of serum lipids confirmed that ANGPTL8 inhibition reduced VLDL-TG (FIG. 5C). The reduction in TG was sustained for 14 days and was associated with marked increase in plasma levels of ANGPTL8 (FIG. 5E). The effects of increasing doses of H4H15341P on circulating TGs in chow-fed ANGPTL8$^{hum/hum}$ mice were evaluated. Single administration of H4H15341P at 5, 10 and 25 mg/kg caused a progressive reduction in TGs up to 60% of control levels (FIG. 5F).

Figure 6A:
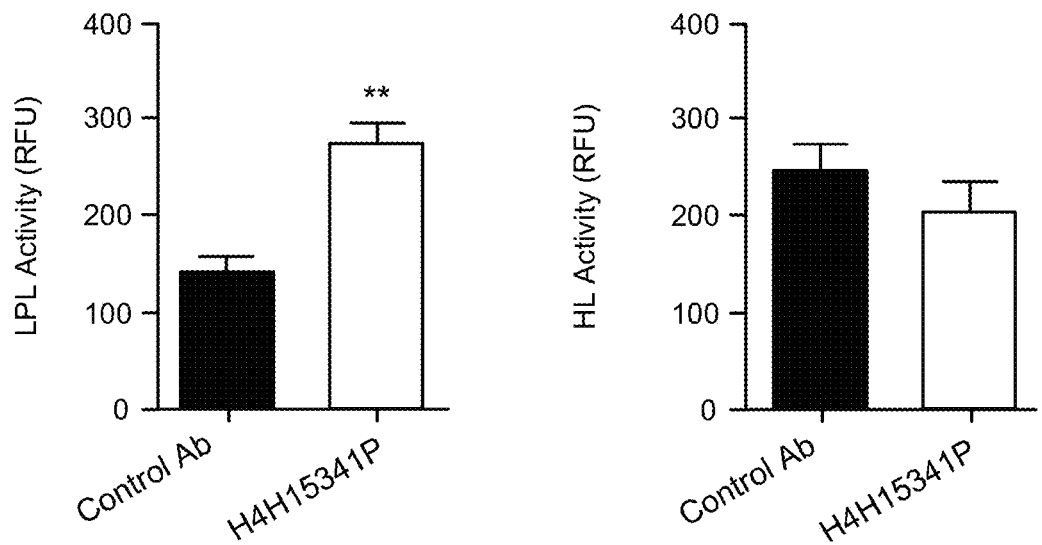
FIGS. 6A and 6B. H4H15341P increases LPL activity and improves triglyceride clearance in ANGPTL8$^{hum/hum}$ mice. (6A) Post-heparin plasma LPL and HL activity of chow-fed ANGPTL8$^{hum/hum}$ mice treated with H4H15341P or control antibody (10 mg/kg, n=5/group). Post-heparin plasma was pooled and fractionated on a heparin column to separate HL and LPL, and triglyceride hydrolase activity was measured. (6B) Effect of H4H15341P treatment on plasma triglyceride levels following a lipid tolerance test. Male ANGPTL8$^{hum/hum}$ mice were treated with H4H15341P or control antibody (10 mg/kg, n=5/group) 4 days prior to the intravenous administration of Intralipid (2.5 μl/g of 20% Intralipid). Values are mean±SEM. Statistical analysis was conducted by Welch's t-test (A) and repeated measures two-way ANOVA with Bonferroni's post-test (B). P<0.01, **P<0.0001. HL=hepatic lipase, LPL=lipoprotein lipase.
Figure 6B:
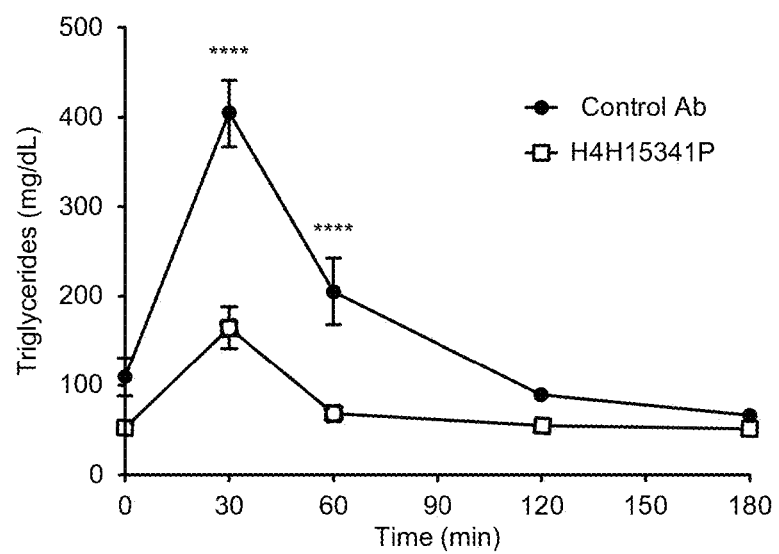

It was previously reported that Angptl8$^{-/-}$ mice increased TG clearance via upregulation of post-heparin plasma LPL activity (Wang, Y., et al. 2013. PNAS USA 110: 16109-16114). Consistent with this, ANGPTL8 blockade with H4H15341P increased post-heparin plasma LPL activity without changes in hepatic lipase activity (FIG. 6A). The increase in LPL plasma activity improved lipid tolerance in ANGPTL8$^{hum/hum}$ mice receiving H4H15341P (FIG. 6B). These data show that ANGPTL8 blockade with monoclonal antibody lowered plasma TGs through upregulation of LPL activity.

ANGPTL8 Antibody Inhibition Increases Energy Expenditure and Reduces Fat Content and Body Weight in ANGPTL8$^{hum/hum}$ Mice The effects of prolonged inhibition of ANGPTL8 on energy expenditure, body composition and body weight were evaluated in ANGPTL8$^{hum/hum}$ mice on high fat, high cholesterol (HFHC) diet. Weekly administration of H4H15341P (10 mg/kg) for 16 weeks caused marked and sustained reduction in postprandial circulating TG levels compared to control antibody (FIG. 7A). ANGPTL8 antibody also caused a gradual body weight reduction that reached statistical significance at week 12 (FIG. 7B). The reduction in body weight correlated with reduced body fat volume as determined by μCT (FIG. 7C). No change in the volume of lean tissue was detected.

Figure 7E:
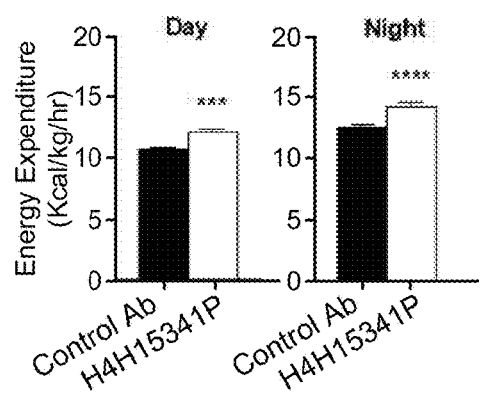
Figure 7F:
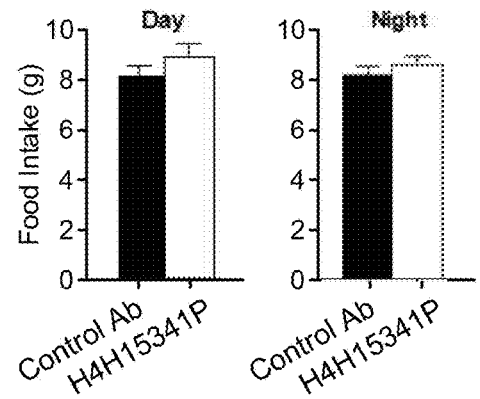
Figure 7G:
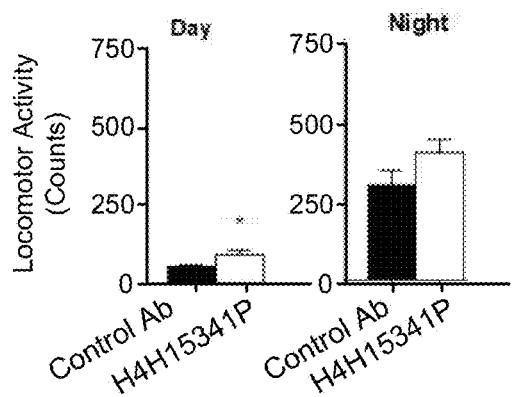
Figure 11A:
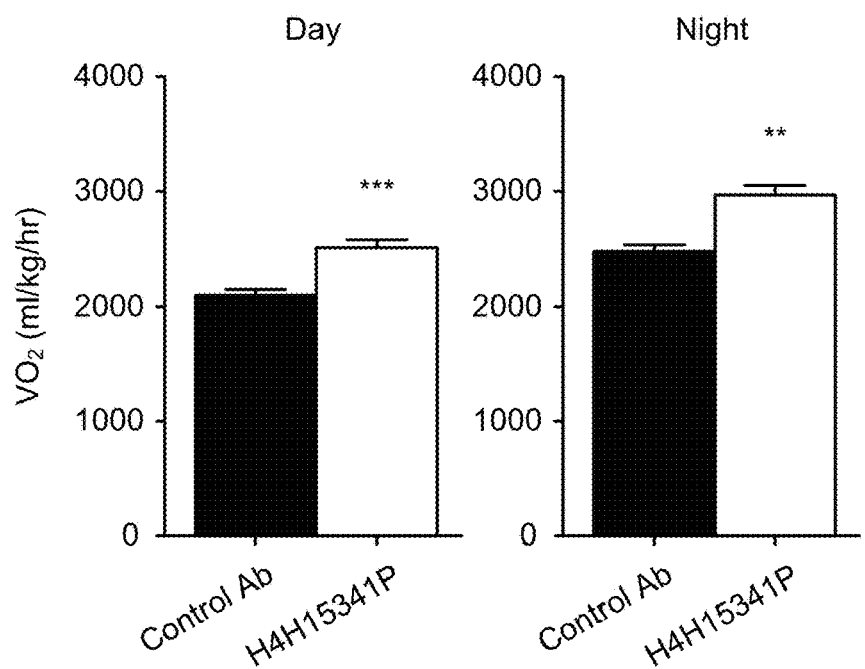
FIGS. 11A, 11B, 11C, and 11D. Multiple dose administration of H4H15341P increases energy expenditure, O$_2$ consumption, and CO$_2$ production in HFHC-fed ANGPTL8$^{hum/hum}$ mice. Changes in O$_2$ consumption (11A) and CO$_2$ production (11B) were evaluated during light and dark cycles in H4H15341P and control antibody treated mice in the study described in FIGS. 7A-7G. Indirect calorimetry expressed as a scatter plots for light and dark cycles showing the correlation between energy expenditure and body weight for H4H15341P and control antibody treated mice in the study described in FIG. 11C and as an adjusted mean energy expenditure for light and dark cycles for an adjusted mean body weight of 0.03688 kg (11D), using analysis of covariance. All values are mean±SEM. Statistical analysis was conducted by Welch's t-test. *P<0.05; P<0.01; *P<0.001; ****P<0.0001.
Figure 11B:
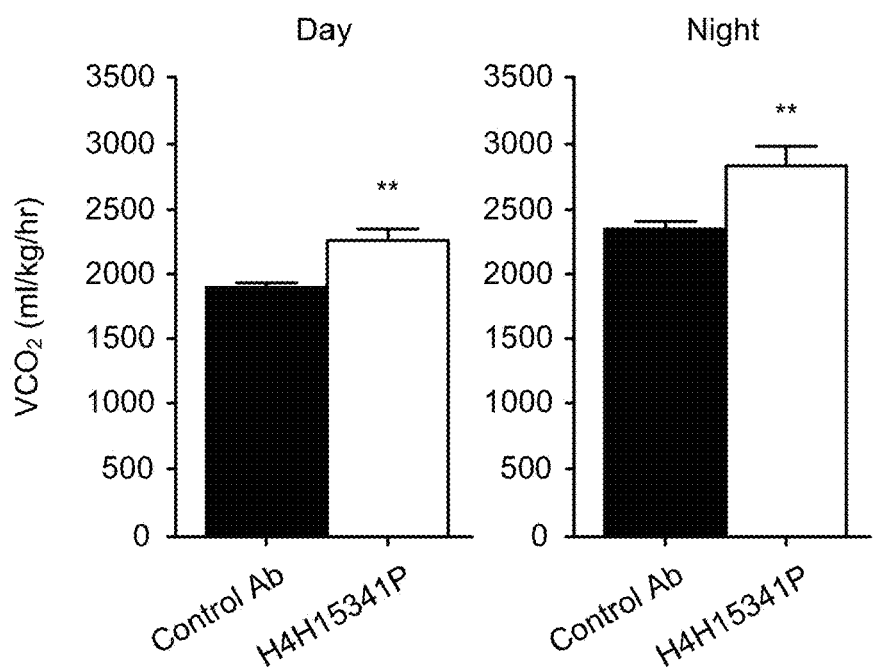
Figure 11C:
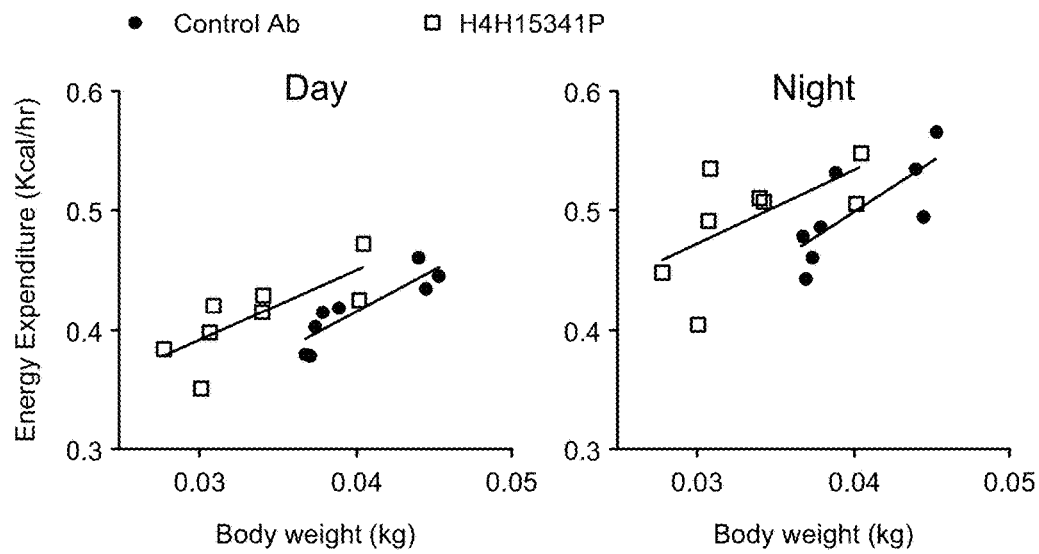
Figure 11D:
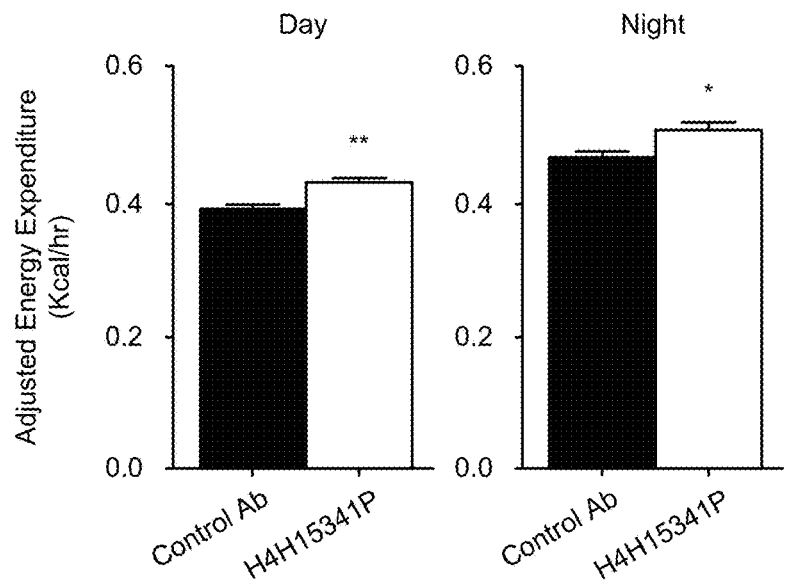
Figure 12A:
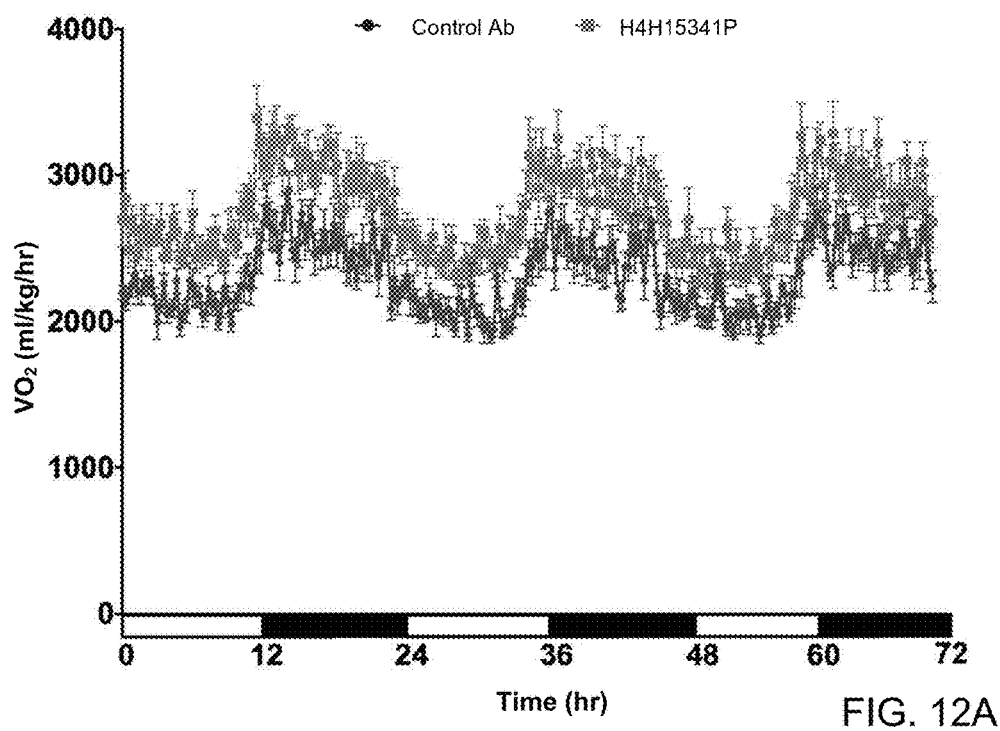
FIGS. 12A, 12B, 12C, 12D, 12E, and 12F. Metabolic parameters of H4H15341P and control ab treated HFHC-fed ANGPTL8$^{hum/hum}$ mice. Data are presented as continuous measurements over 72 h during the light and dark cycles for VO$_2$ (12A), VCO$_2$ (12B), respiratory quotient (RER) (12C), food intake (12E), energy expenditure (12D) and locomotor activity (12F). All groups had eight animals. Values are mean±SEM.
Figure 12B:
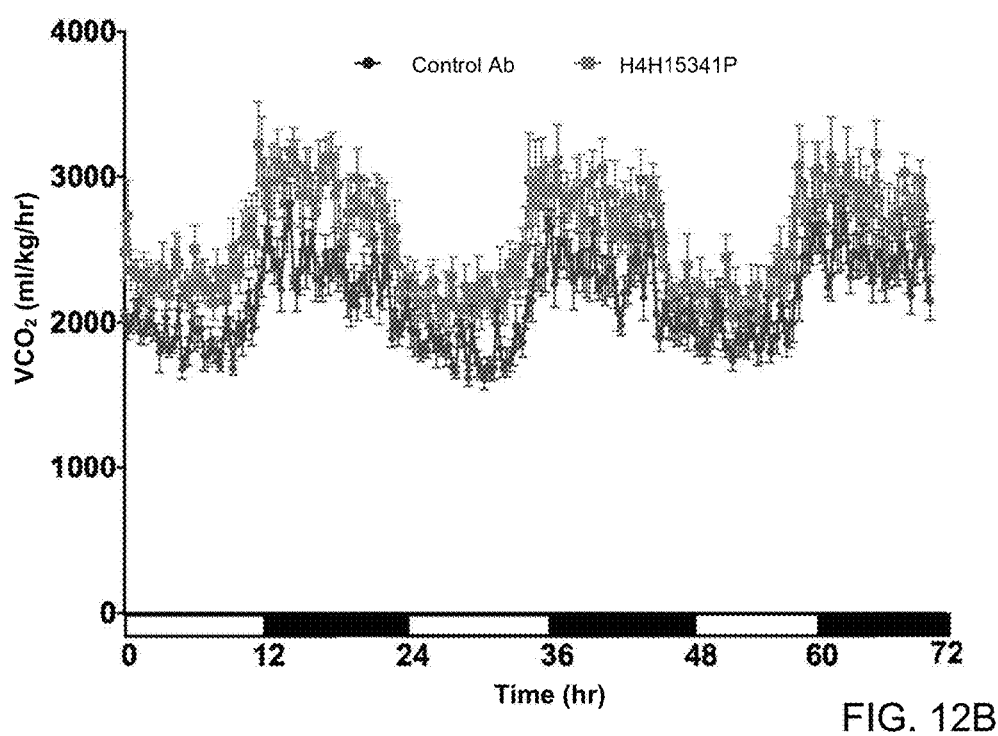
Figure 12C:
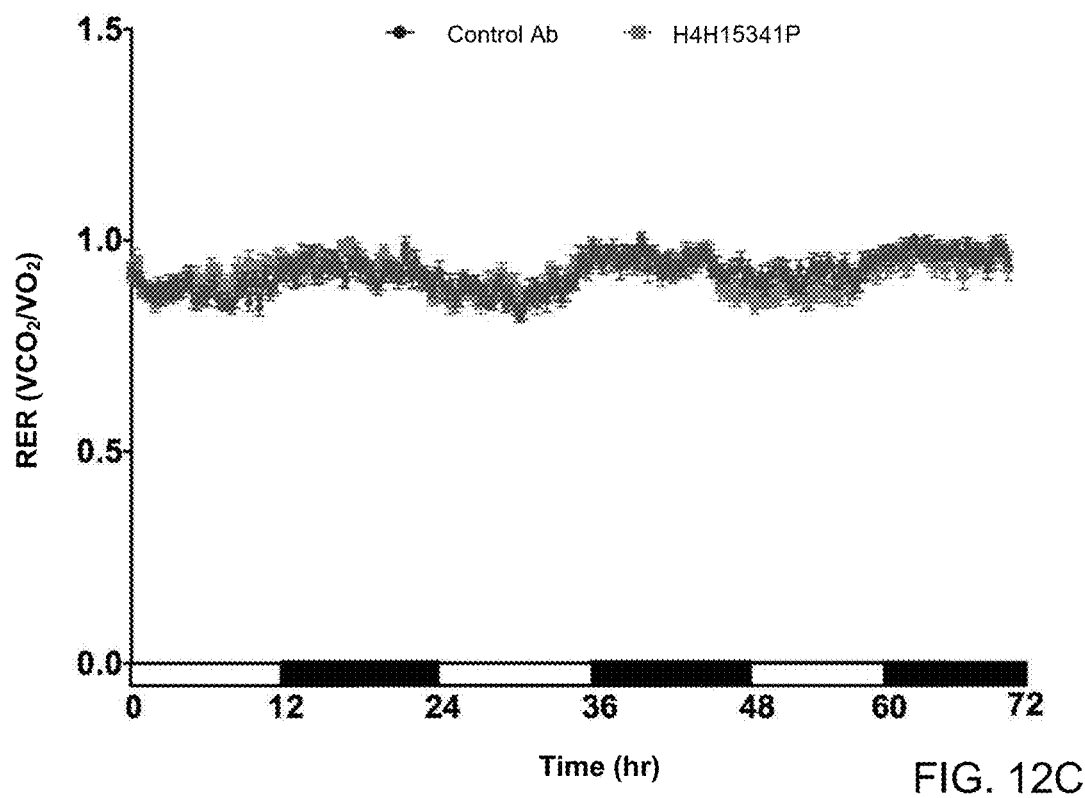
Figure 12D:
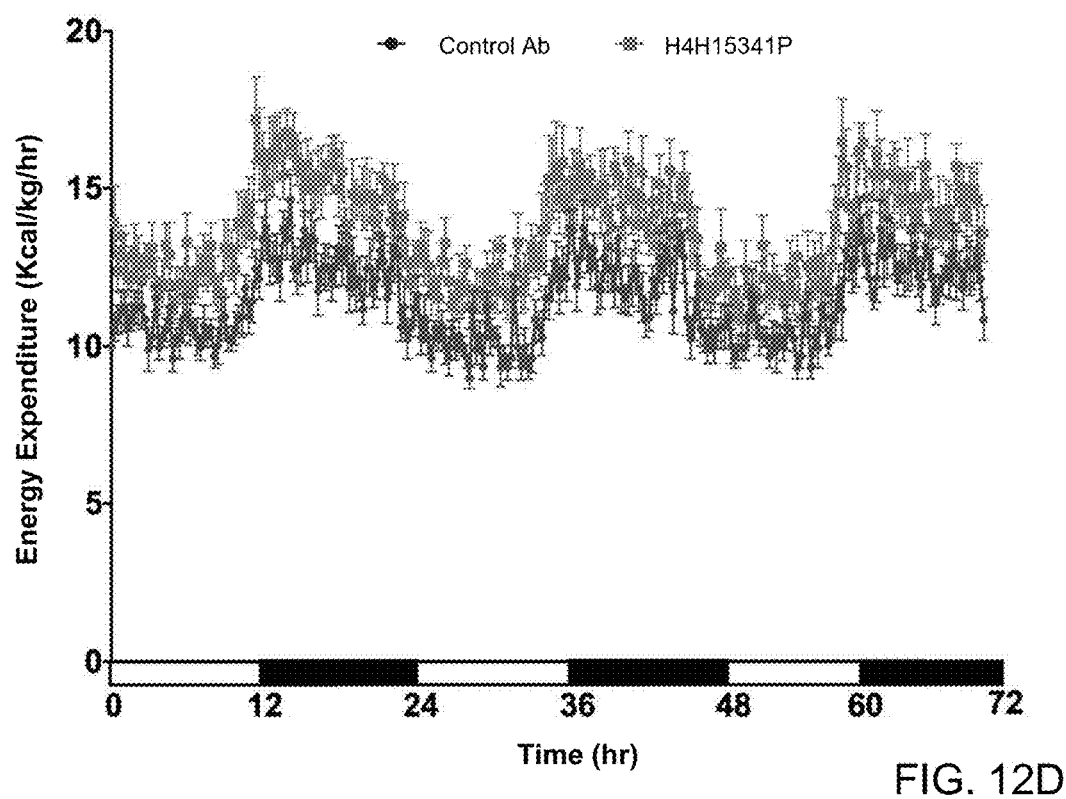
Figure 12E:
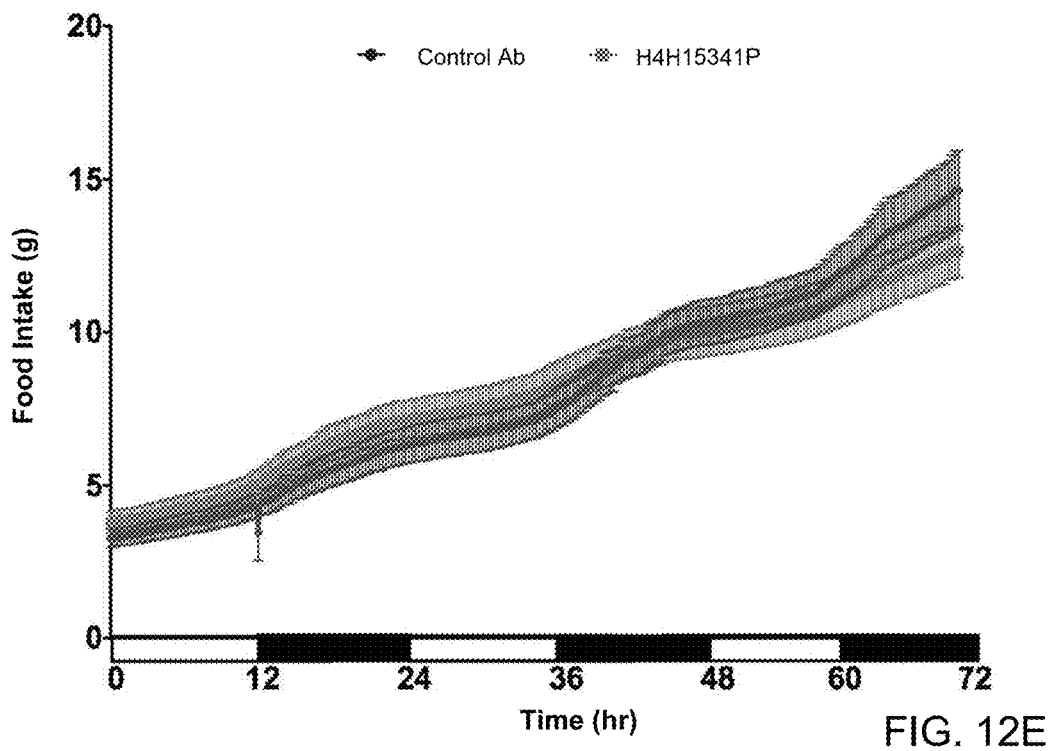
Figure 12F:
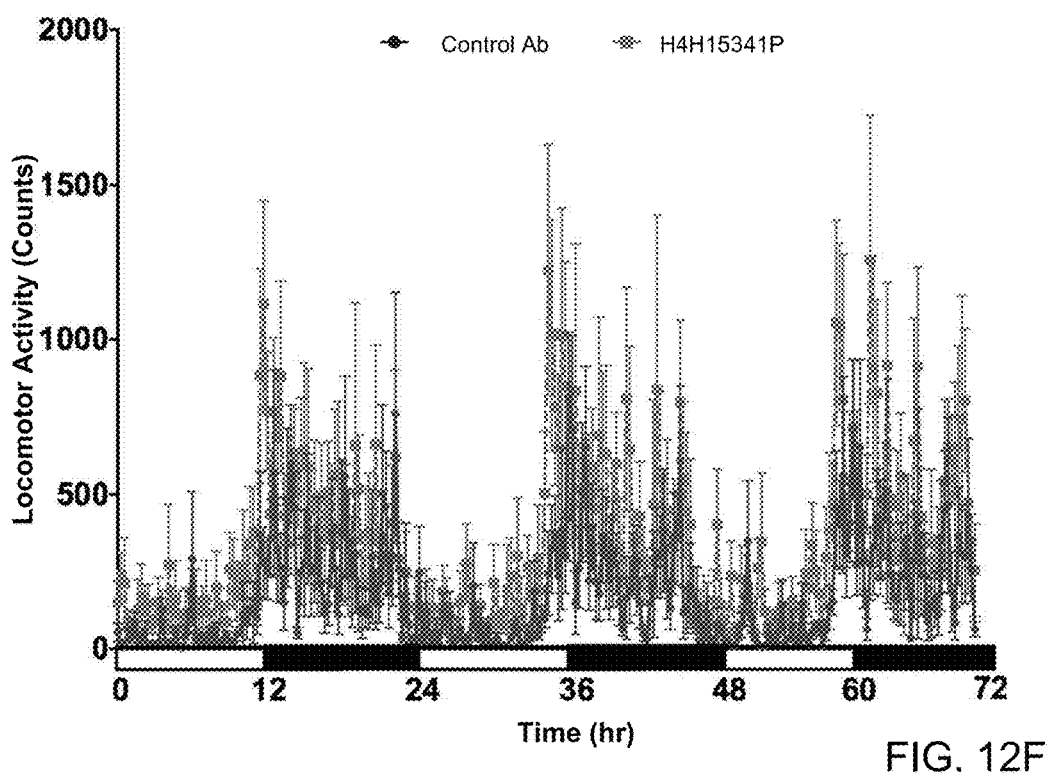
Figure 13A:
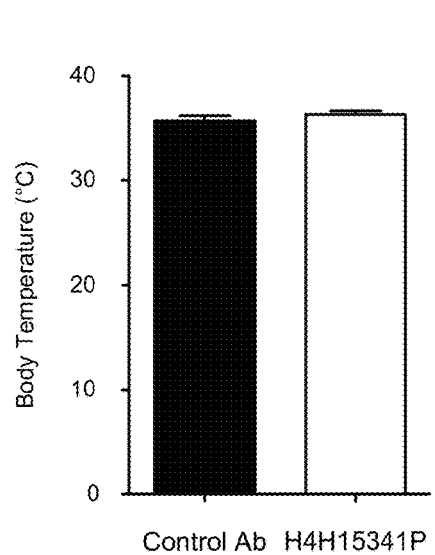
FIGS. 13A, 13B, 13C, 13D, 13E, 13F, and 13G. Weekly administration of H4H15341P to ANGPTL8$^{hum/hum}$ mice maintained on HFHC diet had no effect on body temperature or tissues TG storage. Body temperature was evaluated using rectal probe after 10 weeks of multiple dose injections of H4H15341P to HFHC-fed ANGPTL8$^{hum/hum}$ mice (13A). TG contents of liver (13B), heart (13C), gastrocnemius muscle (GA muscle) (13D), epididymal white adipose tissue (epiWAT) (13E), subcutaneous white adipose tissue (scWAT) (13F), and brown adipose tissue (BAT) (13G) were measured at the end of the study. All values are means±SEM. Statistical analysis was conducted by Welch's t-test.
Figure 13B:
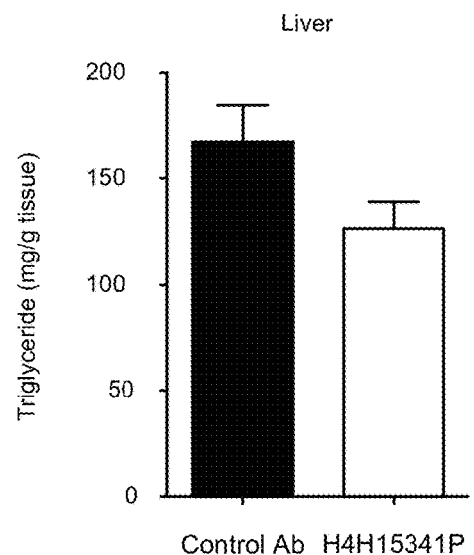
Figure 13C:
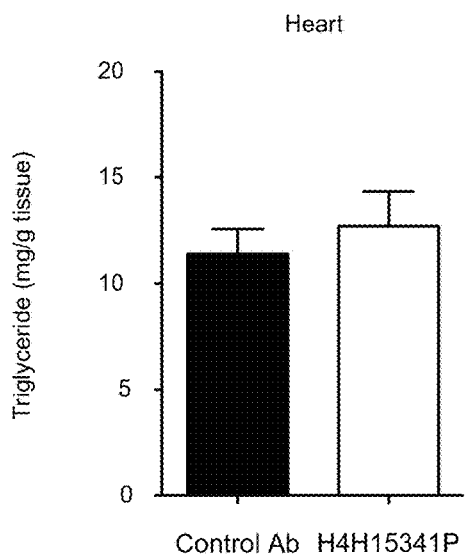
Figure 13D:
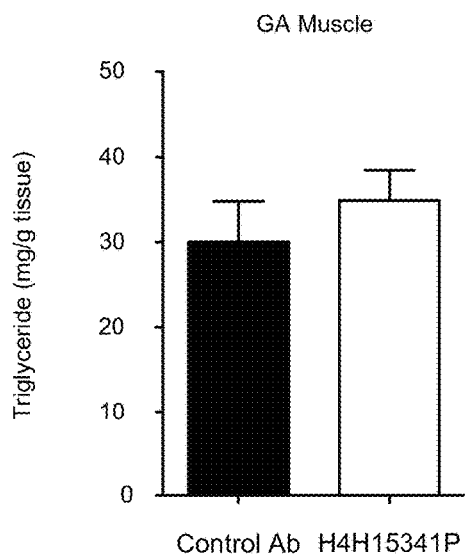
Figure 13E:
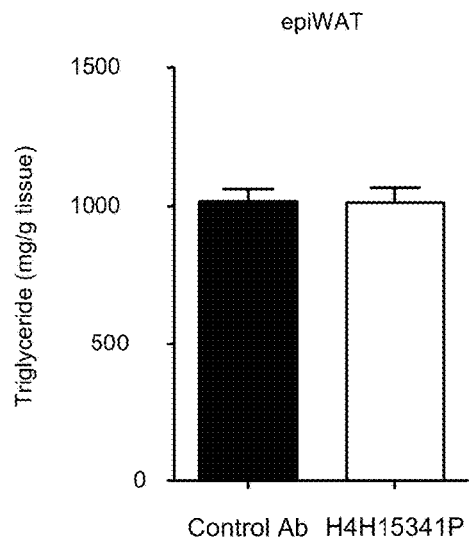
Figure 13F:
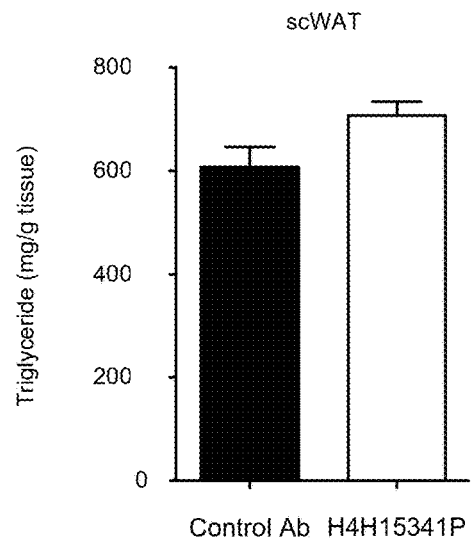
Figure 13G:
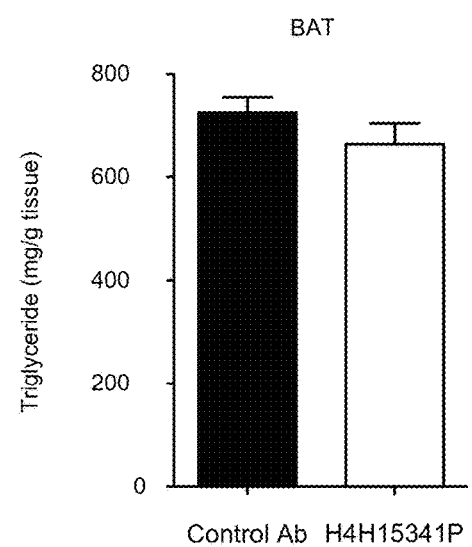
Figure 14A:
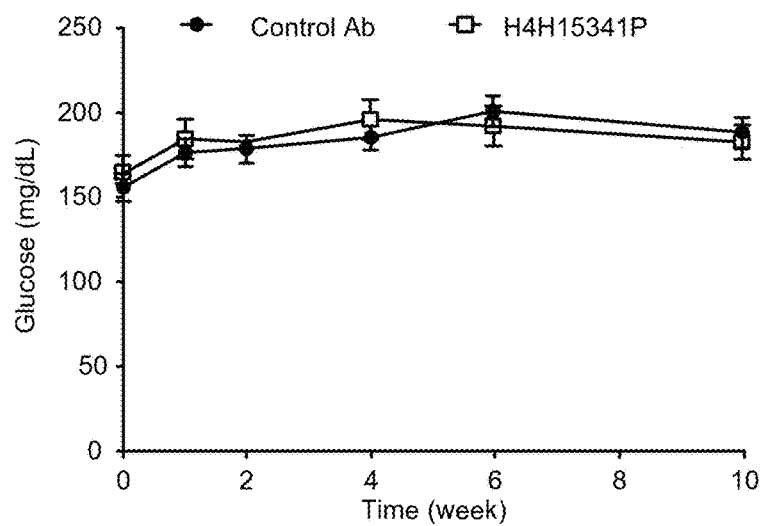
FIGS. 14A, 14B, and 14C. Weekly administration of H4H15341P to ANGPTL8$^{hum/hum}$ mice maintained on HFHC diet has no effect on glycemic control. Changes in non-fasted glucose (14A) were evaluated at multiple time points in the study described in FIG. 7A-7G. Glucose tolerance (14B) and insulin tolerance (14C) tests were conducted after 9 and 10 multiple doses of the antibodies, respectively. All values are means±SEM. Statistical analysis was conducted by repeated measures two-way ANOVA with Bonferroni's post-test.
Figure 14B:
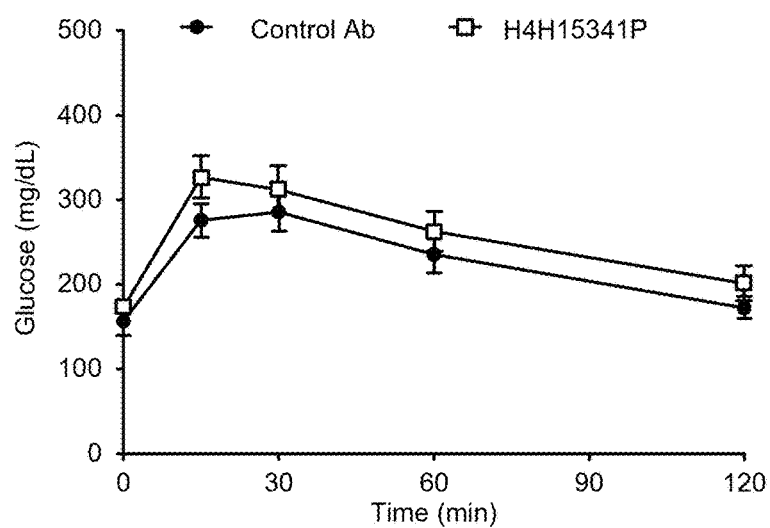
Figure 14C:
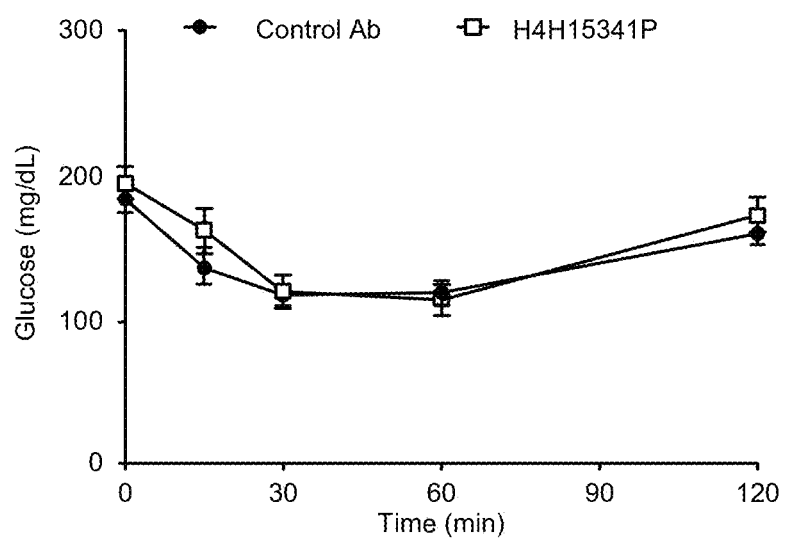

Metabolic cage analysis at week 14 revealed that mice treated with H4H15341P had increased $O_2$ consumption and $CO_2$ production (FIGS. 11A and 11B). H4H15341P treatment also led to an increase in energy expenditure that was either normalized to body weight (FIG. 7E) or calculated without body weight normalization using analysis of covariance (ANCOVA) with body weight as the covariance (FIGS. 11C and 11D). Antibody treatment did not affect the respiratory exchange ratio or food intake, but tended to increase locomotor activity (FIGS. 7D, 7F, and 7G). The raw traces for all metabolic cage data are shown in FIGS. 12A-12F. The core body temperature remained unchanged by H4H15341P treatment (FIG. 13A). Consistent with data in Angptl8$^{-/-}$ mice (Wang, Y., et al. 2013. PNAS USA 110: 16109-16114; Gusarova V et al. 2014. Cell 159(3):691-696), no effect of H4H15341P on glucose homeostasis was observed (FIGS. 14A-14C). These data show that ANGPTL8 inhibition reduced body fat content and body weight secondary to increased energy expenditure.

H4H15341P Modulates Serum TG and HDL-C in Dyslipidemic Cynomolgus Monkeys

Figure 8A:
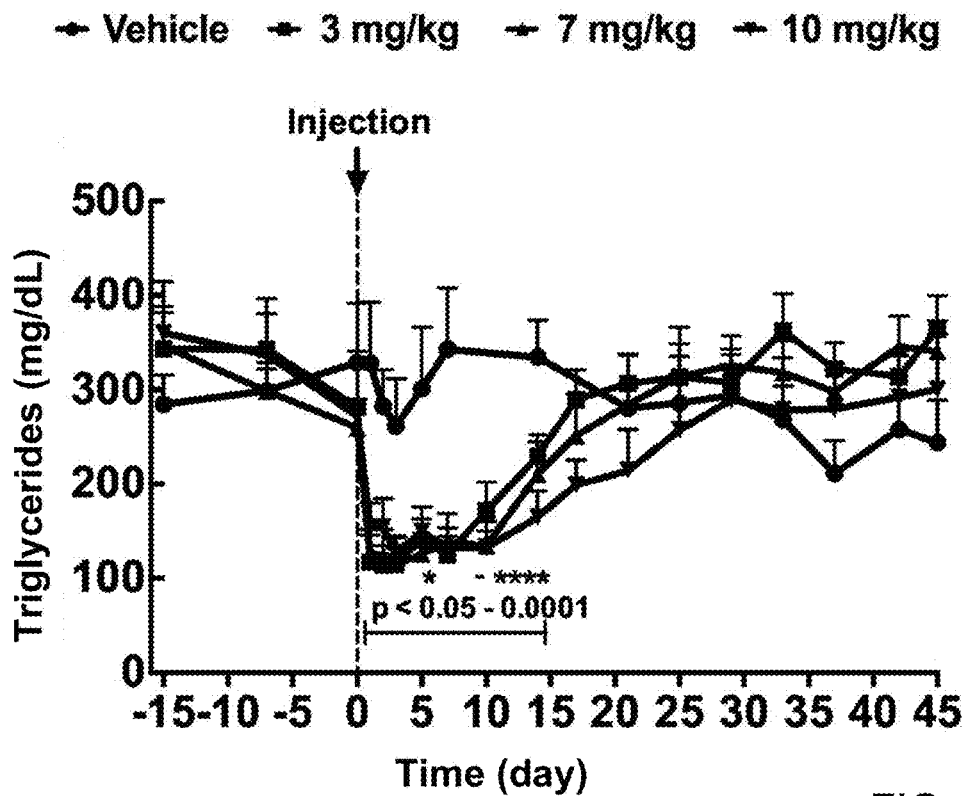
FIGS. 8A, 8B, 8C, 8D, 8E, and 8F. Single dose administration of H4H15341P to spontaneous hypertriglyceridemic cynomolgus monkeys lead to reduction in plasma triglycerides and increase in HDL-C. Baseline serum samples were collected at days −15, −7 and 0 from non-fasted animals. Eighteen monkeys were divided into three groups and administrated H4H15341P (3, 7 or 10 mg/kg). Saline was administered to 6 monkeys. Serum samples were collected at multiple days and analyzed for triglycerides (8A), HDL-C (8B) and LDL-C(C) and also represented as a percent change from baseline: triglycerides (8D), HDL-C (8E) and LDL-C (8F). All values are mean±SEM. Statistics was performed by repeated measures two-way ANOVA with Sidak's post-test. *P<0.05; P<0.01; *P<0.001; ****P<0.0001.
Figure 8B:
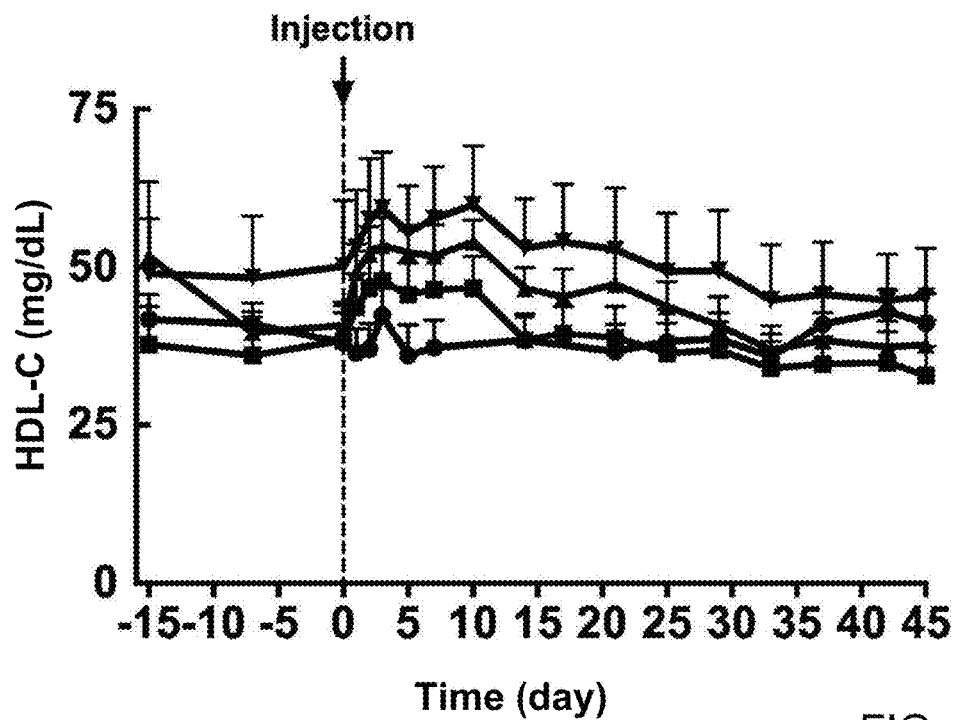
Figure 8C:
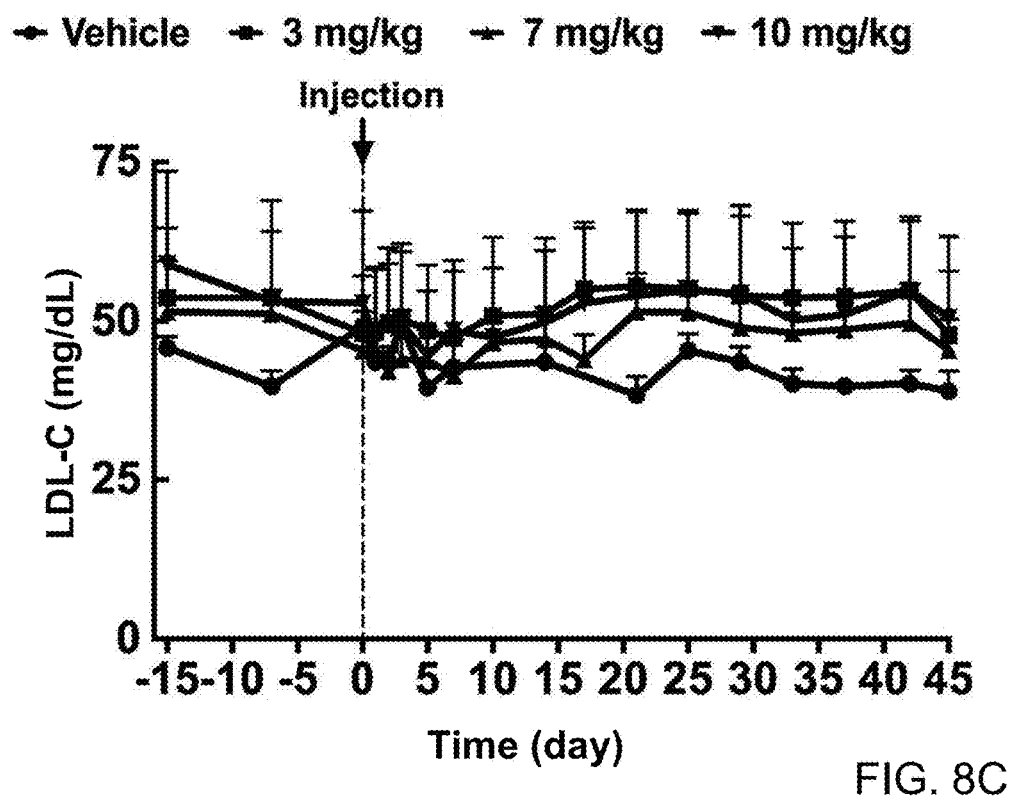
Figure 8D:
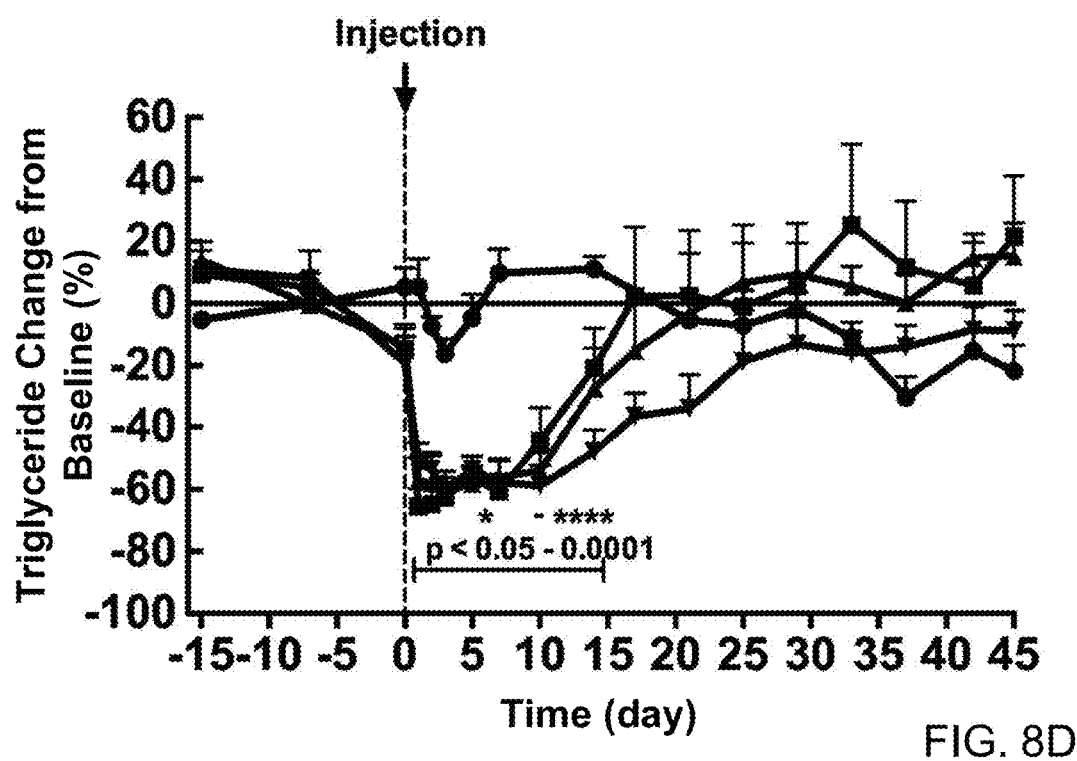
Figure 8E:
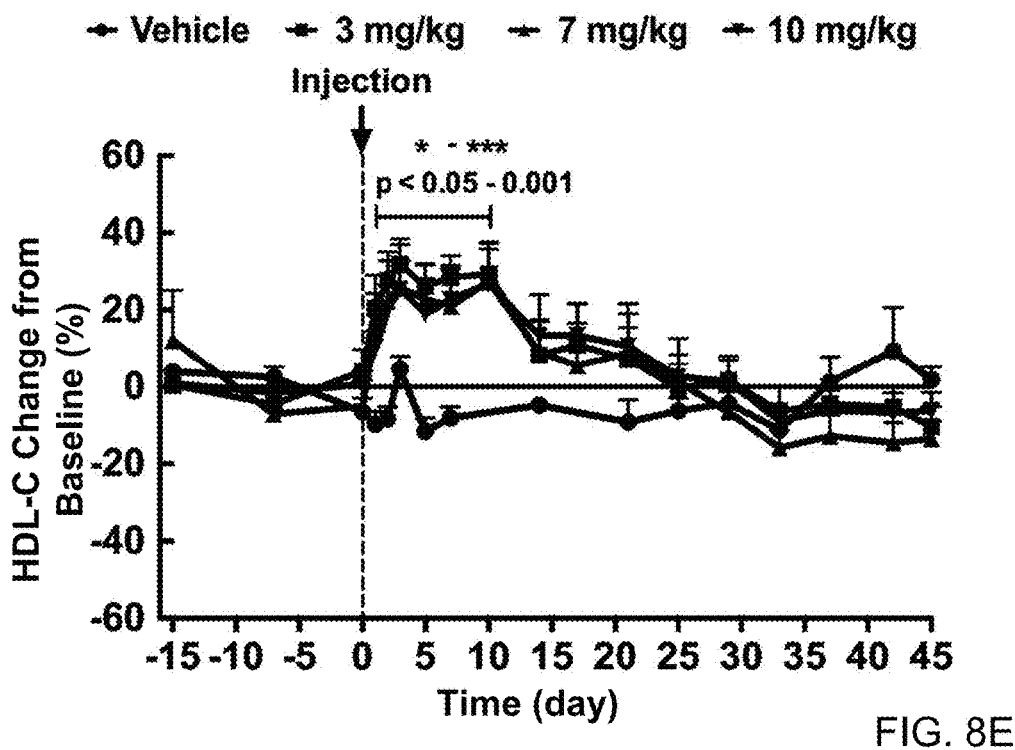
Figure 8F:
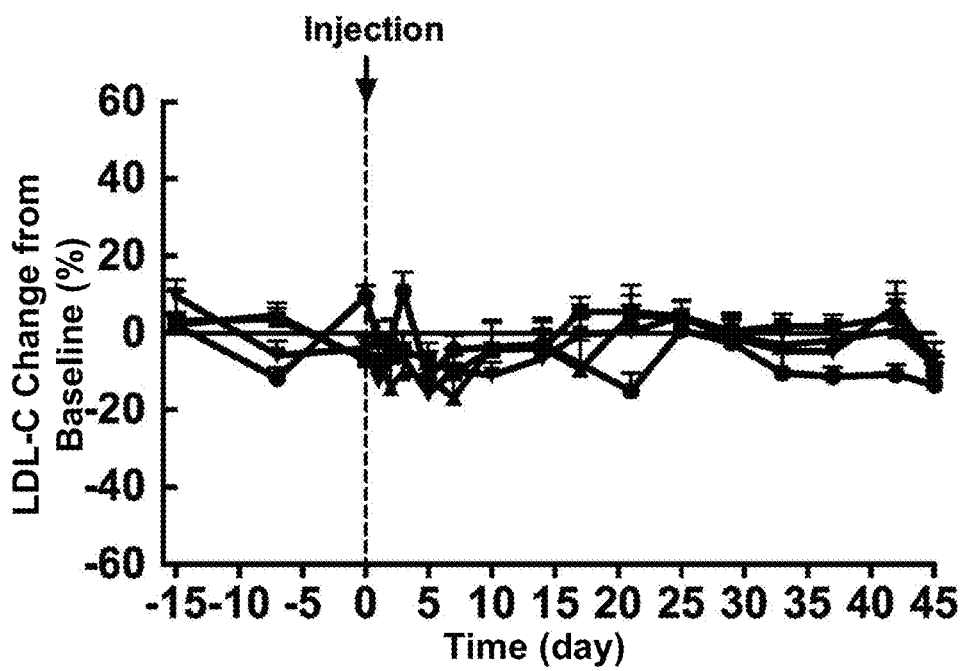

Finally, the effects of H4H15341P were evaluated on serum lipids in spontaneous dyslipidemic cynomolgus monkeys. Groups of 6 monkeys were given a single dose of H4H15341P at 3, 7 or 10 mg/kg. A group of monkeys was selected at the end of the washout period to receive the vehicle. H4H15341P produced robust and sustained dose-dependent reduction in circulating TGs that reached a maximum of −65% (from 323±20 mg/dl to 114±21 mg/dl; P<0.0001; n=6) within 1 day following antibody administration (FIGS. 8A and 8D). Interestingly, all doses resulted in same maximum reduction in TGs, however the duration of the effects was dose-dependent (FIG. 8A). Inhibition of ANGPTL8 also led to an increase in HDL-C by 30% at all doses (FIGS. 8B and 8E). No changes were observed in LDL-C (FIGS. 8C and 8F).

DISCUSSION

In this study, ANGPTL8 blockade is shown with the monoclonal antibody H4H15341P efficiently reduced circulating TGs through upregulation of LPL activity, which is consistent with the phenotype reported in Angptl8$^{-/-}$ animals (Wang, Y., F. et al. 2013. PNAS USA 110: 16109-16114; Gusarova, V., et al. 2014. Cell 159: 691-696). Additionally, H4H15341P reduced fat accumulation and body weight gain in mice when placed on HFHC diet. The reduction in body weight was secondary to increased energy expenditure. Moreover, ANGPTL8 blockade in spontaneous hypertriglyceridemic cynomolgus monkeys markedly reduced serum TGs and increased HDL-C. These data suggest that inhibition of ANGPTL8 with a monoclonal antibody may be beneficial for patients with hypertriglyceridemia and obesity.

Antibody inhibition of ANGPTL8 was recently reported to reduce TGs in normolipidemic 057B1/6 mice by 30%, but required 3 daily administrations at 30 mg/kg (Fu, Z., et al. 2015. Scientific Reports 5: 18502). The current study describes the development of a fully human monoclonal antibody to ANGPTL8 that effectively reduced circulating TGs at a single dose of mg/kg by 65% in mice and monkeys. ANGPTL8 inhibition reduced plasma TGs through disinhibition of LPL activity. ANGPTL8 antibody inhibition in the cynomolgus dyslipidemic monkeys also increased HDL-C by 30%, consistent with observations reported in human loss of function mutations in ANGPTL8 (Peloso, Gina M., et al. 2014. The American Journal of Human Genetics 94: 223-232.)

During refeeding, LPL activity is upregulated in WAT and reduced in heart and skeletal muscle (Goldberg, I. J., R. H. Eckel, and N. A. Abumrad. 2008. The Journal of Lipid Research 50: S86-S90). Deletion of Angptl8 in mice disrupts these changes in LPL activity; no postprandial reduction in LPL activity occurs in oxidative tissues with refeeding in these mice. As a consequence, TG is delivered to oxidative tissues rather than to adipose tissue. These data suggested that ANGPTL8 acts as a metabolic switch to redirect fatty acids from oxidative tissues to white adipose tissue after food intake (Wang, Y., F. et al. 2013. PNAS USA 110: 16109-16114).

Chronic inhibition of ANGPTL8 with multiple doses of H4H15341P reduced body weight gain and fat accumulation in Angptl8$^{hum/hum}$ mice on HFHC diet. The body weight reduction in H4H15341P treated mice is likely to result from increased energy expenditure. H4H15341P treatment did not change respiratory exchange ratio, indicating it does not alter fuel utilization. Reductions in body weight and adipose tissue mass were reported earlier in chow-fed Angptl8$^{-/-}$ mice (Wang, Y., F. et al. 2013. PNAS USA 110: 16109-16114). Thus, ANGPTL8 is an important regulator of TG storage in white adipose tissue.

In conclusion, ANGPTL8 inhibition with monoclonal antibody H4H15341P reduced circulating TGs in mice and monkeys through upregulation of LPL activity. Multiple dose administration of ANGPTL8 antibody to ANGPTL8$^{hum/hum}$ mice on HFHC diet reduced body weight and fat content. The data indicate that ANGPTL8 inhibition with a monoclonal antibody would be beneficial in patients with hypertriglyceridemia and obesity.

What is claimed is:

1. A method for achieving a reduction of body weight in a subject, the method comprising administering an ANGPTL8 inhibitor, wherein the ANGPTL8 inhibitor is an antibody or antigen-binding fragment thereof specific for ANGPTL8, or a pharmaceutical composition comprising the antibody or antigen-binding fragment thereof, to the subject, wherein the antibody or antigen-binding fragment thereof comprises heavy and light chain complementarity determining regions (CDRs) of a heavy chain variable region (HCVR)/light chain variable region (LCVR) amino acid sequence pair having SEQ ID NOs: 162/170, wherein a reduction of body weight in the subject is achieved.

2. A method for achieving a reduction of fat mass in a subject, the method comprising administering an ANGPTL8 inhibitor, wherein the ANGPTL8 inhibitor is an antibody or antigen-binding fragment thereof specific for ANGPTL8, or a pharmaceutical composition comprising the antibody or antigen-binding fragment thereof, to the subject, wherein the antibody or antigen-binding fragment thereof comprises heavy and light chain complementarity determining regions (CDRs) of a heavy chain variable region (HCVR)/light chain variable region (LCVR) amino acid sequence pair having SEQ ID NOs: 162/170, wherein a reduction of fat mass in the subject is achieved.

3. A method for increasing energy expenditure in a subject, the method comprising administering an ANGPTL8 inhibitor, wherein the ANGPTL8 inhibitor is an antibody or antigen-binding fragment thereof specific for ANGPTL8, or a pharmaceutical composition comprising the antibody or antigen-binding fragment thereof, to the subject, wherein the antibody or antigen-binding fragment thereof comprises heavy and light chain complementarity determining regions (CDRs) of a heavy chain variable region (HCVR)/light chain variable region (LCVR) amino acid sequence pair having SEQ ID NOs: 162/170, wherein energy expenditure in the subject is increased.

4. A method for increasing HDL-C in a subject, the method comprising administering an ANGPTL8 inhibitor, wherein the ANGPTL8 inhibitor is an antibody or antigen-binding fragment thereof specific for ANGPTL8, or a pharmaceutical composition comprising the antibody or antigen-binding fragment thereof, to the subject, wherein the antibody or antigen-binding fragment thereof comprises heavy and light chain complementarity determining regions (CDRs) of a heavy chain variable region (HCVR)/light chain variable region (LCVR) amino acid sequence pair having SEQ ID NOs: 162/170, wherein HDL-C in the subject is increased.

5. The method of any one of claims 1-4, wherein the antibody or antigen-binding fragment thereof specific for ANGPTL8 comprises a heavy chain variable region/light chain variable region (HCVR/LCVR) sequence pair as set forth in SEQ ID NOs: 162/170.

6. The method of claim 4, wherein circulating triglycerides (TGs) in said subject are reduced by at least 50% one day after said administering of an ANGPTL8 inhibitor.

7. A method for treating obesity, or at least one symptom or complication associated with obesity, by administering an ANGPTL8 inhibitor, wherein the ANGPTL8 inhibitor is an antibody or antigen-binding fragment thereof specific for ANGPTL8, or a pharmaceutical composition comprising the antibody or antigen-binding fragment thereof, to a patient in need thereof, such that the obesity is mediated, or the at least one symptom or complication associated with the obesity is alleviated or reduced in frequency or severity, wherein the antibody or antigen-binding fragment thereof comprises heavy and light chain complementarity determining regions (CDRs) of a heavy chain variable region (HCVR)/light chain variable region (LCVR) amino acid sequence pair having SEQ ID NOs: 162/170.

8. The method of claim 7, wherein the method additionally comprises administering a secondary therapeutic agent to the patient.

9. The method of claim 8, wherein the second therapeutic agent is selected from the group consisting of an isolated antibody, or an antigen-binding fragment thereof, that specifically binds to angiopoietin-like protein 3 (ANGPTL3), angiopoietin-like protein 4 (ANGPTL4), angiopoietin-like protein 5 (ANGPTL5), angiopoietin-like protein 6 (ANGPTL6) and human proprotein convertase subtilisin/kexin type 9 (PCSK9).

10. The method of claim 8, wherein the second therapeutic agent is selected from the group consisting of insulin, a biguanide, a sulfonylurea, a PPAR gamma agonist, an alpha glucosidase inhibitor, a glucagon-like peptide 1 (GLP-1) agonist, or an analogue of any of the foregoing, a dipeptidyl peptidase IV (DPP-4) inhibitor, a sodium-glucose co-transporter 2 (SGLT2) inhibitor, a glucagon receptor antagonist, a non-sulfonylurea secretagogue, an insulin analog, exendin-4 polypeptides, beta 3 adrenoceptor agonists, inhibitors of cholesterol uptake and/or bile acid re-absorption, LDL-cholesterol antagonists, cholesteryl ester transfer protein antagonists, endothelin receptor antagonists, growth hormone antagonists, insulin sensitizers, amylin mimetics or agonists, cannabinoid receptor antagonists, melanocortins, melanin-concentrating hormone receptor agonists, SNRIs, a fibroblast growth factor 21 (FGF21) mimetic, a fibroblast growth factor receptor 1c (FGFR1c) agonist, an inhibitor of advanced glycation endproduct formation, and protein tyrosine phosphatase inhibitors.

* * * * *